United States Patent
Giordano et al.

(10) Patent No.: US 9,505,708 B2
(45) Date of Patent: Nov. 29, 2016

(54) PROCESS FOR THE PRODUCTION OF RALFINAMIDE SALTS SUBSTANTIALLY FREE FROM IMPURITIES HAVING GENOTOXIC EFFECTS

(75) Inventors: Claudio Giordano, Milan (IT); Erwin Waldvogel, Aesch (CH)

(73) Assignee: NEWRON PHARMACEUTICALS S.P.A., Bresso (MI) (IT)

( * ) Notice: Subject to any disclaimer, the term of this patent is extended or adjusted under 35 U.S.C. 154(b) by 0 days.

(21) Appl. No.: 13/643,716

(22) PCT Filed: Apr. 6, 2011

(86) PCT No.: PCT/EP2011/055309
§ 371 (c)(1),
(2), (4) Date: Oct. 26, 2012

(87) PCT Pub. No.: WO2011/134763
PCT Pub. Date: Nov. 3, 2011

(65) Prior Publication Data
US 2013/0039983 A1    Feb. 14, 2013

(30) Foreign Application Priority Data
Apr. 27, 2010 (EP) .................... 10161207

(51) Int. Cl.
C07C 237/22     (2006.01)
A61K 31/165     (2006.01)
C07C 237/08     (2006.01)
C07C 231/24     (2006.01)

(52) U.S. Cl.
CPC ........... C07C 237/08 (2013.01); A61K 31/165 (2013.01); C07C 231/24 (2013.01)

(58) Field of Classification Search
CPC . C07C 231/24; C07C 231/22; C07C 233/08; C07C 273/20
See application file for complete search history.

(56) References Cited

U.S. PATENT DOCUMENTS

2004/0213842 A1*   10/2004   Burgard et al. ............... 424/464

FOREIGN PATENT DOCUMENTS

| WO | 2006/027052 A2 | 3/2006 |
| WO | 2007/147491 A1 | 12/2007 |
| WO | 2009/074478 A1 | 6/2009 |

OTHER PUBLICATIONS

Elder, D. P.; Delaney, E.; Teasdale, A.; Eyley, S.; Reif, V. D.; Jacq, K.; Facchine, K.; Oestrich, R. S.; Sandra, P.; David, F. The utility of sulfonate salts in drug development. Journal of Pharmaceutical Sciences, vol. 99, No. 7, Jul. 2010. First published online Jan. 28, 2010.*
http://onlinelibrary.wiley.com/doi/10.1002/jps.22058/pdf cited on Sep. 8, 2015.*
First Examination Report issued on Jun. 21, 2013 in counterpart New Zealand Application No. 602648.
Reply to the First Examination Report of counterpart New Zealand Application No. 602648 dated Oct. 17, 2013.
Second Examination Report issued on Nov. 4, 2013 in counterpart New Zealand Application No. 602648.
Reply to the Second Examination Report of counterpart New Zealand Application No. 602648 dated Jul. 3, 2014.
Amendments to the Specification filed on Jul. 3, 2014 with the Reply to the Second Examination Report of counterpart New Zealand Application No. 602648 (clean and markup copy).
Third Examination Report issued on Jul. 21, 2014 in counterpart New Zealand Application No. 602648.

* cited by examiner

*Primary Examiner* — Jessica Worsham
(74) *Attorney, Agent, or Firm* — Silvia Salvadori, P.C.; Silvia Salvadori

(57) ABSTRACT

The invention relates to a new process for the production and/or purification of the salt of the compound (S)-2-[4-(2-fluorobenzyloxy) benzylamino]propanamide, i.e. ralfinamide, or the respective R-enantiomer, with methane sulfonic acid in high yields and very high enantiomeric and chemical purity in the form of the crystalline anhydrous polymorph identified as form A, wherein said salt is substantially free from impurities having genotoxic effect, such as (C1-C5) alkanylmethanesulfonates, and residual solvents known as potential precursors thereof, such as (C1-C5)alkanols or esters thereof with lower alkanoic acids.

7 Claims, 14 Drawing Sheets

PROCESS FOR THE PRODUCTION OF RALFINAMIDE SALTS SUBSTANTIALLY FREE FROM IMPURITIES HAVING GENOTOXIC EFFECTS

This application is a U.S. national stage of PCT/EP2011/055309 filed on Apr. 6, 2011, which claims priority to and the benefit of European Application No. 10161207.5, filed on Apr. 27, 2010, the contents of which are incorporated herein by reference in their entirety.

The present invention relates to a new process for the production and/or purification of salts of methanesulfonic acid of (S)-2-[4-(2-fluorobenzyloxy)benzylamino]propanamide, i.e. ralfinamide (Ia) or

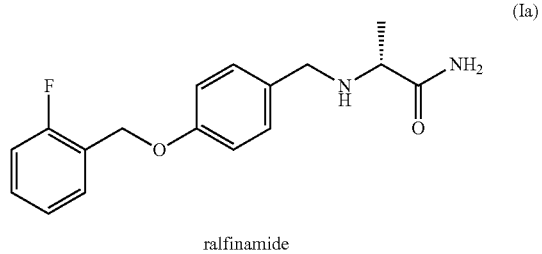 [SMILES: C[C@@H](NCc1ccc(OCc2ccccc2F)cc1)C(N)=O]

ralfinamide the respective R-enantiomer (I'a). The process of this invention allows the production of the above salts in high yields and very high enantiomeric and chemical purity as required for industrial scale manufacture, wherein said salts are substantially free from impurities having genotoxic effects and residual solvents known as potential precursors thereof.

PRIOR ART

Several salts of ralfinamide are disclosed in the prior art (WO 90/14334; P. Pevarello et al., J. Med. Chem., 1998, 41:579). The methanesulfonate salts of ralfinamide and its R-enantiomer are particularly useful for use in the preparation of medicaments for the treatment of several disorders, including, Parkinson's disease, seizure, pain (including mixed and combined pain), migraine, bipolar disorders, depressions, cardiovascular, inflammatory, urogenital, metabolic, gastrointestinal, cognitive and psychiatric disorders (WO 90/14334, WO 99/35125, WO 03/020273, WO 2004/089353, WO 2005/102300, WO 2004/062655, WO 2005/018627, WO 2006/070405, WO 2006/027052, WO 2007/144153, WO 2009/080470 and WO 2009/109334; Stummann T. C. et al., Eur J Pharmacol 2005, 510:197-208; Shi-Hong Zhang et al., Pain 2008, 139:293-305; Yamane H. et al., Exp. Neurol. 2007, 208(1):63-72).

Industrial scale preparations of high purity methanesulfonate salt of ralfinamide and, the respective R-enantiomer have been described in WO 2007/147491 and WO 2009/074478.

In general, the preparation of the salts of ralfinamide and its R-enantiomer involves the salification of the respective bases with a suitable pharmaceutically acceptable acid in the last step of the process.

In particular the salts with organic acids suitable for pharmaceutical use, are generally synthesized by adding a stoichiometric amount of the acid of choice to a solution of the corresponding base in an organic solvent.

According to the preparations and crystallizations of the methanesulfonate salts of ralfinamide and its R-enantiomer described in the prior art, isopropanol or ethylacetate is employed as the solvent.

In particular, both WO 2007/147491 and WO 2009/074478 disclose crystallization of the methanesulfonate salt of ralfinamide from isopropanol (2-propanol).

The preparation and crystallization from ethyl acetate of the methanesulfonate salt of the 3-fluoro analog of ralfinamide (i.e., safinamide) is disclosed in both WO 2007/147401 and WO 2009/074478. This latter document discloses also the preparation and crystallization of the R-enantiomer of ralfinamide methanesulfonate salt from isopropanol or ethyl acetate (see also WO 2006/027052).

Both WO 2007/147401 (Example 13, Table 15) and WO 2009/074478 (Example 21, Table 6) describe a crystallization of safinamide methanesulfonate from a mixture of acetone/water. The yields reported in both cases (18-20%) are much lower in comparison with those resulting from the use of isopropanol or ethyl acetate (generally above 90%) and, therefore, would not suggest any use of said solvents mixture in industrial scale preparations and purification processes of its 2-fluoro analog.

Moreover, neither WO 2007/147491 nor WO 2009/074478 gives indications about the polymorphism and the residual content of genotoxic impurities or solvents known as potential precursors thereof of the safinamide methanesulfonate product obtained by using the mixture of acetone/water as the crystallization solvent.

So far, the methanesulfonates of ralfinamide and its R-enantiomer, obtained by the prior art methods, have been analysed in order to determine the HPLC purity, the enantiomeric purity and the content of the respective bis-benzylated side-products, (S) or (R)-2-[3-(2-fluorobenzyl)-4-(2-fluorobenzyloxy)benzylamino]propanamide, as an impurity (WO 2007/147491 and WO 2009/074478) having inhibitory effects on CYP 450 enzymes and HERG channel blocking properties. No physical characterisation of these salts at solid state form, besides the melting point is reported in the above cited prior art.

BACKGROUND OF THE INVENTION

In general, the salts of active pharmaceutical ingredients containing an amino group, which are commercially available or under medical investigation activity, with the exception of the quaternary ammonium salts, are generally prepared by contacting the corresponding amine with an organic or inorganic acid and are crystallized from solvents; see, for instance, the preparation of the following methanesulfonate salts (mesylates): amidephrine mesylate (RN 1421-68-7), betahistine mesylate, bromocriptine monomesylate (25614-03-3), deferoxamine mesylate, dihydroergocristine, dihydroergotamine mesylate, doxazin mesylate, perfloxacin monomesylate dehydrate (RN 70458-95-6), nelfinavir mesylate (RN 159989-65-8), pergolide mesylate (RN 66104-23-2), phentolamine mesylate, and saquinavir monomesylate (RN 149845-06-7) and the preparation of other salts of API such as indinavir sulphate (RN 157810-81-6), omoconazole nitrate (RN 83621-06-1), quinine sulphate (RN 549-56-4), racefemine hydrogen fumarate (RN 1590-35-8), ramosetron hydrochloride (RN 132907-72-3), and ropivacaine hydrochloride (RN 98717-15-8).

The crystallization of the salts has the aim to increase the salt purity by removing impurities which can be classified (Duane A. Pierson et al., Organic Process Research and Development 2009, 13(2):285-291) on the basis of decreasing risk potential, as:

Class 1—Impurities known to be genotoxic and carcinogenic

Class 2—Impurities known to be genotoxic

Class 3—Alerting structure, unrelated to API and of unknown genotoxic potential

Class 4—Alerting structure related to the API

Class 5—No alerting structure

Solvents used in the last step of the API manufacturing process, in particular for the preparation of the desired API salt, its crystallization and any other kind of API purification must be selected taking into account the properties of both solvents and substrates. The used solvents should be inert. For inert solvents are generally meant those which do not react with the salts of API, with API and/or with the salt forming acid or base.

Although crystallisation from a solvent is an important tool to remove impurities from a salt of an API, when inappropriate solvent is used, the crystallized salt could be contaminated by new impurities.

The European Medicine Agency (EMEA) has divided organic solvents usually employed in API manufacturing processes in three categories on the basis of their toxicological properties (EMEA: Notice for Guidance on Impurities: Residual Solvents, CPMP/ICH/283/95, March 1998).

Solvents of EMEA class 3 (acetone, 2-propanol, ethyl acetate etc.) are the preferred ones for the preparation and purification of salts of basic API with acids, on condition that they do not react with the active base substrate, the acid and/or the salt. Indeed, certain precautions must be taken when the basic API and or the acid contain chemical groups that can react with the solvent.

As a general rule, use of alkyl esters as solvents should be avoided, when API is a primary or secondary amine, as the amino group is reactive with respect to the carboxyalkyl moiety yielding amides. This would lead to partial loss of API and generation of API structurally related impurities (March's Advanced Organic Chemistry, Reactions, Mechanism, and Structure 6th Edition, Michael B. Smith and Jerry March, John Wiley & Sons, Inc. Hoboken, N.J., 2007, 1434-1436).

Moreover, alkylesters, such as ethyl acetate, might react with alkyl and aryl sulfonic acids, used for the salification of the active substance free base, with formation of an alkylester, e.g. the ethyl ester, of the sulfonic acid of choice.

With APIs containing primary and/or secondary amino group(s), use of ketones as solvents is generally not advisable as they could condensate with primary amines (Schiff bases formation) and secondary amines (enamines formation) generating API structurally related impurities (March's Advanced Organic Chemistry, Reactions, Mechanism, and Structure Sixth Edition, Michael B. Smith and Jerry March, John Wiley & Sons, Inc. Hoboken, N.J., 2007, 1281-1284).

In addition, ketones in the presence of both strong acids and bases could promote formation of impurities due to self condensation.

Use of alkanols as solvents should be avoided as primary, secondary and tertiary alcohols can react with the acid of choice generating the respective alkylester, which might exhibit alkylating ability and, consequently, might have genotoxic effects (L. Miller et al., Regulatory Toxicology and Pharmacology 44 (2006), 198-211).

The effect becomes more evident when the acid of choice is a strong acid and it is used in a quantity which exceeds the stoichiometic amount and/or the base is added to the acid. Mesylate esters of lower ($C_1$-$C_5$) alkanols, in particular ($C_1$-$C_3$) alkanols, are reactive, direct-acting, substances which have revealed that their DNA alkylation action can induce mutagenic, carcinogenic and teratogenic effect.

Because of their ability to induce genetic mutations and/or chromosomal rearrangements, control of genotoxic and carcinogenic impurities in pharmaceutical substances has become relevant in recent years.

Guidelines from Regulatory Agencies have been recently published outlining limits for testing and control of potential genotoxic impurities (GTIs). For example the European Medicines Agency (EMEA) Committee for Medicinal Products for Human Use (CHMP) has defined a threshold of toxicological concern (TTC) according to which a 1.5 µg/day intake of a genotoxic impurity is considered to be an acceptable risk. From this threshold value, a permitted level in the active pharmaceutical ingredient (API) can be calculated based on the expected daily dose of the active ingredient [Concentration limit (ppm)=TTC [µg/day]/dose (g/day)]. For a drug taken at a dose of 100 mg/day, this equates to a concentration limit of 15 ppm for each potential genotoxic impurity. This represents levels significantly lower than the conventional ICH (International Conference on Harmonization) (ICH Harmonized Tripartite Guidelines, "Impurities in new drug substances" Q3A(R2), 25 Oct. 2006) identification threshold for impurities, which provides a challenge for analytical scientist to develop sensitive analytical methodologies for monitor and quantify the GTIs.

Concerns which are emerging over the possible formation of sulfonic acids lower alkyl esters during the preparation of sulfonate salts (Elder D. P. et al., J. Pharmacy and Pharmacology, 2009, 61:269-278) of API by addition of the alkyl or aryl sulfonic acid (e.g., methanesulfonic acid) to the free base dissolved in the lower alkanol solvent, have led Regulatory Agencies to require applicants for marketing authorization to demonstrate that the drug has a content of alkyl and aryl sulfonates that do not exceed the limits indicated by the Authorities. (Lutz Muller et al., Regulatory Toxicology and Pharmacology 2006, 44; 198-211). Thus it becomes mandatory to verify that formation of alkyl- or aryl-sulfonic acid ester does not occur during the preparation of the API salt and assure that commercial alkyl or aryl sulfonic acids, in particular methanesulfonic acid, used as acid starting materials are not contaminated by the corresponding lower alkylesters. EMEA guidelines for genotoxic impurities set limits for methyl, ethyl, isopropyl methanesulfonates (MMS, EMS, IMS), besylates and tosylates (EMEA/CHMP/CVMP/QWP/66297/2008 of Jan. 24, 2008 and EMEA/CHMP/QWP/251334/2006).

In this framework, Regulatory Authorities (EDA, EMEA) continue to request developing processes for obtaining active substances with higher purity degree and lowest environmental impact.

Testing for genotoxic impurities in active pharmaceutical ingredients (API) involves a number of challenges common to trace analysis.

The most significant analytical challenges are related to three main problems: the first one regards the structural difference between the genotoxic impurities and the main compound, so that different analytical approaches are needed; the second one is related to the respective reactivity or instability, so that special handling techniques are required; the third one is introduced by the sample matrix where "matrix" means all components but analite, i.e. sample solubility and/or chromatographic interferences due to the main components.

Even if analytical methods for the most common genotoxic impurities are described in the relevant literature, each new sample matrix needs to be studied for optimizing analytical selectivity and sensitivity.

The first step of the development of an analytical method for quantification of genotoxic impurities is the selection of the analytical technique; this choice is based on the chemical structure of the analyte and on the limits to be determined. Commonly used techniques are gas chromatography for the volatile genotoxic impurities and HPLC for the non-volatile ones. The use of the mass detector in Single Ion Monitoring (SIM) is considered as the most versatile, sensitive and selective technique for trace analysis, but the type of instrument available, especially the ionization source, and the analysts expertise are critical issues. Flame Ionization Detector (FID), Electron Capture Detector (ECD) and Ultraviolet UV detection can also be used if separation of the analytes peak from the API peak is sufficient; however these methods are less selective.

For very reactive and unstable compounds the derivatization approach can be considered: however, this approach cannot be used if the derivatizing agent can react with the API itself. In this case, the matrix deactivation or elimination or the direct analysis have to be optimized.

Finally, validation issues should be considered. Methods used for the control of genotoxic impurities can be based on limit tests or quantitative tests. In the first case the analyte in the tested sample is compared with a standard solution containing it in a known concentration and the evaluation is based on the determination whether the analyte response is lower or higher than the standard response, in the second case the concentration of the analyte is numerically defined. The extension of the validation depends on the evaluation method, which is chosen, being the requirements, of the validation for a quantitative method more stringent than those for a limit method: specificity as no interference assessment and sensitivity as demonstration that the Limit of Detection (LOD) is lower than the required limit have to be demonstrated by using the limit test approach, while linearity and Limit of Quantitation (LOQ), precision, accuracy and robustness are also necessary by using the quantitative approach.

According to the above mentioned guidelines Q3A(R2) of 25 Oct. 2006, impurities contained in an amount of 0.10% or above in new drug substances (API) to be administered at a daily dose lower than 2 g/day, should be identified (i.e. their structural characterisation has to be achieved); moreover; impurities contained in an amount of 0.15% or above should be qualified (i.e., biological data establishing safety at the specified level should be achieved).

In order to decrease the risks due to the use of solvents in the synthesis stage of an API, efforts have been devoted to the aim of running reactions in the absence of organic solvents. However, often, the advantage of solvent-free liquid phase reactions is decreased by the fact that the use of organic solvents may be requested in the final purification steps, (Koichi Tanaba, Solvent-free Organic Synthesis, 2009 Wiley-VCH).

On the other hand, notwistanding the use of organic solvents in the formation or crystallization of solid state API salts is quite common in the pharmaceutical practice, it may involve environmental problems, such as the risk of danger of fire and explosion, and the toxicity against the workers, in addition to the problems which may arise from contamination of the finished medicament by residual solvents. The residual amounts of the solvent(s) in the active ingredient and/or in the finished medicament can be decreased only by an extension of the drying time or a prolonged heating of the API solid state salt and/or the finished pharmaceutical form, leading to a disadvantageous decrease in the productivity of the whole manufacturing process.

As a matter of fact, when organic solvents are employed for the preparation and/or crystal ligation of API salts, such as ralfinamide methanesulfonate or its R-enantiomer, these salts are contaminated by a residual amount of organic solvents. In the case of formation or crystallization of said methanesulfonate salts from either lower alkanols or alkylesters, formation of lower alkyl esters of methanesulfonic acid may occur in the final product and said impurities may be present as genotoxic contaminants. Moreover, when the residual solvent is either a lower alkanol or alkylester, a lower alkylester of methanesulfonic acid might be formed.

DESCRIPTION OF THE INVENTION

No specific disclosure or information regarding the solid form of ralfinamide methanesulfonate and its R-enantiomer, with respect to the content of residual solvents and genotoxic impurities and the crystalline characterization (Polymorphism in Pharmaceutical Solids—edited by Harry G. Brittain 1999—Marcel Dekker, Inc. N.Y.), has been reported in the prior art.

Samples of solid anhydrous ralfinamide methanesulfonate and the respective R-enantiomer, prepared as specified in the prior art, by using isopropanol or ethylacetate as the solvent (WO 2007/147491, WO 2006/027052 and WO 2009/074478), have now been analyzed in order to determine the level of residual solvents and genotoxic contaminants and the crystalline properties. Now the crystalline structure of the ralfinamide methanesulfonate salt has been determined. FIG. 1 represents a X-Rays Powder Diffraction (PXRD) pattern of the ralfinamide methanesulfonate salt obtained according to the methods described in WO 2007/147491 and WO 2009/074478 and, as discussed in more detail hereafter, shows that said salt always consists of the same anhydrous polymorph, hereinafter identified as form A. Analogous results have been obtained with the R-enantiomer of ralfinamide methanesulfonate obtained according to the method described in WO 2006/027052 and WO 2009/074478. Analytical tests performed on the methanesulfonate salt of both ralfinamide and its R-enantiomer prepared according to the above mentioned prior art methods show that these salts are contaminated by a certain amount of residual solvents and by traces of genotoxic alkyl-methanesolfonates (See Examples 18 and 19). The amount of residual solvents (Isopropanol or ethylacetate) and genotoxic contaminants such as methyl methanesulfonate, (MMS), ethyl, methanesulfonate (EMS) and isopropyl methanesulfonate (IMS) has been found to be lower than the limits prescribed by the Regulatory Authorities (e.g. EMEA Guidelines on the Limits of Genotoxic Impurities. EMEA/CHMP/QWP/231334/2000; EMEA "Note for Guidance on Impurities: Residual Solvents" CPMP/ICH/283/95.

Despite of the above, it is worth noting that the scale up of the known methods for commercial production can lead to an increase of the amount of the genotoxic impurities due to different experimental conditions for the reaction, the isolation and drying of the salt. Moreover, the genotoxic impurities level can vary during the time, depending on the amount of residual solvent and of the locally free methanesulfonic acid. Moreover the potential presence of these genotoxic impurities obliges the salt manufacturers to check, in different phases of the process and storage of the products, the amounts of such impurities. This is a very expensive and cumbersome control because of the number of analyses requested due also to the sophistication of the methods.

In view of the above and even increasing strictness of the recommendations issued by the Regulatory Authorities, it is of main interest to provide a new process for the production of ralfinamide methanesulfonate and the respective R-enantiomer, which allows further improvements of both the toxicological profile and the economical aspects of the production of these drugs, whereby the methanesulfonate salts of ralfinamide (Ia) and the respective R-enantiomer (I'a) are obtained in a solid form which is substantially free from impurities having genotoxic effects and residual solvents, such as lower alkanols and lower alkyl acetates, known as potential precursors thereof.

According to this invention it is provided a new process which allows large scale production, and/or purification of the methanesulfonate salt of ralfinamide (Ia), or the respective R-enantiomer (I'a), in high yields which is substantially free from impurities having genotoxic effect, such as MMS, EMS and IMS, and residual solvents known as potential precursors thereof due to their reactivity toward the methanesulfonic acid to form the respective esters.

The salt formation and/or purification process of this invention, when applied to batches of ralfinamide and its R-enantiomer, that are produced according to the methods described in WO 2007/147491 and WO 2009/074478, allows obtaining the methanesulfonate salt of the above named substances which, besides having the expected high purity degree with respect to the bis-benzylated side-products interacting with the cytochromes of the CYP 450 system, are substantially free from impurities having genotoxic effect and residual solvents known as potential precursors thereof.

This invention relates to a new process for the production and/or purification of the salt of the compound (S)-2-[4-(2-fluorobenzyloxy) benzylamino]propanamide, i.e. ralfinamide (Ia).

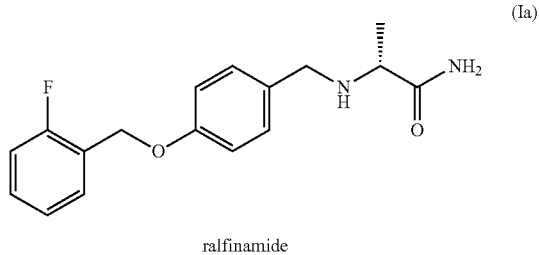 [SMILES: C[C@@H](NCc1ccc(OCc2ccccc2F)cc1)C(N)=O]

ralfinamide or the respective R-enantiomer (I'a), with methanesulfonic acid in high yields and very high enantiomeric and chemical purity in the form of the crystalline anhydrous polymorph identified as form A, exhibiting an X-ray powder diffraction pattern (PXRD) having essentially characteristic peaks expressed in degree 2θ at:
6.93; 7.80; 9.66; 11.38; 12.04; 13.02; 13.82; 15.60; 16.36; 16.62; 17.52; 17.83; 18.75; 19.35; 19.70; 20.34; 20.69; 21.20; 22.69; 22.95; 23.23; 23.50; 24.80; 25.24; 25.8056; 26.01; 27.84; 28.07; 28.55; 29.16; 29.82; 30.77; 31.50; 31.95; 32.38; 33.37; 33.96; 34.61; 34.95; 36.02; 36.46; 37.38; 38.04; 39.66 wherein said salt is substantially free from impurities having genotoxic effect and residual solvents known as potential precursors thereof, characterised in that:
(i) the salt is produced, or purified by crystallization from a solution in a solvent selected from;
a) water,
b) a mixture of water with acetone or an aliphatic ketone of 4-5 carbon atoms, and
c) acetone, an aliphatic ketone of 4-5 carbon atoms or a mixture thereof; or (ii) the solid salt containing an undesired amount of impurities having genotoxic effect and/or of the residual solvents known as potential precursors thereof, is slurried with a solvent selected from:
(a) water,
(b) a mixture of water with acetone or an aliphatic ketone of 4-5 carbon atoms,
(c) acetone, an aliphatic ketone of 4-5 carbon atoms or a mixture thereof; or
(iii) the solid salt containing an undesired amount of impurities having genotoxic effect and/or of the residual solvents known as potential precursors thereof is exposed to air stream having high degree of relative humidity at a temperature and for a time sufficient to allow the removal of the above said impurities having genotoxic effect and/or of the residual solvents known as potential precursors thereof and,
(iv) when the resulting crystalline form of the so obtained salt is the crystalline hemihydrate pseudopolymorph form, identified as form H, exhibiting an X-ray powder diffraction pattern having essentially characteristic peaks expressed in degree 2θ at:
4.09; 7.09; 10.06; 11.64; 12.34; 16.38; 17.00; 17.47; 19.26; 20.11; 20.63; 21.34; 21.97; 23.35; 23.86; 24.12; 25.29; 27.15; 27.61; 28.02; 28.74; 29.62; 30.02; 30.51; 31.29; 31.81; 32.89; 33.35; 33.93; 35.10; 35.39; 35.62; 36.22; 38.91; 39.50;
or a mixture thereof with the crystalline anhydrous polymorph form A,
(v) said hemihydrate pseudopolymorph form H or the above said mixture thereof is wholly converted into the crystalline anhydrous polymorph form A by removal of the crystallization water on heating.

According to a preferred embodiment of this invention, a process for large scale production or/purification of ralfinamide methanesulfonate salt, or its R-enantiomer, in very high yields and very high enantiomeric and chemical purity in the form of the crystalline anhydrous polymorph form A, wherein said salt is substantially free from impurities having genotoxic effect and residual solvent known as potential precursors thereof, is characterised in that;
(i) the salt is produced or purified by crystallization in a solvent selected from:
a) water,
b) a mixture of water with acetone or an aliphatic ketone of 4-5 carbon atoms; or
(ii) the solid salt containing an undesired amount of impurities having genotoxic effect and/or of residual solvents known as potential precursors thereof, is slurried with a solvent selected from:
a) water.
b) a mixture of water with acetone or an aliphatic ketone of 4-5 carbon atoms; or
(iii) the solid salt containing an undesired amount of impurities having genotoxic effect and/or of residual solvents known as potential precursors thereof is exposed to air stream having high degree of relative humidity at a temperature and for a time sufficient to allow the removal of the above said impurities having genotoxic effect and/or of the residual solvents known as potential precursors thereof;
(iv) wherein the resulting crystalline form of the so obtained salt is the crystalline hemihydrate pseudopolymorph form identified as form H, exhibiting an X-ray powder diffraction pattern having essentially characteristic peaks expressed in degree 2θ at:
4.09; 7.09; 10.06; 11.64; 12.34; 16.38; 17.00; 17.47; 19.26; 20.11; 20.03; 21.34; 21.97; 23.35; 23.86; 24.12;

25.29; 27.15; 27.61; 28.02; 28.74; 29.62; 30.02; 30.51; 31.29; 31.81; 32.89; 33.35; 33.93; 35.10; 35.39; 35.62; 36.22; 38.91; 39.50:

or is a misuse thereof with the crystalline anhydrous polymorph form A; and (v) said hemihydrate pseudopolymorph form H or the above said mixture thereof is wholly converted into the crystalline anhydrous polymorph form A by removal of the crystallization water on heating.

In this description and claims the expression "impurities having genotoxic effect" identifies ($C_1$-$C_5$)alkyl methanesulfonates, preferably, methyl methanesulfonate (MMS), ethyl methanesulfonate (EMS), and isopropyl methanesulfonate (IMS). One or more ($C_1$-$C_5$)alkyl methanesulfonates may be present as impurities in the methanesulfonate salt of the active substance.

The expression "residual solvents known in potential precursors thereof" identifies ($C_1$-$C_5$)alkanols, or their esters with a lower alkanoic acid, preferably methanol, ethanol and isopropanol, or their acetates. One or more ($C_1$-$C_5$)alkanol may be present as residual solvents in the active methanesulfonate salt of the active substance.

The expression "substantially free from impurities having genotoxic effect" in this description and claims means that the amount of each of the ($C_1$-$C_5$)alkyl methanesulfonate, preferably, each of MMS, EMS and IMS, determined through the analytical method herein described is lower than 0.05 ppm (LOD) with respect to the methanesulfonate salt of the active substance.

Analogously, the expression "substantially free from residual solvents known as potential precursors thereof" (i.e. precursors of the genotoxic impurities) means than the amount of each of the ($C_1$-$C_5$)alkanols residual solvents, in particular ($C_1$-$C_3$)alkanols, such as methanol, ethanol and isopropanol, and/or the esters thereof with lower alkanoic acids (e.g., ethyl acetate), is lower than 6 ppm (LOD) with respect to the methanesulfanate salt of the active substance, as determined according to the analytical method herein described. The expression "produced or purified by crystallization from a solution in a solvent" means that the salt is obtained as a crystalline solid product from a solution in the selected solvent wherein the salt forming reagents or the salt itself have been previously completely dissolved.

The expression "slurried with a solvent", "slurring procedure", means that the solid salt is suspended in a selected solvent as a heterogeneous mixture and is submitted to stirring or shaking or other equivalent treatment.

Formation or Crystallization of the Salt (i)

a) Use of Water

Surprisingly, it has been found that, anhydrous ralfinamide methanesulfonate or its R-enantiomer crystalline form A having the characteristics defined above can be directly obtained by crystallization from water when an aqueous solution, of ralfinamide methanesulfonate or its R-enantiomer is slowly concentrated by evaporation at room temperature.

Under these conditions crystals grow in form of colourless needles. Powder X-Ray Diffraction (PXRD) analysis, giving a pattern fully compatible with FIG. 1, confirms that the obtained crystals have form A structure. Thermogravimetric analysis (TGA) performed on the grown crystals shows no weight loss. Single crystal X-ray diffraction (SCXRD) analysis, that allows the direct experimental determination of all the crystallographic parameters defining the crystalline state of a compound (i.e. unit cell dimensions, space group and position of all the atoms relative to the origin of the unit cell), has been performed on a crystal selected in the grown batch. The determined unit cell space group and calculated crystal density are reported in Table 1. SCXRD analysis confirms that the crystal structure of the salt consists of the packing of protonated ralfinamide moieties (protonation occurs on the aminic nitrogen atom) and methanesulfonate anions without other molecules. FIG. 2 shows the molecular structure, confirming the S absolute configuration of the ralfinamide moiety. FIG. 3 shows the crystal packing which is mainly determined by hydrogen bonds involving hydrogen atoms of the aminic and amidic groups and oxygen atoms of the sulfonate group. Each ralfinamide moiety is bonded to four different sulfonate groups, two by the aminic and two by the amidic group respectively, whereas the oxygen atoms of each sulfonate group are bonded to four ralfinamide moieties, in two cases via the aminic group and in the other two via the amidic one. In this way anions and cations are intercalated along the b axis forming chains in which the ralfinamide moieties assume a herringbone arrangement. The chains are then further linked along the c axis, forming molecular planes perpendicular to the a direction. Adjacent planes are reversed, in order to maximize their packing efficiency determined by Van der Waals interactions. The terminal aromatic ring of the ralfinamide moiety was found to be disordered on two possible orientations (tilted each other of about 39 degrees) at a different probability level (65 and 35% respectively). For each orientation the fluorine atom is disordered at the same probability level (50%) over two positions, corresponding to a rotation of 180 degrees around the C11-C12 bond of the whole ring. Since the results of a SCXRD analysis are limited to, as the name implies, the one crystal placed in the X-ray beam, their conversion into a PXRD diagram, provides the way to compare them with the results obtained on a large group of crystal (for example the batch from which the crystal has been selected). This conversion is made possible by different computer programs by using the crystallographic parameter's routinely determined in the SCXRD experiment. This has be done by the software POWDER CELL (W. Klaus and G. Nolze, J. Appl. Cryst. (1996) 29; 301) and the results are graphically displayed in FIG. 4 compared with the experimental pattern recorded for a typical sample of form A (powder). The full agreement of the calculated and experimental peak positions clearly indicates that the results of SCXRD analysis are representative of form A.

Karl Fischer (K F) analysis of the form A crystals obtained as described above shows a 0.1% (w/w) content of water, consistent with no loss of weight of TGA (FIG. 11) and thus with the anhydrous nature of the crystals. Differential Scanning Calorimetry (DSC) (FIG. 11) shows one endotherm at 243.1±0.2° C. ($\Delta H=132.1\pm4.5$ J/g).

The crystals are characterized by solid state Cross Polarization Magic Angle Spinning Nuclear Magnetic Resonance (CP/MAS NMR) spectra (M. R. M. Palermo de Agular, A. L., Gemal and R. Agular da Silva San Gil, Quimica nova, 22(4) (1999).

The anisotropics in the local fields of the protons broad the $^1$H CP/MAS NMR spectra of this form A in such a way that no spectra lines could be resolved and become significative.

On the contrary the $^{13}$C CP/MAS NMR spectrum is well defined in the aliphatic part where narrow signals of resonances for MeC-13 (16.6 ppm), C-15 (39.0 ppm), C-12 (50.8 ppm), C-13 (57.0 ppm) and C-7 (63.5 ppm), while aromatic carbons signals are fairly wide with an width-line up to 800 Hz. Moreover, the resonances of the aromatic quaternary carbons C-11, C-4 and C-8 are found at 158.1, 158.2 and 170.0 ppm, respectively, and the amidic carbon show three broad signals a 193.0, 197.0 and 203.0 ppm.

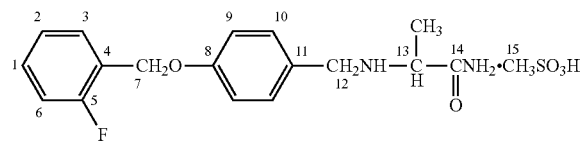

The crystalline structure of ralfinamide methanesulfonate obtained through slow concentration by evaporation of an aqueous solution of the salt has been conventionally identified as form A polymorph.

The PXRD of the methanesulfonate salt of the R-enantiomer of ralfinamide obtained according to the same procedure described above are consistent with those determined on the ralfinamide methanesulfonate form A polymorph.

PXRD analysis performed on samples of ralfinamide methanesulfonate and the respective R-enantiomer prepared according to the prior art methods (WO 2006/027052, WO 2007/14749 and WO 2009/074478) confirms that these samples exhibit the same characteristic parameters as the methanesulfonate salts obtained according to the procedure described above and, therefore, they can be assigned the form A polymorph structure. According to a further aspect of this invention, it has been found that a new crystalline pseudopolymorph form, identified as hemihydrate form H, of ralfinamide methanesulfonate as well as the respective R-enantiomer may be obtained in large amount by crystallization of the salt from water in the presence of form H seed crystals or by reaction of the respective free-base with methanesulfonic acid in water ("salt formation") followed by salt crystallization, from the salification medium, promoted by addition of form H seed crystals.

The hemihydrate pseudopolymorph form H, which, does not contain lower alkanols residual solvents as well as genotoxic lower alkyl sulfonates impurities, is useful per se because of its typical pharmaceutical properties and because it can be quantitatively converted, by removal of water on heating, into the corresponding form A, which, in turn, is solvent and genotoxic impurities free. The conversion of the hemihydrate pseudopolymorph form H into anhydrous polymorph form A by removal of the crystallization water may be carried out by heating at 95° C.-120° C., preferably at 98° C.-102° C., under reduced pressure until constant weight. As an example, by operating at a pressure of 20 mmHg and a temperature of 110° C. the conversion of form H to form A crystals is completed in about four hours.

Form H crystals can also be used as seed to induce formation of form H crystals from saturated aqueous solutions of the methanesulfonate salt of ralfinamide or its R-enantiomer.

The formation and crystallization procedures in water may be carried out according to the common methods known to the skilled expert in the art where water is used as solvent in the formation or crystallization of salts of basic APIs with pharmacologically acceptable acids.

In view of the amidic nature of ralfinamide and its R-enantiomer, a precautionary condition is that the aqueous solution containing the salt is not exposed at a temperature over 70° C. for a long time (e.g. more than 2 hour for a solution where the w/w ratio between water and the salt is varying from 3:1 to 10:1). In order to avoid hydrolysis of the amidic functional group.

The use of the crystallization technology by employing water as the sole solvent in the purification of the above mentioned methanesulfonate salts affords high yields of hemihydrate crystals form H, free from genotoxic impurities and residual solvents known as potential precursors thereof. According to a preferred method to carry out the crystallization procedure, a mixture of water and (S)-2-[4-(2-fluorobenzyloxy)benzylamino]propanamide methanesulfonate or its R-enantiomer (in a w/w ratio from 3:1 to 10:1) is heated up to 65° C. under mechanical stirring and under nitrogen. The solution is filtered.

Form B seed crystals are added to the solution and kept under stirring at 55° C.-65° C. for up to one hour. The mixture is cooled under stirring to 5° C.-15° C. gradually in 2-6 hours, filtered, washed with chilled purified water to yield a wet product which is dried as 20° C.-40° C. to provide the product of the title, in 70 to 90% yield, having higher HPLC purity, with respect to that of the starting salt. Residual solvents: less than 6 ppm (LOD). Alkyl methanesulfonates content each of MMS. EMS and IMS lower than 0.05 ppm (LOD).

According to a preferred method to carry out the procedure defined above as "salt formation", the formation of ralfinamide methanesulfonate form H or its R-enantiomer is carried out by using water as the sole solvent in which the free base and the methanesulfonic acid are contacted in substantially equimolecular proportion. According to a more preferred method, methanesulfonic acid is added to a suspension or emulsion of the free base in water. Generally 50-70 percent of the stoichiometric amount of the acid is initially added. Surprisingly, under these conditions a solution is obtained despite the free base is almost insoluble in water. The remaining portion of methanesulfonic acid to complete the stoichiometric amount required for the salification, or a small excess or defect (in both cases of up to 3 molar %), is subsequently added to the obtained solution. Ralfinamide free base and its R-enantiomer are practically insoluble in water also at 100° C., (e.g. when a suspension of ralfinamide in an amount of water sufficient to form a final mixture of water and salt in a w/w ratio from 3:1 to 10:1 is heated at 80° C.-95° C., an oily phase separates). Therefore, it would not be possible to apply prior to the addition of the acid, any purification method implying the treatment of a solution of the free base with active charcoal or inert powder followed by filtration to remove small particles and/or impurities. However, according to the process of this invention, it has been surprisingly found that the addition of methanesulfonic acid in an amount significantly lower than the stoichiometric amount to a heated suspension of ralfinamide free base or its R-enantiomer in water produces a complete solution of it having high stability, which allows the purification of the obtained solution through filtration or contact with a solid absorption medium. The complementary amount of acid may be added soon after this treatment of the solution, preferably, after lowering the temperature of the mixture below 70° C.

Then, form H seed crystals prepared, for example, with slurry technology (see Example 3) are added to the solution in order to control the start up of the crystallization and to promote the precipitation of the hemihydrate pseudopolymorph form H and preventing the crystallisation of the anhydrous polymorph A form. After the seed crystals are added to the salt solution, the temperature is further lowered in a controlled predetermined way.

According to a more specific representative example, the hemihydrate pseudopolymorph form H of ralfinamide methanesulfonate or its R-enantiomer is prepared by adding methanesulfonic acid, in a quantity of about 50-70% of the stoichiometric amount required, to a suspension of ralfinamide base at about 70° C.-90° C. The solution thus obtained is treated with active charcoal and filtered. Then, the complementary quantity (30-50%) of methanesulfonic acid is added by keeping the temperature at about 60° C.-70° C. Addition of hemihydrate pseudopolymorph H seed crystals to the solution kept at 50-65° C. provokes the start up of the crystallization, which is completed by gradually lowering the temperature to about 5° C.-15° C. to complete the crystallization of the crystalline hemihydrate pseudopolymorph form H of the salt.

The solid is collected by filtration, dried at about 40° C.-50° C. to provide a solid powder containing 2.2% (by weight) of water, as determined by K.F. analysis, which corresponds to 1 mole of water for 2 moles of ralfinamide methanesulfonate (or its R-enantiomer).

A further preferred alternative method (reverse addition method) consists of the addition of ralfinamide or its R-enantiomer to an aqueous solution containing an equimolecular (or a small excess of defect up to 3 molar %) amount of methanesulfonic acid in an amount of purified water sufficient to form a mix turn of water and salt in w/w ratio from 3:1 to 10:1 at room temperature followed by heating the thus obtained heterogeneous mixture up to 65° C.-70° C. to provide a solution. Form H seed crystals, prepared as in Example 3, are added to the thus obtained solution and kept under stirring at 60° C.-65° C. The mixture is cooled under stirring to 5° C.-15° C. gradually in 3-6 hours and then the crystalline product is filtered, washed with chilled purified water, to yield a wet product which is dried at 40° C.-50° C. at ambient pressure to provide ralfinamide methanesulfonate form H in 80-90% yield Residual solvents content: less than 6 ppm (LOD). Alkyl methanesulfonates content: MMS, EMS and IMS lower than 0.05 ppm (LOD) (see Example 19).

PXRD analysis (FIG. 5) performed on hemihydrates pseudopolymorph form H crystals produced by slurry, crystallization or formation technology show the same pattern, confirming that they have the same crystalline structure.

The structure of a single form H crystal obtained by crystallization from a saturated ralfinamide methanesulfonate water solution after addition of a few seed form H crystals, has been investigated by SCXRD. The unit cell value, space group and calculated crystal density parameters are reported in Table 2, in comparison with those of form A (see example 7).

SCXRD analysis confirms that the form H crystal structure contains crystallisation waters in a 1:2 ratio with ralfinamide methanesulfonate, and no other impurity or residual solvent. The molecular structure, involving a water molecule and two symmetry independent units for both the protonated ralfinamide moieties (protonation occurs on the aminic nitrogen atom) and the methanesulfonate moieties, is shown in FIG. 6. The structure confirms the S absolute configuration of the ralfinamide moiety. The crystal structure consists of the packing of protonated ralfinamide moieties, methanesulfonate anions and water in ratio 2:2:1. The crystal packing (FIG. 7) is mainly determined by a tetrahedral hydrogen bond system involving the water molecule, bonded to two ralfinamide moieties and two methanesulfonate groups. In this system each water molecule acts as double donor (with respect to two oxygen atoms of the anions) and double acceptor (with respect to two hydrogen atom of the amidic groups of ralfinamide molecules). Each ralfinamide moiety is bonded to three different sulfonate groups, two by the aminic and one by the amidic group respectively, and to a water molecule (by the amidic group). At the same time the oxygen atoms of each sulfonate group are bonded to three ralfinamide moieties, in two cases via the aminic group and in the other via the amidic one, and a water molecule. This complex hydrogen bond system leads to the formation of 2D molecular sheets parallel to the ab plane, in which the ralfinamide moieties, viewed along the a axis, assume an interdigitated double-comb arrangement. FIG. 7 evidences the crucial role of water in determining the high packing efficiency of hemihydrate pseudopolymorph form H, implying the absence of disorder and a significant increase of the crystal density (4%) with respect to the anhydrous form A. The comparison of the experimental PXRD pattern typical of form H with the one calculated with POWDER CELL on the basis of the crystallographic parameters determined in the SCXRD experiment is shown in FIG. 8. The full agreement of the calculated and experimental peak positions clearly indicates that the results of SCXRD analysis are representative of form H.

The thus obtained crystals are further characterized by DSC, TGA $^1$H-NMR in $CD_3CN$, and $^1$H and $^{13}$C, Cross-Polarization Magic-Angle Spinning, Nuclear Magnetic Resonance (CP-MAS NMR) (see Example 10).

TGA analysis (FIG. 12) shows a loss of 2.14% of weight at 95° C. fully consistent with the presence of one molecule of water for two molecules of ralfinamide methanesulfonate.

The water loss is consistent with the K.F. analysis.

DSC (FIG. 12) shows two endothermic peaks; the product shows a first endotherm at 95.1±2.0° C. ($\Delta H=91.4\pm3.3$ j/G) and a second endotherm at 241.3±0.3° C. ($\Delta H=116.7\pm5.1$ J7g). (See Example 20)

The crystals are characterized by solid state CP/MAS NMR spectra (see FIG. 10)

The $^1$H CP/MAS NMR spectrum of the form H is not significative for the width-line of the signals, hut at 1.76 ppm there is a sharp resonance which can be attributed to water.

The $^{13}$C CP/MAS NMR spectrum shows, in the aliphatic region, some sharp signals between 13.5 and 61.2 ppm; moreover, the aromatic carbons resonances in the range from 111.3 to 133.1 ppm show a good degree of resolution (width-line about 200-250 Hz). The spectrum reveals the aromatic quaternary carbons signals at 156.8 and 166.05 ppm and a series of resonances, ascribed to the amidic carbon, between 182.0 and 207.0 ppm.

The $^{13}$C CP/MAS NMR spectra of the form A and H mainly differ from the number of lines and the chemical shifts for most of the carbons atoms. In the aliphatic region (10-70 ppm), the A form spectrum shows a lower number of resonances, with similar amplitude, while the H form reveals sharp differently structured resonances: C-15 is splitted in two lines (39.05 and 40.2 ppm), C-12 is shifted to high fields (44.6 ppm) respect to the A form (50.8 ppm), depending on their different orientation with respect to the external magnetic field. Indeed, the chemical shielding anisotropy gives rise to frequency shifts with an orientation dependence.

Moreover, in the aromatic region, the form A shows, for the protonated aromatic carbons, a lower number of resonances, but with a four fold width-line (up to 800 Hz) respect to the form H which has sharp resonances (width-line about 200-250 Hz). Also the signals of the amidic carbon of form H are increased as numbers and sharpness.

The comparison of data of ralfinamide methanesulfonate form A and form H show that they have two different crystalline structures where the form H appears to be more ordered with respect to the form A.

To verify whether the hemihydrate pseudopolymorph crystalline form H presented by the methanesulfonate of ralfinamide and its R-enantiomer can be obtained also for salts with acids other than methanesulfonic acid, the ralfinamide salt with hydrochloric acid has been prepared by using water as the solvent.

The hydrochloride salt of ralfinamide, prepared by addition of hydrochloric acid to a suspension of ralfinamide fee base in water, isolation of the salt by filtration and drying at room temperature until constant weight (Example 13) does not show any presence of water in the crystalline structure. This result is confirmed both by K.F. analysis and by the DSC and TGA analyses. The PXRD patterns of wet and dry sample are the same (FIG. 14). The hydrochloride salt, which has never been disclosed in the prior art, differs from the methanesulfonate salt as no hydrated form is formed also under conditions which favour the formation of the hemihydrate form of methanesulfonate salt.

b) Use of a Mixture of Water with Acetone or an Aliphatic Ketone of 4-5 Carbon Atoms Hemihydrate pseudopolymorph form H crystals may be obtained also by formation or purification by crystallization of ralfinamide methanesulfonate or its R-enantiomer from a mixture of water with acetone or an aliphatic ketone of 4-5 carbon atoms. This method is particularly suitable for purifying preparations of the methanesulfonate salt of ralfinamide or its R-enantiomer containing an undesired amount of genotoxic impurities such as lower alkyl methanesulfonates and/or of residual solvents known as potential precursors thereof, like (C1-C5) alkanols, in particular (C1-C3) alkanols. A useful mixture of water with acetone or an aliphatic ketone of 4-5 carbon atoms, may consist in a mixture of two or more of said solvents in any proportion, although a two solvent system is preferred.

The proportion of water to the ketone solvent may vary within a wide range, compatibly with the reciprocal solubility at the operative temperature. The same precautionary conditions applied for the use of water as described above under paragraph (a) are advantageously adopted here.

For example; mixtures water/acetone from 5:95 to 30:70 (w/w), water/methyl ethyl ketone from 5.95 (w/w) to 25.75 (w/w) are advantageously employed.

In crystallization operation the operative temperature is usually determined by the boiling point of the mixture.

The above mentioned mixtures of water with acetone or a ($C_4$-$C_5$)aliphatic ketone can be employed also as solvents for the formation of the salts by reaction of the ralfinamide free base, or its R-enantiomer, with methanesulfonic acid according to the procedure described above for the use of water as the solvent.

The crystalline form resulting with the use of the aqueous mixtures as the solvent for the formation or purification of the methanesulfonate salt may be either form H, or form A or a mixture thereof, depending on the proportion of the components of the solvent mixture and the conditions applied during the formation, or crystallization operation. In any case, when form H or a mixture of form H and form A crystals is obtained (which is substantially free from the above defined impurities having genotoxic effect and the residual solvents which are their potential precursors) said mixture can be wholly transformed into the anhydrous crystalline form A by submitting it to the water removal procedure described above.

c) Use of Acetone or an Aliphatic Ketone of 4-5 Carbon Atoms

As a further aspect of this invention, it has been found that by using ketone solvents, such as acetone, an aliphatic ketone of 4-5 carbon atoms or a mixture thereof, in the formation or purification by crystallization of the methanesulfonate salts of ralfinamide or its R-enantiomer, the obtained salts are substantially free not only from genotoxic impurities and the residual solvents, known as precursors thereof, but also from impurities deriving from the interaction of the active substance with the ketone solvent. These results are unexpected, being well known the reactivity of aliphatic ketons towards substances which, like ralfinamide, contain a secondary amino group.

When acetone, an aliphatic ketone of 4-5 carbon atoms or a mixture thereof is used as the solvent and methanesulfonic acid is slowly added to the solution formed by dissolving the fee base in the solvent (preferably, in a ratio front 1:3 to 1:10 (w/w)) at 50° C.-80° C. (depending on the solvent), colourless crystals separate from the mixture. After cooling, filtration of the mixture and drying of the crystals, the salt is obtained in high yield.

As an example, crystals of ralfinamide methanesulfonate produced in 50-100 kg pilot batch in acetone, alter drying, show a residual acetone content in a range from 800 to 1500 ppm, while lower alkanols (methanol, ethanol and isopropanol), as well as lower alkyl esters (ethylacetate), are found to be absent (below the LOD), even when any such lower alkanol solvent has been used in the previous steps of the process. Moreover, GC/MS analysis indicates that lower alkyl methanesulfonates ($ROSO_2CH_3$ where R=$CH_3$, $C_2H_5$, $C_3H_2$, etc.) are below the LOD (see Example 19).

The salts at the solid state obtained according to this procedure are characterized by PXRD. DSC and TGA and $^1H$ and $^{13}C$ CP-MAS, confirming that the obtained form is the anhydrous form A. Moreover, PXRD and DSC comparative analysis show that the salts of ralfinamide with methanesulfonic acid, when formed in acetone, a ($C_4$-$C_5$) aliphatic ketone or a mixture thereof, have the same anhydrous crystalline form (form A) of the salts prepared by the prior art methods.

The same solvents mentioned hereinabove may be used for the purification of batches of ralfinamide methanesulfonate or its R-enantiomer by crystallisation, when these salts contain undesired amounts of the above mentioned genotoxic imparities and/or residual solvents which are potential precursors thereof.

Slurring of the Solid Salt (ii)

According to a typical stoning procedure (ii), a batch of crystalline anhydrous polymorph form A of the methanesulfonate of ralfinamide or its R-enantiomer in solid form, containing an undesired amount of the above defined impurities having genotoxic effect and/or of the residual solvents known as potential precursors thereof is stirred at a temperature varying from 10° C. to 40° C. with an amount of water or a mixture of water and acetone or an aliphatic ketone of 4-5 carbon atoms, which is sufficient to form a suspension of the solid crystals into said solvent, font is not capable to dissolve them to an appreciable extent at the operation temperature, for a period of time which depends on the amount of water employed and the selected operation temperature and, in general, ranges from 4 hours to 48 hours. At the end of the stirring operation the crystalline suspension is allowed to stand at room temperature and the solid is filtered and dried at room temperature in vacuo yielding a batch of hemihydrate pseudopolymorph form H crystals, as confirmed by PXRD analysis (FIG. 5).

The proportion of water to the ketone solvent may vary within a wide range compatibly with the reciprocal solubility at the operative temperature in the same way as described above for the formation and crystallisation operations.

The same slurring procedure may be applied to purify the solid methanesulfonate salt of ralfinamide or its R-enantiomer by using acetone, a ($C_4$-$C_5$) alphatic ketone or a mixture thereof in the place of water or a mixture of water with acetone or an aliphatic ketone of 4-5 carbon atoms. The conditions are essentially the same as those described above. The purified salt presents the crystalline anhydrous polymorph form A.

Exposure to Air Stream having High Degree of Relative Humidity (iii)

As an alternative procedure to the slurring with water for converting anhydrous form A crystals containing undesired amounts of genotoxic impurities and/or of the residual solvents known as potential precursors thereof into the corresponding hemihydrate pseudopolymorph form H substantially free from the genotoxic impurities and/or the residual solvents known as potential precursors thereof, the capability of anhydrous form A crystals to uptake water from air having high degree of relative humidity may be exploited. For example, full conversion of form A crystals into the corresponding hemihydrate pseudopolymorph form H crystals can be achieved by keeping a batch of ralfinamide methanesulfonate or its R-enantiomer form A crystals under air stream having relative humidity higher than 65% at a temperature from 5° C. to 30° C. for a period of time which may vary from days to weeks or months, depending on the relative humidity degree and the temperature.

If the crystals resulting from slurry or exposure of the solid salts to an humid air stream as described above consist of a mixture of the form A and form H crystals, said mixture can be fully transformed into a hatch of form A crystals by submitting it to water removal as described above.

In view of the above description, one aspect of this invention consists in providing a new method for the production or the purification of the methanesulfonate salt of ralfinamide or its R-enantiomer. The method foresees (i) formation and/or crystallization, from water, acetone, an aliphatic ketone of 4-5 carbon atoms or mixtures thereof with water, (ii) slurring with (a) water, (b) a mixture of water with acetone or an aliphatic ketone of 4-5 carbon atoms, (c) acetone, an aliphatic ketone of 4-5 carbon atoms or a mixture thereof or (iii) exposure to an air stream, having high degree of relative humidity, and when the obtained product consists as a whole or in part of hemihydrate pseudopolymorph form H crystals, converting said product into anhydrous form A crystals by submitting it to water removal, said method being characterized in that the salt is obtained in a form which is substantially free from impurities having genotoxic effect and/or residual solvents known as potential precursors thereof.

According to a further aspect of this invention the use of water as the sole reaction solvent embodies a preferred method for the manufacture of the methanesulfonate salt of ralfinamide or its R-enantiomer from the corresponding free base and methanesulfonic acid, as it provides the salts of ralfinamide or its R-enantiomer with the methanesulfonic acid with high chemical and enantiomeric purity, substantially free from genotoxic impurities and residual solvents knows as potential precursor thereof. According to a more preferred aspect of this invention, the new method involves a first step whereby the salt is obtained in the form of a hemihydrate pseudopolymorph (form H) and a second step whereby the water is removed from the hemihydrate with transformation into the crystalline polymorph A.

Polymorph A is the crystalline form of the methanesulfonate salt of ralfinamide or its R-enantiomer obtained according to the methods described in the prior art, which have been suitably used for all pharmacological and clinical applications as reported in WO 2009/109334.

The new hemihydrate pseudopolymorph form H of ralfinamide methanesulfonate and its R-enantiomer is a useful intermediate for obtaining the crystalline polymorph A, substantially free from genotoxic impurities and residual solvents known as potential precursors thereof. This use of the hemihydrate pseudopolymorph H obtained by using water as the solvent is particularly advantageous from the economical and pharmaceutical standpoint for large scale preparations of polymorph A for clinical applications.

The advantages of the new process based on the use of water as the solvent concern purity, safety and cost reduction.

In fact, no by-products and genotoxic impurities are formed by reaction of ralfinamide or its R-enantiomer free base with methanesulfonic acid in water. Due to the absence of organic solvents, the solid form of the methanesulfonate salt of ralfinamide or its R-enantiomer is not contaminated by said impurities.

The safety major potential problems, which are generally related to the use of organic solvents because of their flammability and the explosive property when vapours are in contact with air, are avoided with the use of water as solvent for the production and/or purification of the methanesulfonate salt according to the process of this invention. It is worth noting that organic solvents which do not show the above properties, such as halogenated solvents, are not desirable for their toxicity.

The reduction of costs is evident as purified water is the less expensive solvent. Analytical problems are reduced because of the absence of alkylmethanesulfonate impurities.

The cost of analysis is reduced because there is no need to does genotoxic impurities at ppm level as they are not formed if the process is carried out in water.

Additional advantages are related to the fact that, even if lower alkanols are used as solvents in the synthesis steps preceding the salt formation, the use of water as the solvent for the salt formation and/or purification allows complete elimination of any actual or potential risk of contamination of the final product by lower alkyl methanesulfonate impurities.

Pharmaceutical Features of Ralfinamide (and its R-Enantiomer) Methanesulfonate Form H Drug Substance and Drug Products It is recognized that different polymorphic forms of a solid can differ from each other with respect to many physicochemical properties such as solubility and dissolution, apparent and true densities, crystal shape, compaction behavior, flow properties and solid state stability (Florence A. T. et al. Physiochemical Principles of Pharmacy, 1994 The MacMillan Press London).

The physicochemical profile of the pseudopolymorph ralfinamide methanesulfonate hemihydrate (form H) compared with that of the anhydrous compound (form A), shows significant advantages in the design and development of the solid dosage forms.

They are summarized as follows:
higher stability in humid or wet conditions,
compressibility and consolidation during tableting,
less intraparticulate porosity, and
slower dissolution rate.

The water absorption of ralfinamide form A when exposed to humid or wet conditions clearly points out that the application of wet processes such as moist granulation and aqueous film coating or the simple exposition to thigh humidity should be avoided or limited carefully if the anhydrous drug substance must be kept in the finished drug product. The use of the hydrated drug substance allows to avoid the problems of water absorption and recrystallization. specifically, the hydrate form H permits to use the wet granulation which is a robust process with the advantages of (i) imparting flowability to the formulation, (ii) reducing elasticity problems, (iii) improving wettability when the tablet surface is coated with hydrophilic polymers, and (iv) reducing potential segregation binding drug with excipients (Dilip M. Parikh (ed.), Handbook of Pharmaceutical Granulation Technology, Mercel Dekker, New York 1997).

The water present on the hydrated compound is also useful for technological operations in manufacturing of a final dosage form such as tablets. The incorporation of water molecules changes the free surface energy and determines the filling of the intraparticulate voids, reducing the porosity of the particles. As a result of increasing compression force during the tabletting, a considerable frictional heat is generated at the points of contact and the presence of water acts as an agent facilitating the tablet consolidation at the particle contact points. The final effect is an easier compression process.

Film coating involves the application of a polymer film to the surface of the tablet with a negligible increase of tablet size. The coating of the tablets can be designed to make the swallowing of the dosage form easier as well as to mask the unpleasant taste of drug substance. As regulatory pressure relating to health, safety and environmental protection has grown, the use of aqueous solutions is becoming mandatory. During the initial stages of the aqueous film-coating process, the aqueous droplets impinge onto uncoated surface and simultaneously penetrate into the tablets. The water penetrating inside does not interact with the active substance because the hemihydrate form is a well-defined pseudopolymorphic form (James W. McGinity (ed.)—Aqueous Polymeric coating for Pharmaceutical Dosage Forms —Mercel Dekker, New York 1997).

In addition, the finished product containing the hemihydrate drug packaged in blisters or bottles and stored at warm and humid conditions does not change the water content for all the period of shell-life.

Another important factor is that, when the particles are subjected to intense friction like milling or mixing operations, the presence of water on the particles reduces the chance of any complicating electrostatic effect by providing a conducting path for charge dissipation. The resulting advantage of ralfinamide (and its R-enantiomer) methanesulfonate hemihydrate pseudopolymorph form H is an easier development of the oral solid formulation.

Intrinsic dissolution rate is characteristic of each solid compound in a given solvent under fixed hydrodynamic conditions. The knowledge of this value helps in predicting if absorption would be dissolution rate-limited. The Intrinsic Dissolution Rate (IDR) measurement of ralfinamide methanesulfonate form A and H was performed according to USP General Chapter <1087>.

The results of IDR measurement are shown below:

| Ralfinamide methanesulfonate | Intrinsic Dissolution Rate (mg · cm-2 · min-1) |
|---|---|
| Anhydrous form A | 1.527 ± 0.265 |
| Hemihydrate form H | 0.857 ± 0.012 |

Given that the IDR of hemihydrate form H is lower than the one of form A, this characteristic is useful to design a modified drug delivery system such as prolonged or extended drug release (Michael J. Rathbone, Jonathan Hadgraft and Michael S. Roberts (ed.), Modified Release Drug Delivery Technology, Mercel Dekker, New York 2003). Generally the basic approaches for a sustained release formulation are:

(a) insoluble, slowly eroding or swelling matrix (Robert S. Langer and Donald L. Wise (ed.), Medical Applications of Controlled Release, Volume I, CRC Press Boca Raton Fla. 1984) and (b) polymer-coated, multiparticulate (Ghebre-Sellassie I. (ed.), Multiparticulate Oral Dose Delivery, Mercel Dekker, New York 1994).

Monolithic matrices are extensively utilized for their simplicity and ease of manufacture using conventional processing equipment. Matrix systems consist of dissolved or dispersed drug within a swelling or slowly eroding polymer matrix. Drug release from these systems is governed by water penetration into the matrix followed by diffusion of drug into the surrounding medium, erosion of matrix or combination of the two. Hydrophilic gums, which form a viscous release-retarding gel layer upon hydration, are used to form a rate-controlling matrix system.

Polymer-coated multiparticulate dosage forms such as pellets and granules offer a number of potential advantages over monolithic preparations in terms of their dispersion characteristics, transit times through the gastrointestinal tract and reduced potential of gastric irritation. Extrusion-spheronization, layering or minitabletting processes are used to obtain pellets or beads or minitablets (Ghebre-Sellassie I. (ed.). Pharmaceutical Pelletization Technology, Mercel Dekker, New York 1989). They are then coated with insoluble films which act as a membrane that allows infusion of gastrointestinal fluids and the outward diffusion of dissolved drug. The polymers generally used to form the controlling-release film are cellulosic and acrylic derivatives such as ethyl cellulose and acrylic resins.

In addition, these controlled delivery systems could be improved if the product obtained from last crystallization step (particle sizes not micronized) is used directly to further slow down the drug dissolution rate. Dissolution rate and particle size are two parameters very useful to design and optimize the prolongation of drug release.

On the basis of the above considerations it emerges the advantages of the ralfinamide (and its R-enantiomer) methanesulfonate form H with respect to the form A for the manufacture of modified release dosage forms.

EXAMPLES

Example 1

Figure 1:
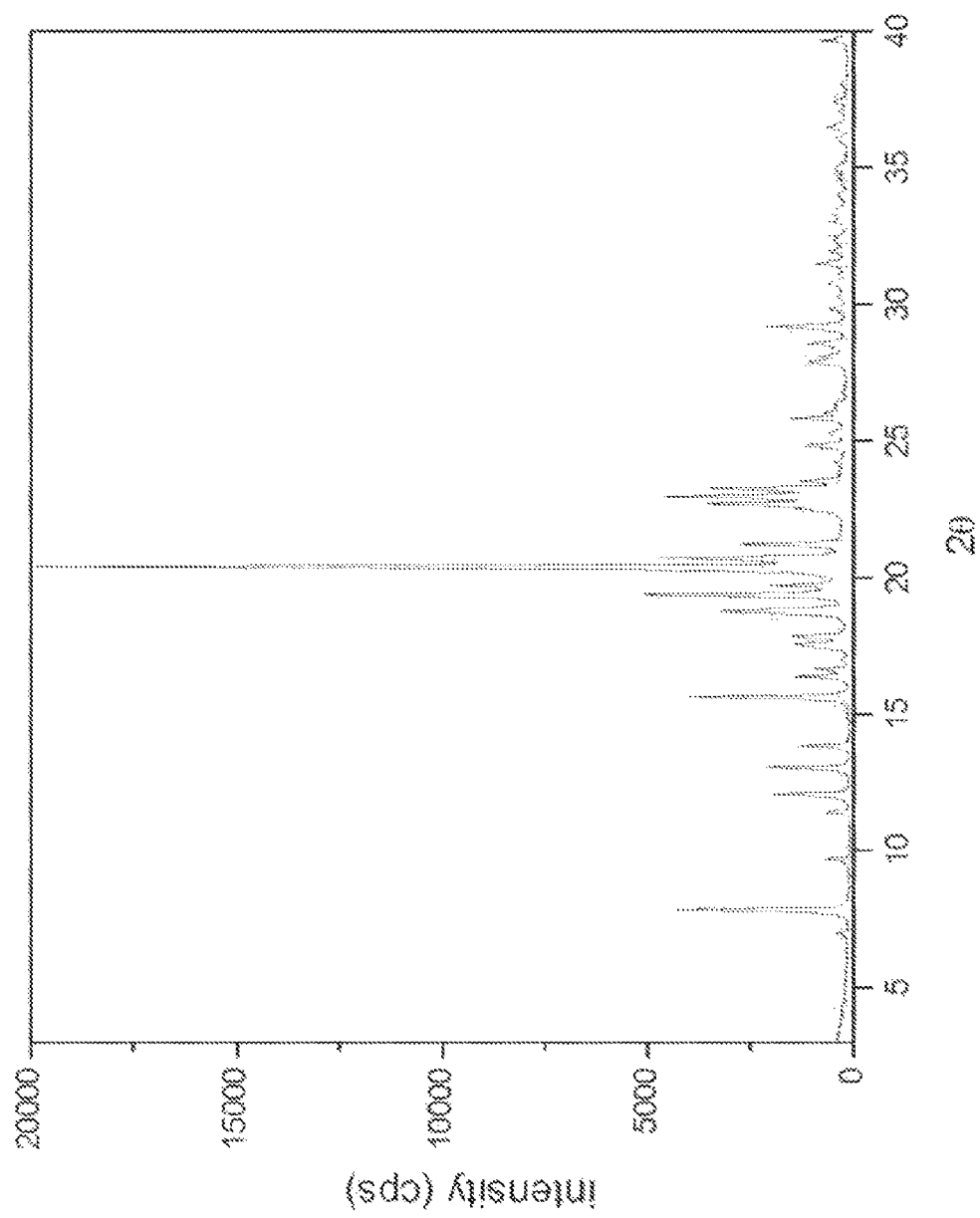
FIG. 1 represents the characteristic X-ray powder diffraction pattern (PXRD)—Table 12—of ralfinamide methanesulfonate form A; horizontal axis (2θ) in degrees; vertical axis; intensity (cps).

Synthesis of (S)-1-[4-(2-fluorobenzyloxy)benzylamino]propanamide Methanesulfonate Form H by Salification of (S)-2-[4-(2-fluorobenzyloxy)benzylamino]propanamide with Methanesulfonic Acid in Water (Direct and Reverse Addition)

1a) Direct Addition

A mixture of purified water (300 ml) and of (S)-2-[4-(2-fluorobenzyloxy) benzylamino]propanamide (60.0 g, 0.198 mol; HPLC purity 99.4 (area %), Example 25A of WO 2009/074478; enantiomeric ratio S:R=99.8:0.2, Example 26A of WO 2009/074478; residual solvents: toluene 300 ppm and methanol 50 ppm, (Example 18): alkyl methanesulfonates: MMS, EMS and IMS lower than 0.05 ppm (LOD), (Example 19). prepared as in Example 2a of WO 2009/074478, is heated up to 70° C. under mechanical stirring and under nitrogen.

Methanesulfonic acid (14.4 g, 9.7 ml, 0.149 mol) is added in 15 min at 70° C. to the stirred mixture. The solution so obtained is filtered and cooled slowly to 65° C. Methanesulfonic acid (5.3 g, 0.055 mol) is added, under stirring, to the solution kept at 65° C.

Seed crystals, prepared as in Example 3a, are added under stirring to the solution, kept at 55° C.-60° C. The mixture is cooled gradually, in 3 hours, under stirring to 5° C. and then the suspended crystalline product is isolated by filtration washed with chilled purified water (30 ml) to yield a wet product (83.2 g) which is dried at 50° C. at ambient pressure to provide 68.9 g (0.169 mol, 85.5% yield) of the product of the title.

HPLC purity: 99.9 (Area %) (Example 25A of WO 2009/074478);

HPLC enantiomeric purity: 100% (Example 26A of WO 2009/074478);

K.F.: water content 2.3% by weight (Example 17)

Figure 12:
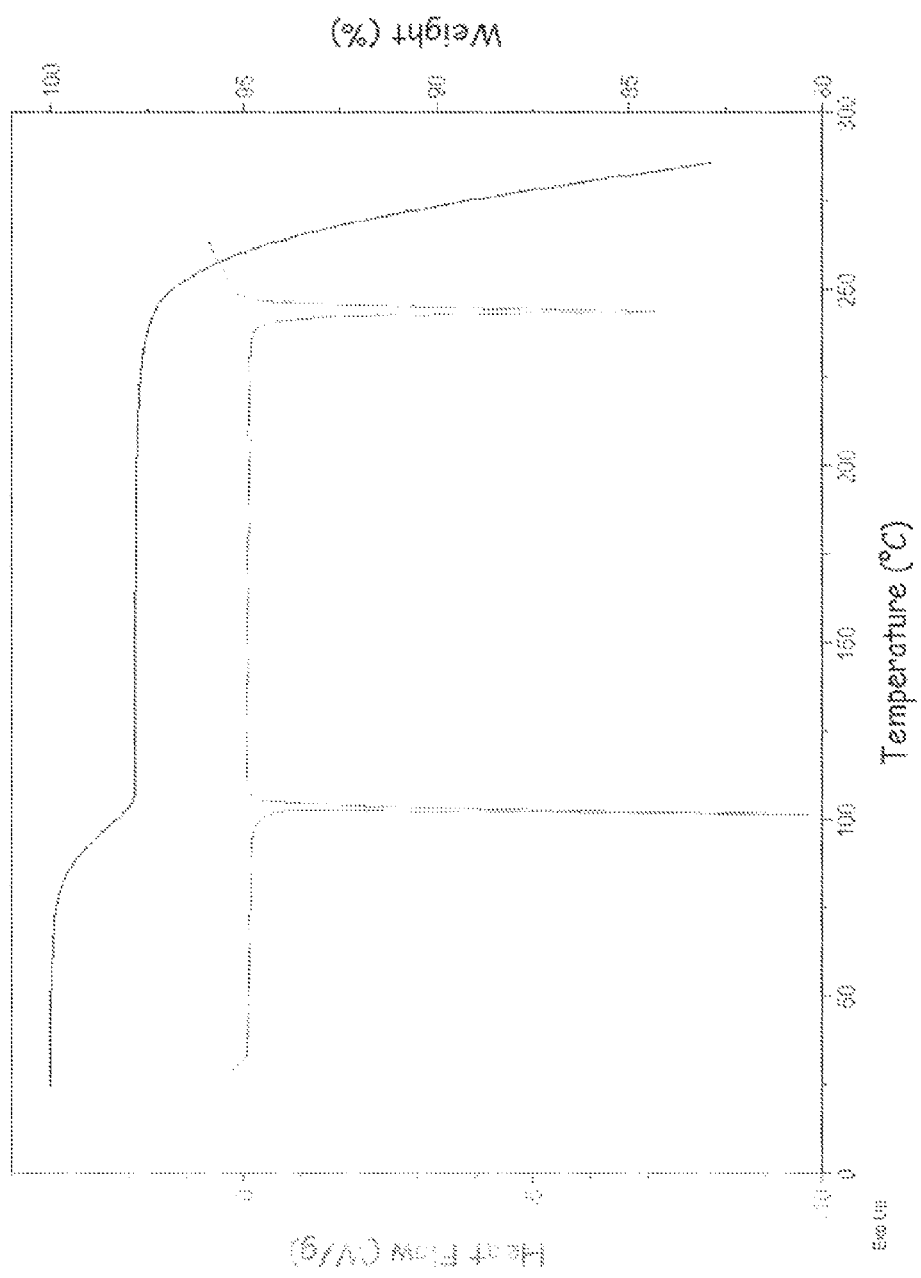
FIG. 12—DSC (lower plot) and TGA (upper plot) of ralfinamide methanesulfonate form H FIG. 13—DSC (lower plot) and TGA (upper plot) of ralfinamide methanesulfonate form A from form H by loss of water FIG. 14 (comparative example) is the characteristic X-ray powder diffraction pattern for ralfinamide hydrochloride anhydrous form; horizontal axis (2θ) in degrees; vertical axis; intensity (a.u.). Upper plot; dry powder. Lower plot; wet powder.
Figure 13:
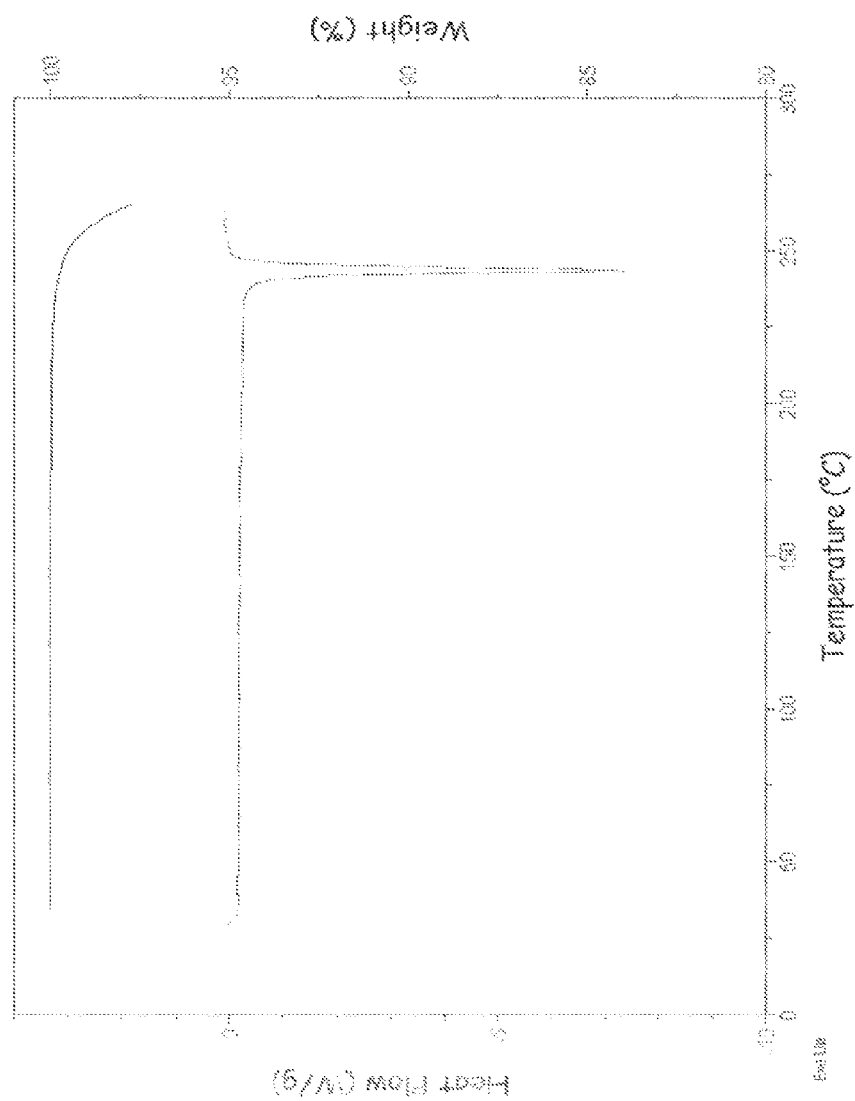

Residual solvents: toluene and methanol less than 6 ppm (LOD) (Example 18),

Alkyl methanesulfonates: MMS, EMS and IMS lower than 0.05 ppm (LOD) (Example 19);

DSC: a first endotherm at 95.1±2.0° C. (ΔH=91.4±3.3 J/g) and a second endotherm at 241.3±0.3° C. (ΔH=116.7±5.1 J/g) (Example 20 and FIG. 12);

TGA: endotherm at about 95° C. accompanied by a weight los of 2.14%, (Example 20 and FIG. 12);

High resolution NMR (Example 21); the $^1$H NMR spectrum in CD$_3$CN of (S)-2-[4-(2-fluorobenzylamino)benzylamino] propanamide methanesulfonate, form H, thus obtained, is fully consistent with the given structure and it is identical to that of form A. NMR data for all protons are reported in the following Table 1.

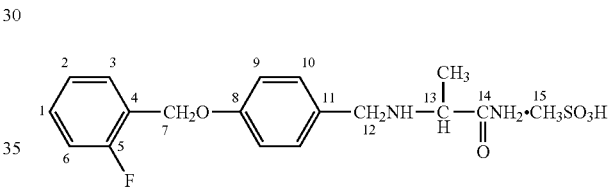

TABLE 1

| | $^1$H-NMR Spectrum: Chemical Shifts(ppm) and Coupling constants (Hz) | | |
|---|---|---|---|
| H | Chemical Shift (ppm) | Multiplicity | Coupling constant (Hz) |
| 1 | 7.43 | multiplet | |
| 2 | 7.25 | triplet | 7.0 |
| 3 | 7.57 | dt | 7.0, 1.1 |
| 6 | 7.19 | dd | 7.0; 6.0 |
| 7 | 5.21 | singlet | |
| 9 | 7.08 | Part A of an AB system | 8.7 |
| 10 | 7.48 | Part B of an AB system | 8.7 |
| 12 | 4.04; 4.16 | AB system | 12.0 |
| 13 | 3.88 | quartet | 7.0 |
| 15 | 2.51 | singlet | |
| CH$_3$—CH | 1.55 | douplet | 7.0 |
| CONH$_2$ | 6.15; 6.70 | singlet | |

Solid State CF/MAS NMR (Example 21): the solid state $^1$H CP/MAS NMR spectrum of (S)-2-[4-(2-fluorobenzyloxy)benzylamino] propanamide methanesulfonate, form H, shows a broad signal between 2.00 and 7.50 ppm, and a sharp signal at 1.76 ppm.

Figure 10:
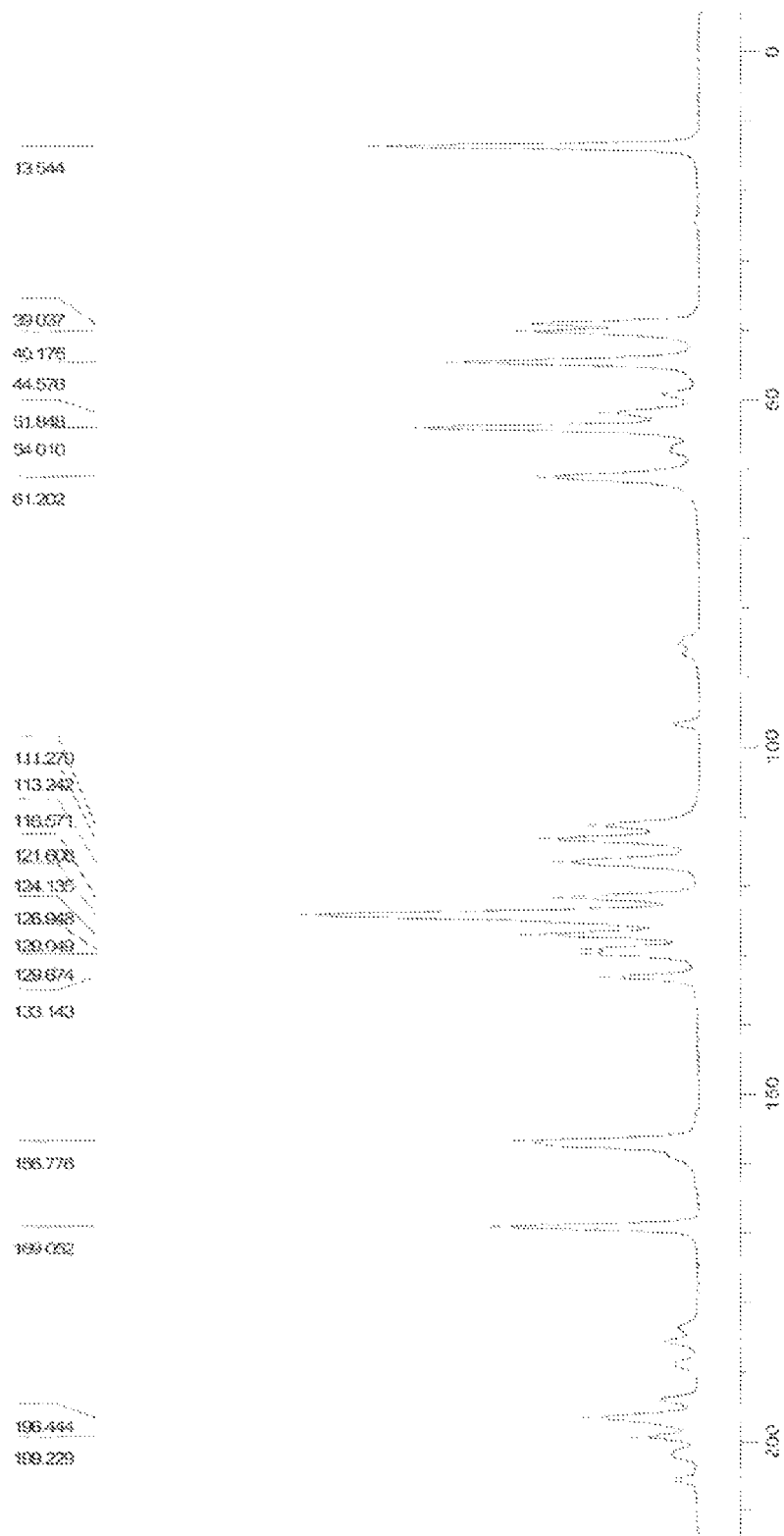
FIG. 10—$^{13}$C CP/MAS NMR of ralfinamide methanesulfonate form H; horizontal axis: chemical shift ppm; vertical axis relative intensity.
Figure 11:
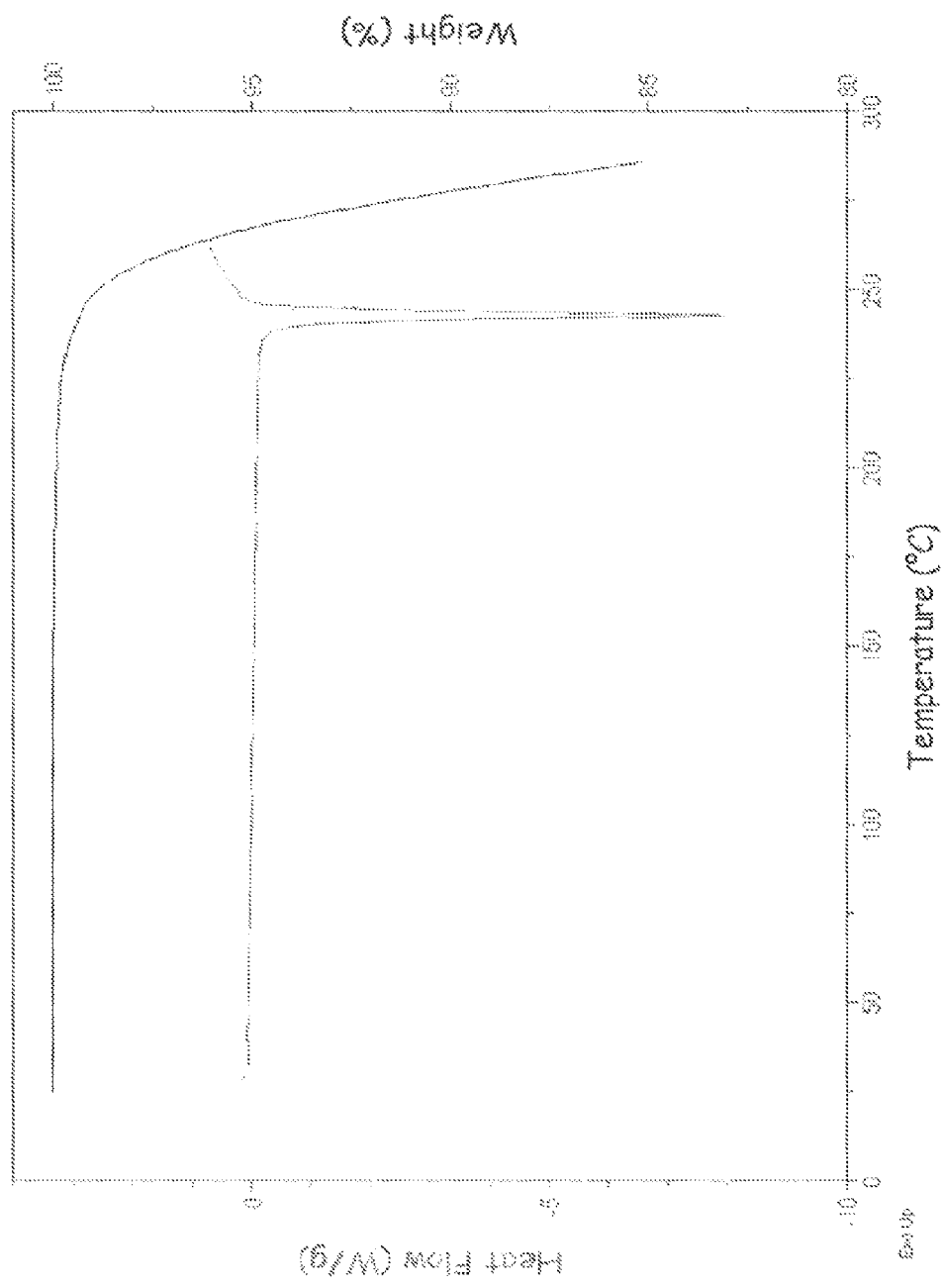
FIG. 11—DSC (lower plot) and TGA (upper plot) of ralfinamide methanesulfonate form A.

The $^{13}$C CP/MAS NMR spectrum of (S)-2-[4-(2-fluorobenzyloxy)benzylamino] propanamide methanesulfonate, form H, shows the following resonances, chemical shift in ppm, described here below in Table 2. The full spectrum is reported in FIG. 10.

TABLE 2

$^{13}$C CP/MAS, chemical shifts (ppm)

| C-1; C-2; C-3; C-5; C-6 | C-4 | C-7 | C-8 | Not attributed C signal |
|---|---|---|---|---|
| 121.6; 124.1; 126.9; 129.0; 129.7 | 156.7 | 61.2 | 169.1 | 83.0; 84.0; 85.0 |

| C-9 | C-10 | C-11 | C-12 | C-13 | C-14 | C-15 | Me—C-13 |
|---|---|---|---|---|---|---|---|
| 111.3 | 133.1 | 97.0 | 44.6 | 49.3 | 182.0 | 39.05 | 13.5 |
| 113.2 |  |  |  | 51.9 | 185.5 | 40.2 |  |
| 116.6 |  |  |  | 54.0 | 189.0 |  |  |
|  |  |  |  | 56.7 | 193.9 |  |  |
|  |  |  |  | 57.4 | 196.45 |  |  |
|  |  |  |  |  | 199.2 |  |  |
|  |  |  |  |  | 201.0 |  |  |
|  |  |  |  |  | 202.0 |  |  |
|  |  |  |  |  | 205.0 |  |  |

Figure 5:
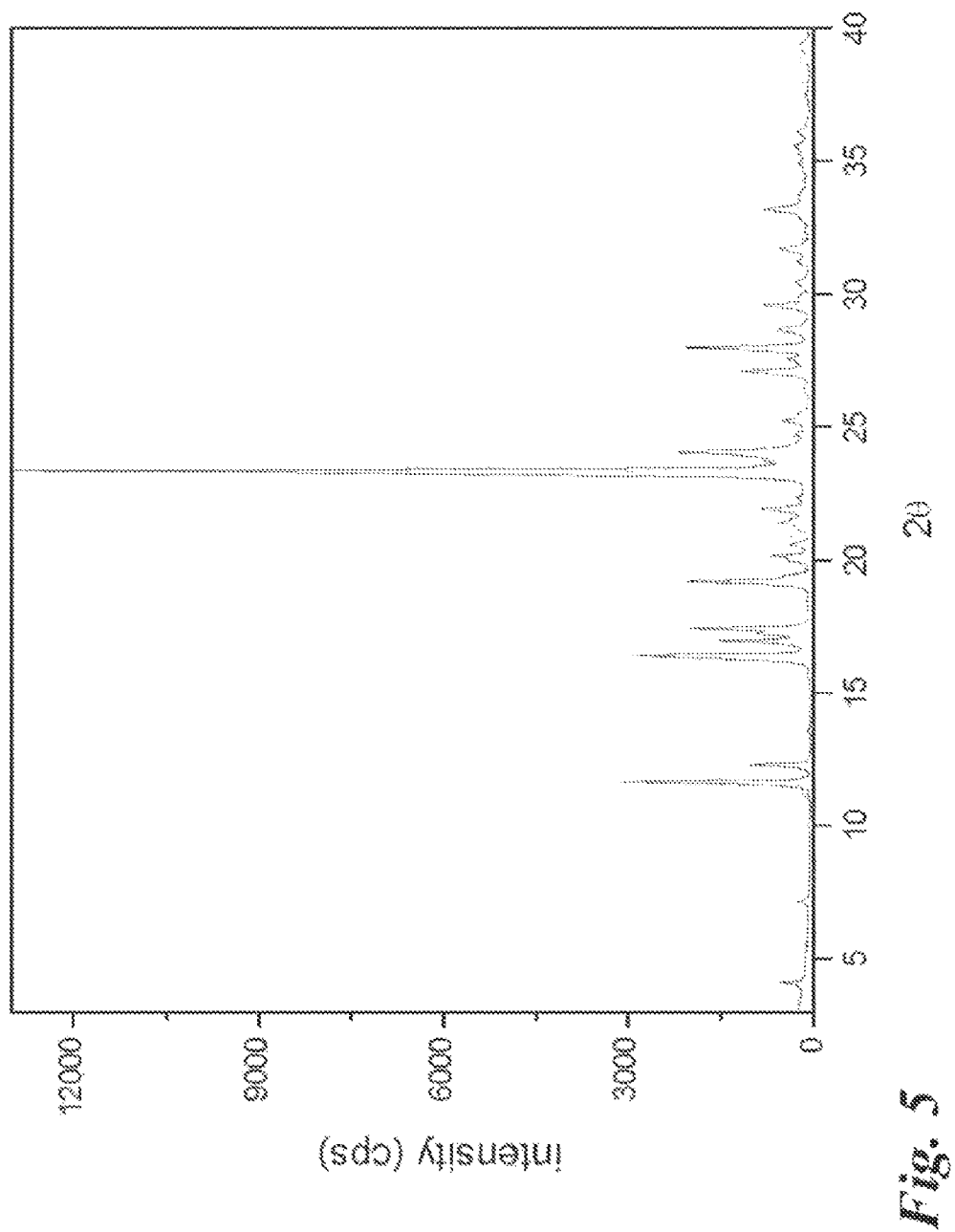
FIG. 5 is the characteristic X-ray powder diffraction pattern (PXRD) for ralfinamide methanesulfonate form H; horizontal axis (2θ) in degrees; vertical axis; intensity (cps).

PXRD analysis: In the following Table 3 is reported the observed PXRD pattern (FIG. 5) of the hemihydrate pseudopolymorph form H determined by using the instrument and conditions described in Example 22. The 2θ values are in agreement with the crystallographic parameters calculated by using the data of the SCXRD analysis.

TABLE 3

Observed (obs) and calculated (calc) PXRD patterns for form H

| | | | 2θ | | |
|---|---|---|---|---|---|
| h | k | l | (obs) | (calc) | Rel. Intensity. |
| 0 | 0 | 1 | 4.09 | 4.103 | 6.9 |
| 0 | 1 | 1 | 7.09 | 7.111 | 2.1 |
| 0 | 1 | 2 | 10.06 | 10.062 | 0.4 |
| 0 | 2 | 0 | 11.64 | 11.627 | 16.0 |
| 0 | 0 | 3 | 12.34 | 12.329 | 8.0 |
| 1 | 1 | 0 |  | 16.334 |  |
| 1 | 1 | -1 | 16.38 | 16.427 | 48.0 |
| 0 | 0 | 4 |  | 16.464 |  |
| 0 | 2 | 3 | 17.00 | 16.978 | 10.4 |
| 1 | 1 | 1 |  | 17.260 |  |
| 0 | 1 | 4 | 17.47 | 17.471 | 29.7 |
| 1 | 1 | -2 |  | 17.523 |  |
| 1 | 2 | 0 |  | 19.223 |  |
| 1 | 2 | -1 | 19.26 | 19.302 | 44.3 |
| 1 | 1 | -3 |  | 19.457 |  |
| 1 | 2 | 1 | 20.11 | 20.019 | 8.6 |
| 0 | 2 | 4 |  | 20.202 |  |
| 0 | 0 | 5 | 20.63 | 20.620 | 4.7 |
| 1 | 0 | 3 |  | 20.709 |  |
| 1 | 0 | -4 | 21.34 | 21.221 | 5.2 |
| 0 | 1 | 5 |  | 21.439 |  |
| 1 | 2 | -3 | 21.97 | 21.952 | 16.4 |
| 1 | 1 | -4 |  | 22.019 |  |
| 1 | 3 | 0 |  | 23.278 |  |
| 1 | 3 | -1 | 23.35 | 23.345 | 100.0 |
| 0 | 4 | 0 |  | 23.376 |  |
| 1 | 0 | 4 |  | 23.745 |  |
| 1 | 2 | 3 | 23.86 | 23.813 | 15.5 |
| 1 | 3 | 1 |  | 23.946 |  |
| 0 | 3 | 4 | 24.12 | 24.101 | 21.5 |
| 1 | 3 | -2 |  | 24.139 |  |
| 1 | 3 | 2 | 25.29 | 25.293 | 6.2 |
| 0 | 3 | 5 | 27.15 | 27.156 | 11.9 |
| 1 | 3 | 3 |  | 27.225 |  |
| 1 | 3 | -4 | 27.61 | 27.623 | 4.8 |
| 1 | 4 | 0 | 28.02 | 28.032 | 26.8 |
| 1 | 4 | 1 |  | 28.596 |  |
| 0 | 4 | 4 | 28.74 | 28.727 | 8.2 |
| 1 | 4 | -2 |  | 28.760 |  |
| 0 | 1 | 7 |  | 29.622 |  |
| 0 | 5 | 1 | 29.62 | 29.636 | 7.3 |
| 1 | 3 | 4 |  | 29.637 |  |
| 1 | 4 | -3 | 30.02 | 30.010 | 2.2 |
| 0 | 3 | 6 | 30.51 | 30.506 | 1.6 |
| 1 | 1 | 6 | 31.29 | 31.267 | 1.0 |
| 1 | 4 | -4 | 31.81 | 31.777 | 7.7 |
| 2 | 0 | 2 | 32.89 | 32.818 | 3.8 |
| 1 | 3 | -6 |  | 32.968 |  |
| 1 | 5 | 0 |  | 33.226 |  |
| 1 | 5 | -1 |  | 33.274 |  |
| 0 | 0 | 8 | 33.35 | 33.280 | 16.5 |
| 2 | 1 | 2 |  | 33.357 |  |
| 2 | 0 | -4 |  | 33.394 |  |
| 1 | 5 | -2 |  | 33.853 |  |
| 2 | 1 | -4 | 33.93 | 33.924 | 4.4 |
| 1 | 5 | -3 |  | 34.939 |  |
| 2 | 1 | 3 | 35.10 | 35.091 | 2.1 |
| 0 | 2 | 8 | 35.39 | 35.365 | 3.5 |
| 2 | 3 | -1 |  | 35.458 |  |
| 2 | 3 | 0 | 35.62 | 35.620 | 2.5 |
| 0 | 6 | 1 |  | 35.634 |  |
| 1 | 5 | 3 | 36.22 | 36.183 | 2.3 |
| 1 | 3 | 7 | 38.91 | 38.895 | 2.2 |
| 1 | 3 | -8 | 39.50 | 39.517 | 1.7 | h, k, l reflection indexes

1b) Reverse Addition (S)-2-[4-(2-fluorobenzyloxy)benzylamino]propanamide (60.0 g, 0.199 mol; HPLC purity 99.4 (Area %). Example 25A or WO 2009/074478; HPLC enantiomeric ratio S:R=99.8:0.2. Example 26A of WO 2008/074478; residual solvents: toluene, 300 ppm, and methanol 50 ppm, (Example 18); alkyl methanesulfonates: MMS, EMS and IMS lower than 0.05 ppm (LOD), (Example 19), prepared as in Example 2a of WO 2009/074478, is added in portion in 15 min. to a stirred solution of methanesulfonic acid (0.198 mol) in water (400 ml) to provide an heterogeneous mixture, consisting of the salt and water solution. The mixture is heated up under mechanical stirring and under nitrogen to 65° C. providing a solution. Seed crystals, prepared as in Example 3a are added to the solution at 60° C.-65° C. The mixture is gradually cooled under stirring to 5° C. in 3 hours and then the insoluble crystalline product is collected by filtration, washed with chilled purified water (30 ml) to yield a wet product (80.2 g) which is dried at 50° C. at ambient pressure to provide 65 g (0.160 mol. 80.2% yield) of the product of the title.

HPLC purity: 99.9 (Area %) (Example 25A of WO 2009/074478);

HPLC enantiomeric purity: 100 (Example 26A of WO 2009/074478);

K.F.: water content 2.3% by weight (Example 17);

Residual solvents: toluene and methanol less than 6 ppm (LOD) (Example 18);

Alkyl methanesulfonates: MMS, EMS and IMS lower than 0.05 ppm (LOD) (Example 19);

DSC: a first endotherm at 95.1±2.0° C. (ΔH=91.4±3.3 J/g) and a second endotherm at 241.3±0.3° C. (ΔH=116.7±5.1 J/g). (Example 20 and FIG. 12);

TGA: endotherm at about 95° C. accompanied by a weight loss of 2.14%. (Example 20 and FIG. 12).

Example 2

Synthesis of (R)-2-[4-(2-fluorobenzyloxy)benzylamino]propanamide Methanesulfonate Form H by Salification of (R)-2-[4-(2fluorobenzyloxy) Benzylamino]propanamide with Methanesulfonic Acid in Water A mixture of purified water (300 ml) and (R)-2-[4-(2-fluorobenzyloxy) benzylamino]propanamide (60.0 g, 0.198 mol; HPLC purity 99.4 (Area %)%). Example 25A of WO 2009/074478; enantiomeric ration R:S=99.6:0.4, Example 26B of WO 2009/074478; residual solvents: toluene 300 ppm and methanol 50 ppm, (Example 18); alkyl methanesulfonates MMS, EMS and IMS lower than 0.05 ppm (LOD), (Example 19), prepared as in Example 5a of WO 2009/074478, is heated up to 100° C. under mechanical stirring and under nitrogen providing a two liquid phases mixture.

The mixture is cooled down to 90° C. Methanesulfonic acid (14.4 g, 9.7 ml, 0.149 mol) is added in 15 min. to the stirred mixture. The temperature of the mixture raises to 93° C. and then the solution so obtained is filtered and cooled slowly to 65° C. Methanesulfonic acid (5.3 g, 0.055 mol) is added, under stirring, to the solution kept at 65° C.

Seed crystals, prepared as per Example 3b are added to the solution, kept under stirring at 55° C.-60° C. The crystallization mixture is gradually cooled in 3 hours under stirring to 5° C. and then the crystalline product is isolated by filtration, washed with chilled water (30 ml) to yield a wet product (84 g) which is dried at 50° C. at ambient pressure to provide 68.0 g (0.167 mol, 84.3% yield) of the product of the title.

HPLC purity: 99.8 (Area %) (Example 25A of WO 2000/074478);
HPLC enantiomeric purity: 100% (Example 26B of WO 2000/074478);
K.F.: water content 2.3% by weight (Example 17);
Residual solvents: toluene and methanol less than 6 ppm (LOD) (Example 18);
Alkyl methanesulfonates: MMS, EMS and IMS lower than 0.05 ppm (LOD) (Example 19):
DSC and TGA (Example 20), $^1$H-NMR spectra in $CD_3CN$, $^{13}C$ CP/MAS NMR (Example 21) and PXRD analysis (Example 22) are fully consistent with those of the (S)-enantiomer form H as reported in the Example 1a.

Example 3

Seed Crystals (S) and (R)-2-[4-(2-fluorobenzyloxy)benzylamino]propanamide Methanesulfide Form H by Slurring (S) and (R)-2-[4-(2-fluorobenzyloxy)benzylamino]propanamide Methanesulfonate Form A in Water, Respectively a) A mixture of purified water (2.5 l) and (S)-2-[4-(2-fluorobenzyloxy) benzylamino]propanamide methanesulfonate (125 g, 0.314 mol; HPLC purity 99.4 (Area %), Example 25A of WO 2009/074478; enantiomeric ration S:R=99.3:0.2. Example 26A or WO 2000/074478; residual solvents: 2-propanol 1,300 ppm, (Example 18); alkyl methanesulfonates: MMS and EMS lower than 0.05 ppm (LOD) and IMS 0.14 ppm. (Example 19), prepared as in Example 3a of WO 2009/074478, is stirred at room temperature for 24 hours. The insoluble is isolated by filtration and dried at room temperature to provide (S)-2-[4-(2-fluorobenzyloxy) benzylamino]propanamide methanesulfonate form H (63.9 g, 50% yield).

HPLC purity: 99.8 (Area %) (Example 25A of WO 2009/074478);
HPLC enantiomeric purity: 100% (Example 26A of WO 2009/074478);
K.F.: water content 2.3% by weight (Example 17);
Residual solvents: 2-propanol less than 6 ppm (LOD) (Example 18);
Alkyl methanesulfonates: MMS, EMS and IMS lower than 0.05 ppm (LOD) (Example 19);
DSC and TGA (Example 20), $^1$H-NMR spectra in $CD_3CN$, $^{13}C$ CP/MAS NMR (Example 21) and PXRD analysis (Example 22) are fully consistent with those of the (S)-2-[4-(2-fluorobenzyloxy) benzylamino]propanamide methanesulfonate form H as reported in the Example 1a.

b) (R)-2-[4-(2-fluorobenzyloxy)benzylamino]propanamide methanesulfonate form H (65 g, 51% yield) is prepared according to the same procedure described above starting from (R)-2-[4-(2-fluorobenzyloxy)benzylamino]propanamide methanesulfonate form A (HPLC purity 99.4 (Area %); enantiomeric ratio R:S=99.8:0.2, Example 26B of WO 2009/074478; residual solvents: 2-propanol 1,300 ppm, (Example 18); alkyl methanesulfonates; MMS and EMS lower than 0.05 ppm (LOD) and IMS 0.14 ppm. (Example 19) prepared as in example 5b of WO 2009/074478. The obtained salt form H is characterized as follows:

HPLC purity: 100.0 (Area %) (Example 25A of WO 2009/074478);
HPLC enantiomeric purity: 100% (Example 26B of WO 2009/074478);
K.F.: water content 2.3% by weight (Example 17);
Residual solvents: 2-propanol less than 6 ppm (LOD) (Example 18);
Alkyl methanesulfonates: MMS, EMS and IMS lower than 0.05 ppm (LOD) (Example 19);
DSC and TGA (Example 20b NMR spectra in $CD_3CN$, $^{13}C$ CP/MAS NMR (Example 21) and PXRD analysis (Example 22) are fully consistent with those of the (R)-enantiomer form H as reported in the Example 2.

Example 4

(S) and (R)-2-[4-(2-fluorobenzyloxy)benzylamino]propanamide Methanesulfonate Form H Preparation: Reverse Addition a) (S)-2-[4-2-fluorobenzyloxy) benzylamino]propanamide (60.0 g, 0.198 mol; HPLC purity 99.4 (Area %): enantiomeric ratio S:R=90.8:0.2, Example 26A of WO 2009/074478: residual solvents; toluene 300 ppm and methanol 50 ppm, (Example 18); alkyl methanesulfonates: less than 0.05 ppm (LOD), (Example 19), prepared as in Example 2a of WO 2009/074478, is added under stirring at 10° C. in five min. to a solution of methanesulfonic acid (19.3 g, 0.201 mol) in purified water (400 ml). The obtained heterogeneous mixture, which consists of the salt and the aqueous solution, is stirred at room temperature for 24 hours. The insoluble is filtered, washed with water (40 ml) and dried at room temperature to provide (S)-2-[4-(2-fluorobenzyloxy) benzylamino] propanamide methanesulfonate form H in 99% yield.

HPLC purity: 99.8 (Area %) (Example 25A of WO 2009/074478);
HPLC enantiomeric purity: 100% (Example 26A of WO 2009/074478);

K.F.: water content 2.3% by weight (Example 17);
Residual solvents: toluene and methanol less than 6 ppm (LOD) (Example 18);
Alkyl methanesulfonates: MMS, EMS and IMS lower than 0.05 ppm (LOD) (Example 19);
DSC and TGA (Example 20), $^1$H-NMR spectra in $CD_3CN$, $^{13}C$ CP/MAS NMR (Example 21) and PXRD analysis (Example 22) are fully consistent with those of the (S)-enantiomer form H as reported in the Example 1.

b) (R)-2-[4-(2-fluorobenzyloxy)benzylamino]propanamide methanesulfonate form H (91%) yield) is prepared according to the same procedure described above from (R)-2-[4-(2-fluorobenzyloxy)benzylamino]propanamide (60.0 g, 0.198 mol; HPLC purity 99.4 (Area %): HPLC. enantiomeric ratio R:S=99.8:0.2, Example 26B of WO 2009/074478; residual solvents: toluene 320 ppm and methanol 40 ppm, (Example 18); alkyl methanesulfonates: less than 0.05 ppm (LOD)), prepared as in Example 2a of WO 2009/074478. The obtained salt form H is characterized as follows:

HPLC purity: 99.8 (Area %) (Example 25A of WO 2009/074478);
HPLC enantiomeric purity: 100% (Example 26B of WO 2009/074478);
K.F.: water content 2.3% by weight (Example 17);
Residual solvents: toluene and methanol less than 6 ppm (LOD) (Example 18);
Alkyl methanesulfonates; MMS, EMS and IMS lower than 0.05 ppm (LOD) (Example 19);
DSC and TGA (Example 20), NMR spectra in $CD_3CN$. $^{13}C$ CP/MAS NMR (Example 21) and PXRD analysis (Example 22) are fully consistent with those of the (R)-enantiomer form H as reported in the Example 2.

Example 5

(S)-2-[4-(2-fluorobenzyloxy)benzylamino]propanamide Methanesulfonate Form H Preparation by Crystallization from Water A mixture of purified water (500 ml) and (S)-2-[4-(2-fluorobenzyloxy) benzylamino]propanamide methanesulfonate (78.9 g, 0.198 mol; HPLC purity 99.4 (Area %); HPLC enantiomeric ration S:R=99.8:0.2; residual solvents: 2-propanol 1,300 ppm), (Example 18): alkyl methanesulfonates content: MMS and EMS lower than 0.05 (LOD) and IMS 0.14 ppm, (Example 19), prepared as in Example 3a of WO 2009/074478, is heated up to 65° C. under mechanical stirring and under nitrogen, and then filtered.

Seed crystals, prepared as in Example 3a, are added to the solution and kept under stirring at 55-60° C. The mixture is gradually cooled under stirring to 5° C. in 3 hours and then the crystalline product is filtered, washed with chilled purified water (30 ml) to yield a wet product which is dried at 40° C. at ambient pressure to provide the product of the title. (64.8 g, 0.159 mol; 80.6% yield)

HPLC purity: 99.9 (Area %) (Example 25A of WO 2009/074478);
HPLC enantiomeric purity: 100% (Example 26A of WO 2009/074478);
K.F.: water content 2.3% by weight (Example 17);
Residual solvents: 2-propanol less than 6 ppm (LOD), (Example 18);

Alkyl methanesulfonates: MMS, EMS and IMS lower than 0.05 ppm (LOD) (Example 19);
DSC and TGA (Example 20) NMR spectra in $CD_3CN$, $^{13}C$ CP/MAS NMR (Example 21) and PXRD analysis (Example 22) are fully consistent with those of the (S)-enantiomer form H as reported in the Example 1a.

Example 6

(S)-2-[4-(2-fluorobenzyloxy)benzylamino]propanamide Methanesulfonate Form H by Crystallization from a 95:5 (w/w) Acetone/Water Mixture (S)-2-[4-(2-fluorobenzyloxy)benzylamino]propanamide methanesulfonate form A (1.5 g; HPLC purity 99.4 (Area %); HPLC enantiomeric ratio S:R=99.8:0.2; residual solvents: 2-propanol 1,300 ppm. Example 18; alkyl methanesulfonates content: MMS and EMS lower than 0.05 ppm (LOD) and IMS 0.14 ppm. Example 19), prepared as in Example 3a of WO 2009/074478, and 95:5 (w/w) acetone/water mixture (20 ml) are placed in a 50 ml round flask equipped with a reflux condenser. The suspension is heated to approximately 5° C. below the solvent boiling point and kept under magnetic stirring at this temperature for 12 hours. The suspension is then allowed to cool down spontaneously to room temperature and filtered to provide after drying in vacuo at room temperature (S)-2-[4-(2-fluorobenzyloxy)benzylamino]propanamide methanesulfonate form H in 87% yield.

HPLC purity: 99.9 (Area %) (Example 25A of WO 2009/074478);
HPLC enantiomeric purity: 100% (Example 26A of WO 2009/074478);
K.F.: water content 2.3% by weight (Example 17);
Residual solvents: 2-propanol lower than 6 ppm (LOD) and acetone 200 ppm (Example 18);
Alkyl methanesulfonates (MMS, EMS and IMS); lower than 0.05 ppm LOD (Example 10);
DSC and TGA (Example 20) NMR spectra in $CD_3CN$, $^{13}C$ CP/MAS NMR (Example 21) and PXRD analysis (Example 22) are fully consistent with those of the (S)-enantiomer form H prepared in the Example 1a.

Example 7

(S)-2-[4-(2-fluorobenzyloxy)benzylamino]propanamide Methanesulfonate Form H from (S)-2-[4-(2-fluorobenzyloxy)benzylamino]propanamide Form A Methanesulfonate by Water Uptake from Humid Air (S)-2-[4-(2-fluorobenzyloxy)benzylamino]propanamide methanesulfonate from A (3 g.; HPLC purity 99.8 (Area %), Example 25A of WO 2009/074478; HPLC enantiomeric ratio S:R=99.5:0.5, Example 26A of WO 2009/074478; residual solvents: acetone 1.023 ppm, (Example 18); alkyl methanesulfonates: MMS, EMS and IMS lower than 0.05 ppm (LOD), (Example 19), prepared as in Example 9a, kept under a 97% RH air stream at 25° C. for two months, is fully converted into the form H.

HPLC purity: 99.9 (Area %) (Example 25A of WO 2009/074478);
HPLC enantiomeric purity: 100% (Example 26A of WO 2009/074478);
K.F.: water content 2.3% by weight (Example 17);
Residual solvents: acetone 100 ppm (Example 18);

Alkyl methanesulfonates: MMS, EMS and IMS lower than 0.05 ppm (LOD) (Example 19);

DSC and TGA (Example 20), NMR spectra in $CD_3CN$, $^{13}C$ CP/MAS NMR (Example 21) and PXRD analysis (Example 22) are fully consistent with those of the (S)-enantiomer form H as reported in the Example 1a.

Example 8

Single Crystal Preparation of (S)-2-[4-(2-fluorobenzyloxy)benzylamino]propanamide Methanesulfonate Form H by Crystallization of (S)-2-[4-(2-fluorobenzyloxy) Benzylamino]propanamide Methanesulfonate Form A from Water To a saturated solution of (S)-2-[4-(2-fluorobenzyloxy) benzylamino]propanamide methanesulfonate (6 g) in water (100 ml) kept at room temperature, seeding crystals (1-2 mg, Example 3a) are added.

Figure 6:
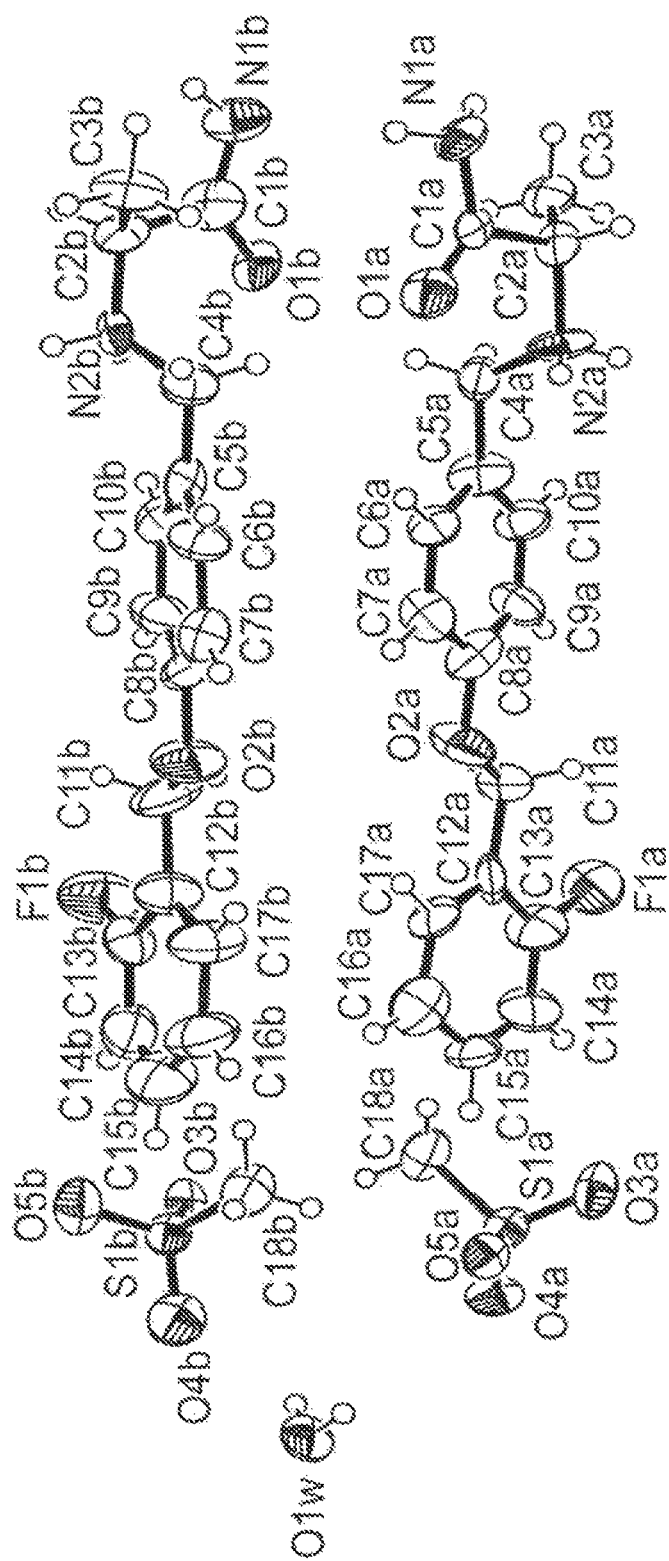
FIG. 6 depicts the symmetry independent molecular structure of ralfinamide methanesulfonate form H as derived by single crystal X-ray diffraction (atomic coordinates based on Tables 5-9).
Figure 7:
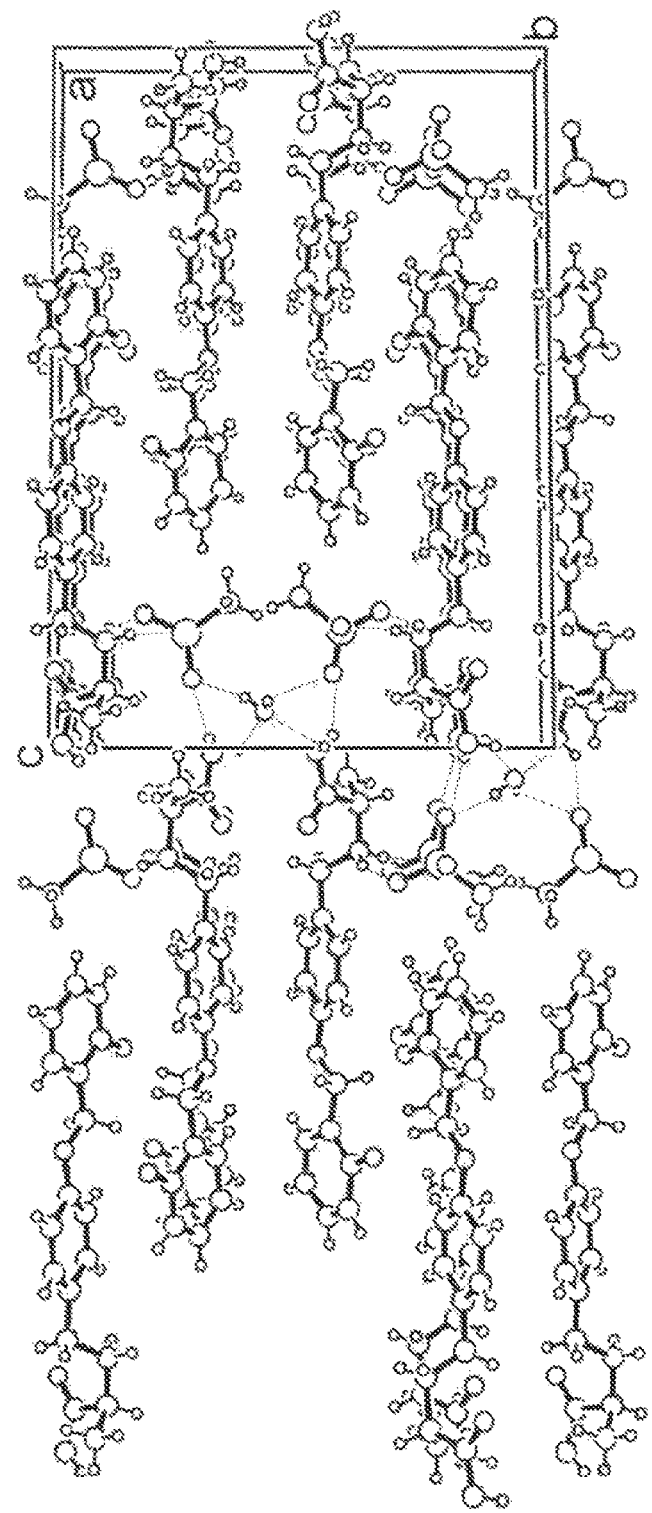
FIG. 7 depicts the molecular packing of form H projected onto the bc plane of the structure (unit cell size and symmetry based on Table 4 and atomic coordinates based on Tables 5-9). Light lines point out the hydrogen bond system.
Figure 8:
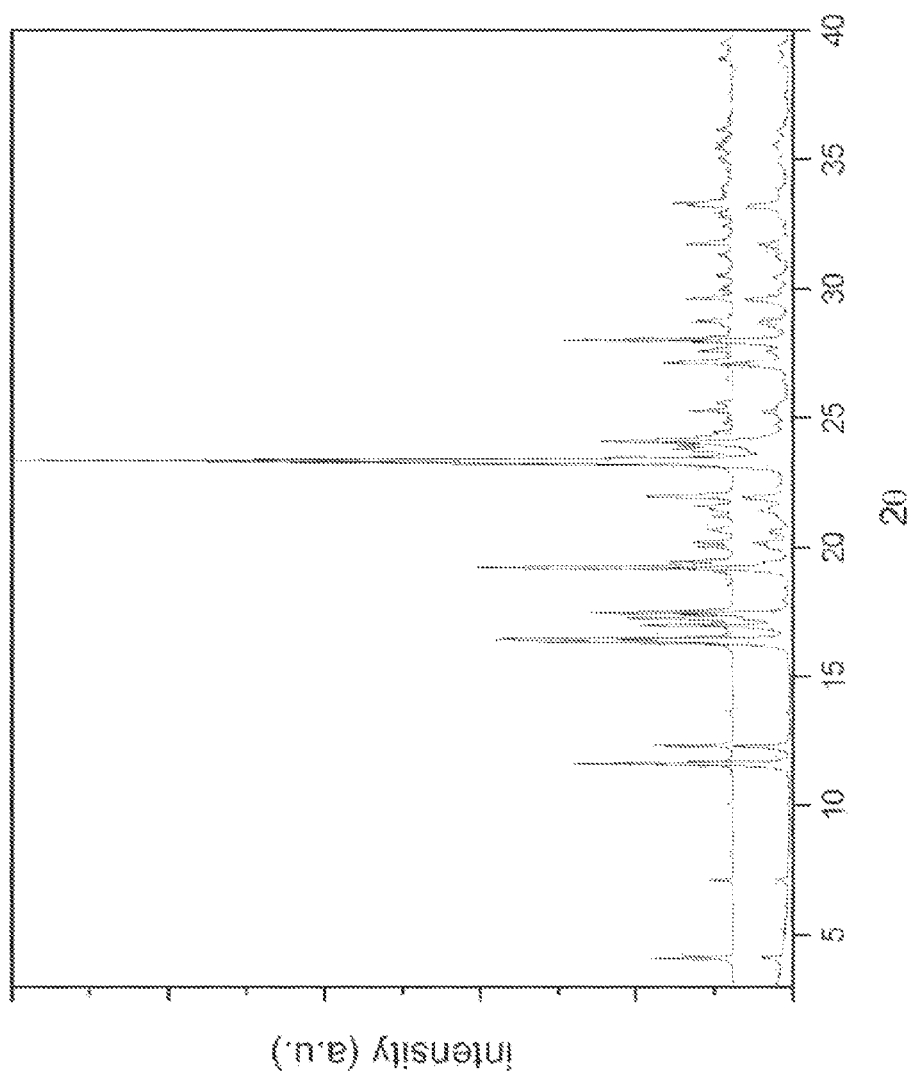
FIG. 8 is a plot of calculated versus experimental X-ray powder diffraction pattern for form H; horizontal axis (2θ) in degrees; vertical axis; intensity (a.u.). Upper plot calculated powder pattern; lower plot experimental powder pattern.

Once the seeds have been added, the nucleation is quite fast. A very small needle (0.63×0.02×0.02 mm) is selected and mounted on a glass fiber and used in the diffraction experiment. Data are collected with Mo $K_\alpha$ radiation (λ=0.71069 Å) on a Bruker APEX II diffractometer equipped with graphite monochromator and a very sensitive CCD area detector (Bruker (2008). APEX-II (Version 2008.1-0), SAINT (Version 7.51A) and SADABS (Version 2007/4). Bruker AXS Inc., Madison, Wis., USA). The structure is solved with SIR97 (Altomare, A., Burla, M. C., Camalli, M., Cascarano G., Giacovazzo, C. Guagliardi A., Moliterni, A. G. G., Polidori G. & Spagna, R. J. Appl. Cryst, 1999.32, 115-119) and refined with SHELX97L (Sheldrick G. M., Acta Cryst A 2008, 64, 112-122). Hydrogen atoms are located by difference Fourier maps and then refined in constrained positions, with the exception of the hydrogen atoms of the water molecule, for which only a restrain on the bond length is applied. The refinement is performed with anisotropic displacement parameters for all the non-hydrogen atoms. The phenyl rings are refined as rigid body. (The absolute configuration is assumed from the anhydrous form and not refined). The crystallographic parameters determined in the SCXRD experiment are reported in Table 4 (where the crystallographic parameters are compared with those of crystalline form A) and Tables 5-9 (where the numbering of the atoms is in conformity with FIG. 6). The molecular structure and the crystal packing of ralfinamide methanesulfonate form H are reported in FIGS. 6 and 7, respectively. Both the drawings are obtained with Oak Ridge Thermal-Ellipsoid Plot Program (ORTEP) (L. J. Farrugia, J. Appl. Cryst. 1997, 30, 365). In FIG. 6 the a.d.p. ellipsoids are shown at the 50% probability level.

TABLE 4

Single Crystal X-ray Crystallographic Analysis of ralfinamide methanesulfonate crystal parameters

|  | Form A | Form H |
|---|---|---|
| Cell parameters: | a = 22.689(3) Å | a = 5.844(4) Å |
| Å = Angstrom | b = 15.5107(11) Å | b = 15.221(10) Å |
| ° = degrees | c = 5.5366(2) Å | c = 21.670(15) Å |
|  | α = 90° | α = 90° |
|  | β = 90° | β = 96.361(10)° |
|  | γ = 90° | γ = 90° |
|  | V = 1948.5(3) Å$^3$ | V = 1916(2) Å$^3$ |
| Space group | $P2_12_12_1$, orthorhombic | $P2_1$, monoclinic |
| Z (multiplicity) | 4 | 2 |

TABLE 4-continued

Single Crystal X-ray Crystallographic Analysis of ralfinamide methanesulfonate crystal parameters

|  | Form A | Form H |
|---|---|---|
| Density calculated, g/cm$^3$ | 1.358 | 1.413 | a, b and c define the length of the sides of the unit cells; α, β and γ define the relative angles of the cell sides; V defines the volume of the cell.

a, b and c define the length of the sides of the unit cells; α, β and γ define the relative angles of the cell sides; V defines the volume of the cell.

TABLE 5

(refers to FIG. 6)
Fractional Atomic Coordinates and Equivalent Isotropic Atomic Displacement Parameters ($U_{eq}$, Å$^2$) for form H

| atom | x | y | z | $U_{eq}$* |
|---|---|---|---|---|
| S1A | 0.0470(5) | 0.2715(2) | 0.84056(12) | 0.0478(8) |
| F1A | -0.1314(12) | 0.2035(5) | 0.5752(3) | 0.078(2) |
| O1A | 0.4792(14) | 0.3412(5) | 0.1126(3) | 0.058(2) |
| O2A | 0.2486(13) | 0.3129(5) | 0.4474(3) | 0.062(2) |
| O3A | -0.0335(15) | 0.1887(5) | 0.8130(4) | 0.074(2) |
| O4A | -0.0203(12) | 0.2835(6) | 0.9035(3) | 0.070(2) |
| O5A | 0.2945(12) | 0.2805(5) | 0.8416(3) | 0.052(2) |
| N1A | 0.3626(15) | 0.3224(5) | 0.0107(4) | 0.055(3) |
| N2A | 0.1672(14) | 0.2364(5) | 0.1559(3) | 0.042(2) |
| C1A | 0.342(2) | 0.3075(8) | 0.0715(5) | 0.050(3) |
| C2A | 0.1590(18) | 0.2441(6) | 0.0864(5) | 0.042(3) |
| C3A | -0.0767(18) | 0.2616(8) | 0.0555(5) | 0.061(4) |
| C4A | 0.065(2) | 0.3132(7) | 0.1863(4) | 0.048(3) |
| C5A | 0.1108(14) | 0.3081(5) | 0.2566(2) | 0.051(3) |
| C6A | 0.3184(13) | 0.3406(5) | 0.2852(3) | 0.063(4) |
| C7A | 0.3607(12) | 0.3415(5) | 0.3496(3) | 0.061(4) |
| C8A | 0.1954(14) | 0.3099(6) | 0.3854(2) | 0.055(3) |
| C9A | -0.0121(12) | 0.2775(5) | 0.3568(3) | 0.053(3) |
| C10A | -0.0544(11) | 0.2766(5) | 0.2924(3) | 0.064(4) |
| C11A | 0.0794(18) | 0.2810(8) | 0.4844(4) | 0.053(3) |
| C12A | 0.1761(14) | 0.2876(5) | 0.5503(2) | 0.051(3) |
| C13A | 0.0588(12) | 0.2455(5) | 0.5943(4) | 0.066(4) |
| C14A | 0.1413(14) | 0.2504(5) | 0.6569(3) | 0.070(4) |
| C15A | 0.3411(15) | 0.2973(5) | 0.6755(2) | 0.069(4) |
| C16A | 0.4584(12) | 0.3394(5) | 0.6315(4) | 0.065(4) |
| C17A | 0.3759(14) | 0.3346(5) | 0.5690(3) | 0.065(4) |
| C18A | -0.085(2) | 0.3566(9) | 0.7950(5) | 0.077(4) |
| S1B | 0.3244(5) | 0.5815(2) | 0.83652(12) | 0.0443(8) |
| F1B | 0.3600(12) | 0.6426(6) | 0.5705(3) | 0.090(2) |
| O1B | 0.1081(13) | 0.5127(5) | 0.1090(3) | 0.054(2) |
| O2B | 0.7411(14) | 0.5331(6) | 0.4406(3) | 0.071(3) |
| O3B | 0.0739(12) | 0.5777(5) | 0.8306(3) | 0.054(2) |
| O4B | 0.4423(14) | 0.5655(5) | 0.8959(3) | 0.069(2) |
| O5B | 0.3986(13) | 0.6613(5) | 0.8090(4) | 0.061(2) |
| N1B | 0.1412(15) | 0.5293(7) | 0.0067(4) | 0.062(3) |
| N2B | 0.4589(13) | 0.6175(6) | 0.1498(3) | 0.054(3) |
| C1B | 0.2059(19) | 0.5488(8) | 0.0683(5) | 0.053(3) |
| C2B | 0.396(2) | 0.6172(7) | 0.0816(5) | 0.053(3) |
| C3B | 0.6108(18) | 0.5973(9) | 0.0475(4) | 0.065(4) |
| C4B | 0.589(2) | 0.5408(8) | 0.1799(5) | 0.059(4) |
| C5B | 0.6164(13) | 0.5453(5) | 0.2497(2) | 0.052(3) |
| C6B | 0.8232(11) | 0.5140(5) | 0.2795(3) | 0.047(3) |
| C7B | 0.8592(11) | 0.5125(5) | 0.3439(3) | 0.063(4) |
| C8B | 0.6885(14) | 0.5423(6) | 0.3786(2) | 0.050(3) |
| C9B | 0.4817(12) | 0.5736(5) | 0.3488(3) | 0.060(4) |
| C10B | 0.4457(10) | 0.5751(5) | 0.2843(3) | 0.049(3) |
| C11B | 0.563(2) | 0.5695(9) | 0.4768(4) | 0.070(4) |
| C12B | 0.6629(14) | 0.5579(5) | 0.5434(2) | 0.049(3) |
| C13B | 0.5449(12) | 0.6002(5) | 0.5871(4) | 0.053(3) |
| C14B | 0.6295(15) | 0.5975(5) | 0.6496(3) | 0.072(4) |
| C15B | 0.8321(15) | 0.5524(6) | 0.6684(3) | 0.073(5) |
| C16B | 0.9501(12) | 0.5101(6) | 0.6247(4) | 0.077(4) |
| C17B | 0.8655(14) | 0.5128(5) | 0.5622(3) | 0.070(4) |
| C18B | 0.414(2) | 0.4981(7) | 0.7871(5) | 0.059(4) |
| O1W | 0.7261(14) | 0.4263(6) | 0.9536(3) | 0.058(2) |

*Equivalent isotropic $U_{eq}$ defined as one third of the trace of the orthogonalized $U_{ij}$ tensor

TABLE 6 refers to FIG. 6
Anisotropic Atomic Displacement Parameters* ($U_{ij}$*, Å$^2$) for form H

| Atom | $U_{11}$ | $U_{22}$ | $U_{33}$ | $U_{23}$ | $U_{13}$ | $U_{12}$ |
|---|---|---|---|---|---|---|
| S1A | 0.060(2) | 0.045(2) | 0.0429(18) | 0.078(16) | 0.0263(16) | 0.0079(19) |
| F1A | 0.085(6) | 0.093(6) | 0.057(4) | 0.004(4) | 0.016(4) | −0.036(5) |
| O1A | 0.060(6) | 0.065(6) | 0.052(5) | 0.005(5) | 0.024(5) | −0.004(5) |
| O2A | 0.080(6) | 0.077(6) | 0.028(4) | 0.000(4) | −0.002(4) | −0.015(5) |
| O3A | 0.105(7) | 0.043(5) | 0.083(6) | −0.020(5) | 0.047(5) | −0.006(5) |
| O4A | 0.065(5) | 0.098(7) | 0.049(4) | −0.009(5) | 0.017(4) | 0.021(5) |
| O5A | 0.053(5) | 0.054(5) | 0.049(4) | −0.013(4) | 0.008(4) | 0.013(5) |
| N1A | 0.073(7) | 0.038(6) | 0.057(6) | 0.022(5) | 0.020(5) | 0.000(5) |
| N2A | 0.057(6) | 0.033(6) | 0.040(5) | 0.007(4) | 0.026(5) | 0.002(5) |
| C1A | 0.059(9) | 0.048(8) | 0.042(7) | 0.007(6) | 0.006(7) | 0.007(7) |
| C2A | 0.045(8) | 0.032(7) | 0.053(7) | −0.012(5) | 0.030(6) | −0.011(6) |
| C3A | 0.055(9) | 0.080(10) | 0.052(7) | −0.002(8) | 0.023(7) | −0.017(8) |
| C4A | 0.085(9) | 0.019(6) | 0.044(7) | 0.015(6) | 0.028(6) | 0.003(6) |
| C5A | 0.081(9) | 0.033(7) | 0.044(7) | 0.000(6) | 0.031(7) | −0.001(7) |
| C6A | 0.102(11) | 0.046(8) | 0.047(8) | 0.011(6) | 0.036(8) | −0.004(8) |
| C7A | 0.078(10) | 0.046(8) | 0.058(8) | −0.007(6) | 0.001(8) | −0.016(7) |
| C8A | 0.050(8) | 0.077(10) | 0.040(7) | 0.022(7) | 0.011(7) | −0.008(7) |
| C9A | 0.057(8) | 0.085(10) | 0.018(6) | 0.024(7) | 0.012(6) | −0.004(8) |
| C10A | 0.051(8) | 0.071(9) | 0.070(9) | 0.015(8) | 0.011(7) | 0.000(8) |
| C11A | 0.074(9) | 0.057(8) | 0.031(6) | −0.001(6) | 0.012(6) | −0.008(8) |
| C12A | 0.063(8) | 0.045(8) | 0.044(7) | −0.002(6) | 0.010(7) | −0.005(7) |
| C13A | 0.065(10) | 0.109(13) | 0.024(7) | 0.009(7) | 0.008(7) | 0.003(9) |
| C14A | 0.109(12) | 0.056(10) | 0.055(9) | −0.018(7) | 0.047(9) | 0.001(8) |
| C15A | 0.125(13) | 0.046(9) | 0.035(7) | −0.009(7) | 0.010(8) | 0.024(9) |
| C16A | 0.086(11) | 0.060(9) | 0.049(8) | 0.009(7) | 0.009(8) | 0.006(8) |
| C17A | 0.116(12) | 0.057(9) | 0.025(7) | 0.009(6) | 0.019(7) | 0.008(8) |
| C18A | 0.079(10) | 0.085(11) | 0.066(9) | 0.028(8) | −0.007(8) | 0.007(9) |
| S1B | 0.057(2) | 0.0415(19) | 0.0369(17) | −0.0030(16) | 0.0156(6) | 0.0057(18) |
| F1B | 0.060(5) | 0.142(8) | 0.067(5) | 0.003(5) | 0.002(4) | 0.027(5) |
| O1B | 0.057(5) | 0.046(5) | 0.062(5) | 0.011(4) | 0.027(4) | −0.002(4) |
| O2B | 0.095(7) | 0.094(7) | 0.026(4) | 0.003(4) | 0.011(5) | 0.020(6) |
| O3B | 0.064(5) | 0.030(4) | 0.070(5) | −0.013(4) | 0.020(4) | −0.005(4) |
| O4B | 0.119(7) | 0.048(6) | 0.041(5) | −0.010(4) | 0.012(5) | 0.021(5) |
| O5B | 0.068(6) | 0.042(5) | 0.071(6) | 0.001(5) | 0.003(4) | −0.009(4) |
| N1B | 0.068(7) | 0.069(7) | 0.053(6) | 0.015(5) | 0.027(6) | 0.018(6) |
| N2B | 0.079(8) | 0.060(7) | 0.031(5) | −0.012(5) | 0.037(5) | −0.010(6) |
| C1B | 0.049(8) | 0.063(10) | 0.049(8) | −0.002(7) | 0.012(7) | 0.004(7) |
| C2B | 0.086(9) | 0.035(7) | 0.040(7) | −0.001(6) | 0.023(7) | 0.004(7) |
| C3B | 0.078(9) | 0.094(10) | 0.026(6) | −0.006(6) | 0.020(6) | −0.028(8) |
| C4B | 0.075(9) | 0.046(8) | 0.059(8) | 0.011(7) | 0.023(7) | 0.019(7) |
| C5B | 0.069(9) | 0.050(8) | 0.042(7) | −0.005(6) | 0.026(7) | −0.011(7) |
| C6B | 0.016(6) | 0.061(8) | 0.065(8) | −0.007(7) | 0.004(6) | 0.008(6) |
| C7B | 0.080(10) | 0.072(10) | 0.035(7) | 0.001(7) | −0.004(7) | 0.006(8) |
| C8B | 0.053(8) | 0.049(8) | 0.049(8) | 0.017(6) | 0.012(7) | 0.016(7) |
| C9B | 0.099(10) | 0.061(9) | 0.024(6) | −0.007(7) | 0.025(7) | 0.008(9) |
| C10B | 0.054(8) | 0.035(7) | 0.062(8) | 0.008(7) | 0.020(6) | 0.004(7) |
| C11B | 0.093(10) | 0.092(11) | 0.026(6) | 0.000(8) | 0.011(7) | −0.018(9) |
| C12B | 0.038(7) | 0.053(9) | 0.053(8) | 0.003(6) | −0.008(6) | 0.009(6) |
| C13B | 0.072(10) | 0.047(9) | 0.040(7) | −0.001(6) | 0.010(7) | −0.004(7) |
| C14B | 0.101(12) | 0.053(10) | 0.064(10) | −0.012(7) | 0.023(9) | 0.012(8) |
| C15B | 0.066(9) | 0.128(14) | 0.024(7) | 0.014(8) | 0.006(7) | 0.002(9) |
| C16B | 0.076(10) | 0.078(11) | 0.079(10) | 0.014(9) | 0.012(9) | −0.020(8) |
| C17B | 0.104(12) | 0.077(10) | 0.030(7) | 0.007(7) | 0.014(7) | 0.002(9) |
| C18B | 0.075(9) | 0.037(7) | 0.070(8) | −0.013(6) | 0.036(7) | 0.027(7) |
| O1W | 0.083(6) | 0.052(5) | 0.041(4) | −0.012(4) | 0.020(4) | 0.001(5) |

*the anisotropic displacement parameter exponent takes the form: $-2\pi^2(h^2a^{*2}U_{11} + k^2b^{*2}U_{22} + \ldots + 2hka^*b^*U_{12})$

TABLE 7 refers to FIG. 6
Bond Lengths (Å) for form H

| | | | | | | | |
|---|---|---|---|---|---|---|---|
| S1A-O3A | 1.450(8) | S1B-O4B | 1.412(7) | N2A-C2A | 1.506(12) | N2B-C4B | 1.502(13) |
| S1A-O5A | 1.451(7) | S1B-O5B | 1.442(7) | C1A-C2A | 1.500(14) | C1B-C2B | 1.525(15) |
| S1A-O4A | 1.472(7) | S1B-O3B | 1.456(7) | C2A-C3A | 1.487(13) | C2B-C3B | 1.557(13) |
| S1A-C18A | 1.755(12) | S1B-C18B | 1.777(10) | C4A-C5A | 1.520(10) | C4E-C5B | 1.503(11) |
| F1A-C13A | 1.309(8) | F1B-C13B | 1.276(8) | C5A-C6A | 1.3900* | C5B-C6B | 1.3900* |
| O1A-C1A | 1.242(12) | O1B-C1B | 1.232(12) | C5A-C10A | 1.3900* | C5B-C10B | 1.3900* |
| O2A-C8A | 1.345(7) | O2B-C8B | 1.351(8) | C6A-C7A | 1.3900* | C6B-C7B | 1.3900* |
| O2A-C11A | 1.427(10) | O2B-C11B | 1.478(12) | C7A-C8A | 1.3900* | C7B-C8B | 1.3900* |
| N1A-C1A | 1.358(12) | N1B-C1B | 1.378(13) | C8A-C9A | 1.3900 | C8B-C9B | 1.3900* |
| N2A-C4A | 1.498(11) | N2B-C2B | 1.483(12) | C9A-C10A | 1.3900* | C9B-C10B | 1.3900* |

TABLE 7-continued refers to FIG. 6
Bond Lengths (Å) for form H

| C11A-C12A | 1.480(10) | C11B-C12B | 1.505(11) |
|---|---|---|---|
| C12A-C13A | 1.3900* | C12B-C13B | 1.3900* |
| C12A-C17A | 1.3900* | C12B-C17B | 1.3900* |
| C13A-C14A | 1.3900* | C13B-C14B | 1.3900* |
| C14A-C15A | 1.3900* | C14B-C15B | 1.3900* |
| C15A-C16A | 1.3900* | C15B-C16B | 1.3900* |
| C16A-C17A | 1.3900* | C16B-C17B | 1.3000* |

*deriving from rigid body refinement of the aromatic rings

TABLE 8 refers to FIG. 6
Bond angles (°) for form H

| O3A-S1A-O5A | 111.5(5) | O4B-S1B-O5B | 112.6(5) |
|---|---|---|---|
| O3A-S1A-O4A | 112.4(5) | O4B-S1B-O3B | 117.3(5) |
| O5A-S1A-O4A | 110.0(4) | O5B-S1B-O3B | 110.0(5) |
| O3A-S1A-C18A | 108.0(6) | O4B-S1B-C18B | 106.3(5) |
| O5A-S1A-C18A | 108.3(7) | O5B-S1B-C18B | 103.3(5) |
| O4A-S1A-C18A | 106.5(5) | O3B-S1B-C18B | 106.2(5) |
| C8A-O2A-C11A | 116.9(7) | C8B-O2B-C11B | 113.2(8) |
| C4A-N2A-C2A | 114.1(7) | C2B-N2B-C4B | 119.2(8) |
| O1A-C1A-N1A | 120.4(11) | O1B-C1B-N1B | 119.8(11) |
| O1A-C1A-C2A | 122.1(10) | O1B-C1B-C2B | 123.6(10) |
| N1A-C1A-C2A | 117.3(10) | N1B-C1B-C2B | 116.5(10) |
| C3A-C2A-C1A | 115.7(9) | N2B-C2B-C1B | 106.7(9) |
| C3A-C2A-N2A | 112.9(7) | N2B-C2B-C3B | 110.4(9) |
| C1A-C2A-N2A | 108.7(9) | C1B-C2B-C3B | 112.7(9) |
| N2A-C4A-C5A | 111.5(8) | N2B-C4B-C5B | 113.1(9) |
| C6A-C5A-C10A | 120.0 | C6B-C5B-C10B | 120.0 |
| C6A-C5A-C4A | 118.5(7) | C6B-C5B-C4B | 116.2(6) |
| C10A-C5A-C4A | 121.4(7) | C10B-C5B-C4B | 123.7(6) |
| C7A-C6A-C5A | 120.0* | C7B-C6B-C5B | 120.0* |
| C6A-C7A-C8A | 120.0* | C6B-C7B-C8B | 120.0* |
| O2A-C8A-C9A | 123.4(6) | O2B-C8B-C7B | 114.0(7) |
| O2A-C8A-C7A | 116.6(6) | O2B-C8B-C9B | 126.0(7) |
| C9A-C8A-C7A | 120.0* | C7B-C8B-C9B | 120.0* |
| C10A-C9A-C8A | 120.0* | C10B-C9B-C8B | 120.0* |
| C9A-C10A-C5A | 120.0* | C9B-C10B-C5B | 120.0* |
| O2A-C11A-C12A | 107.8(8) | O2B-C11B-C12B | 104.2(9) |
| C13A-C12A-C17A | 120.0* | C13B-C12B-C17B | 120.0* |
| C13A-C12A-C11A | 117.7(7) | C13B-C12B-C11B | 115.5(8) |
| C17A-C12A-C11A | 122.3(7) | C17B-C12B-C11B | 124.4(8) |
| F1A-C13A-C14A | 121.6(6) | F1B-C13B-C12B | 120.7(7) |
| F1A-C13A-C12A | 118.4(6) | F1B-C13B-C14B | 119.3(7) |
| C14A-C13A-C12A | 120.0* | C12B-C13B-C14B | 120.0* |
| C13A-C14A-C15A | 120.0* | C13B-C14B-C15B | 120.0* |
| C14A-C15A-C16A | 120.0* | C16B-C15B-C4B | 120.0* |
| C17A-C16A-C15A | 120.0* | C17B-C16B-C15B | 120.0* |
| C16A-C17A-C12A | 120.0* | C16B-C17B-C12B | 120.0* |

*deriving from rigid body refinement of the aromatic rings

TABLE 9 refers to FIG. 6
H-atom Fractional Atomic Coordinates and Isotropic
Atomic Displacement Parameters ($U_{iso}$, Å$^2$) for form H

| atom | x | y | z | $U_{iso}$ |
|---|---|---|---|---|
| H21 | 0.0915 | 0.1874 | 0.1650 | 0.050 |
| H22 | 0.3149 | 0.2303 | 0.1721 | 0.050 |
| H2A | 0.2040 | 0.1865 | 0.0715 | 0.050 |
| H3A1 | −0.1809 | 0.2181 | 0.0682 | 0.092 |
| H3A2 | −0.0755 | 0.2592 | 0.0113 | 0.092 |
| H3A3 | −0.1258 | 0.3188 | 0.0672 | 0.092 |
| H4A1 | −0.0999 | 0.3145 | 0.1742 | 0.057 |
| H4A2 | 0.1299 | 0.3671 | 0.1720 | 0.057 |
| H6A | 0.4289 | 0.3617 | 0.2612 | 0.075 |
| H7A | 0.4995 | 0.3632 | 0.3687 | 0.073 |
| H9A | −0.1227 | 0.2564 | 0.3808 | 0.063 |

TABLE 9-continued refers to FIG. 6
H-atom Fractional Atomic Coordinates and Isotropic
Atomic Displacement Parameters ($U_{iso}$, Å$^2$) for form H

| atom | x | y | z | $U_{iso}$ |
|---|---|---|---|---|
| H10A | −0.1933 | 0.2548 | 0.2733 | 0.076 |
| H11A | 0.0419 | 0.2203 | 0.4739 | 0.064 |
| H11B | −0.0601 | 0.3157 | 0.4771 | 0.064 |
| H14A | 0.0628 | 0.2222 | 0.6863 | 0.084 |
| H15A | 0.3962 | 0.3006 | 0.7174 | 0.083 |
| H16A | 0.5920 | 0.3708 | 0.6440 | 0.078 |
| H17A | 0.4544 | 0.3627 | 0.5396 | 0.078 |
| H18A | −0.0426 | 0.3523 | 0.7536 | 0.116 |
| H18B | −0.0349 | 0.4123 | 0.8126 | 0.116 |
| H18C | −0.2490 | 0.3520 | 0.7940 | 0.116 |
| H23 | 0.3280 | 0.6232 | 0.1678 | 0.065 |
| H24 | 0.5434 | 0.6660 | 0.1593 | 0.065 |
| H2B | 0.3346 | 0.6751 | 0.0687 | 0.063 |
| H3B1 | 0.7229 | 0.6430 | 0.0564 | 0.098 |
| H3B2 | 0.5661 | 0.5947 | 0.0036 | 0.098 |
| H3B3 | 0.6762 | 0.5420 | 0.0616 | 0.098 |
| H4B1 | 0.7401 | 0.5384 | 0.1655 | 0.070 |
| H4B2 | 0.5084 | 0.4870 | 0.1670 | 0.070 |
| H6B | 0.9374 | 0.4941 | 0.2563 | 0.057 |
| H7B | 0.9976 | 0.4915 | 0.3639 | 0.076 |
| H9B | 0.3675 | 0.5935 | 0.3720 | 0.072 |
| H10B | 0.3073 | 0.5961 | 0.2644 | 0.059 |
| H11C | 0.4196 | 0.5376 | 0.4684 | 0.084 |
| H11D | 0.5359 | 0.6311 | 0.4672 | 0.084 |
| H14B | 0.5506 | 0.6259 | 0.6788 | 0.086 |
| H15B | 0.8888 | 0.5506 | 0.7102 | 0.087 |
| H16B | 1.0857 | 0.4799 | 0.6373 | 0.093 |
| H17B | 0.9445 | 0.4845 | 0.5330 | 0.084 |
| H18D | 0.3710 | 0.4416 | 0.8019 | 0.088 |
| H18E | 0.5779 | 0.5006 | 0.7870 | 0.088 |
| H18F | 0.3408 | 0.5070 | 0.7456 | 0.088 |
| H1W | 0.594(8) | 0.434(6) | 0.933(4) | 0.087 |
| H2W | 0.806(13) | 0.391(6) | 0.935(4) | 0.087 |
| H1A2 | 0.2212 | 0.3166 | −0.0108 | 0.087 |
| H1A3 | 0.4130 | 0.3759 | 0.0059 | 0.087 |
| H1B1 | −0.0063 | 0.5452 | −0.0021 | 0.087 |
| H1B2 | 0.2266 | 0.5630 | −0.0163 | 0.087 |

Example 9

Synthesis of (S)-2-[4-(2-fluorobenzyloxy)benzylamino]propanamide Methanesulfonate Form A by Salification of (S)-2-[4-(2-fluorobenzyloxy)benzylamino]propanamide with Methanesulfonic Acid in Acetone, Comparison with the Product Obtained According to a Prior Art Method and its Purification by Slurring in Acetone a) Synthesis in Acetone A suspension of (S)-2-[4-(2-fluorobenzyloxy)benzylamino]propanamide (127.6 kg, 422.03 mol; HPLC purity 99.4 (Area %); enantiomeric ratio S:R=99.8:02, Example 26A of WO 2009/074478; residual solvents; toluene 300 ppm and methanol 50 ppm, (Example 18); alkyl methanesulfonates lower than 0.05 ppm (LOD), (Example 19), prepared as in Example 2a of WO 2009/074478, in acetone (800 kg) is heated under nitrogen and mechanical stirring to reflux at 58+/−3° C. and kept under these conditions until clear solution. The solution is filtered through a GAF filter and the filter is washed with 20 kg of acetone. Methanesulfonic acid (40.8 kg, 424.5 mol) is added to the warm (58+/−3° C.) solution over not less than 30 min. leading to the immediate precipitation of a solid compound. The dropping funnel is washed with 30 kg of acetone and the suspension is stirred for 60 minutes at 56+/−3° C. The reaction mixture is cooled to 20+/−3° C. over two hours and then stirred at the same temperate for 2 hours. The insoluble product is isolated by filtration and washed with acetone (85 kg). The wet product is dried at 40+/−2° C. under vacuum (about 20 mbar) for 16 hours to provide (S)-2-[4-(2-fluorobenzyloxy)benzylamino]propanamide methanesulfonate (Form A 165.8 kg; 98.6% yield).

HPLC purity: 99.8 (Area %) (Example 25A of WO 2009/074478);

HPLC enantiomeric ratio: S:R=99.5:0.5 (Example 26A of WO 2009/074478);

K.F.: water content 0.1% by weight (Example 17);

Residual solvents: toluene and methanol less than 6 ppm (LOD), acetone 1,023 ppm (Example 18);

Alkyl methanesulfonates: MMS, EMS and IMS lower than 0.05 ppm (LOD) (Example 19);

DSC endothermic melting peak at 243.1±0.2° C. (ΔH=132.1±4.5 J/g), (Example 20);

TGA: the product does not lose weight up to 240° C. The weight loss above this temperature is due to substance decomposition (Example 20);

High resolution NMR (Example 21): the $^1$H NMR spectrum in CD$_3$CN of (S)-2-[4-(2-fluorobenzyloxy)benzylamino]propanamide methanesulfonate, form A, is fully consistent with the given structure and is found to be identical to that of form H (Example 1a). In the following Table 10, NMR data for all protons are reported.

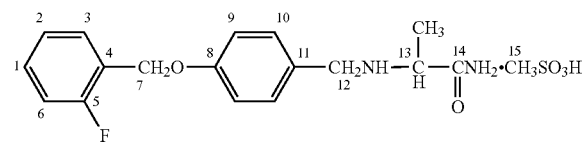

TABLE 10

| H | Chemical Shift (ppm) | Multiplicity | Coupling constant (Hz) |
|---|---|---|---|
| 1 | 7.43 | multiplet | |
| 2 | 7.25 | triplet | 7.0 |
| 3 | 7.57 | dt | 7.0, 1.1 |
| 6 | 7.19 | dd | 7.0; 6.0 |
| 7 | 5.21 | singlet | |
| 9 | 7.08 | Part A of an AB system | 8.7 |
| 10 | 7.48 | Part B of an AB system | 8.7 |
| 12 | 4.04; 4.16 | AB system | 12 |
| 13 | 3.88 | quartet | 7.0 |
| 15 | 2.51 | singlet | |
| CH$_3$—CH | 1.55 | douplet | 7.0 |
| CONH$_2$ | 6.15; 6.70 | singlet | |

Solid Stats CP/MAS NMR (Example 21): the solid state $^1$H CP/MAS spectrum of (S)-2-[4-(2-fluorobenzyloxy)benzylamino]propanamide methanesulfonate form A shows two broad signals, the first at 1.00-1.50 ppm and the second one between 2.00 and 6.00 ppm.

Figure 9:
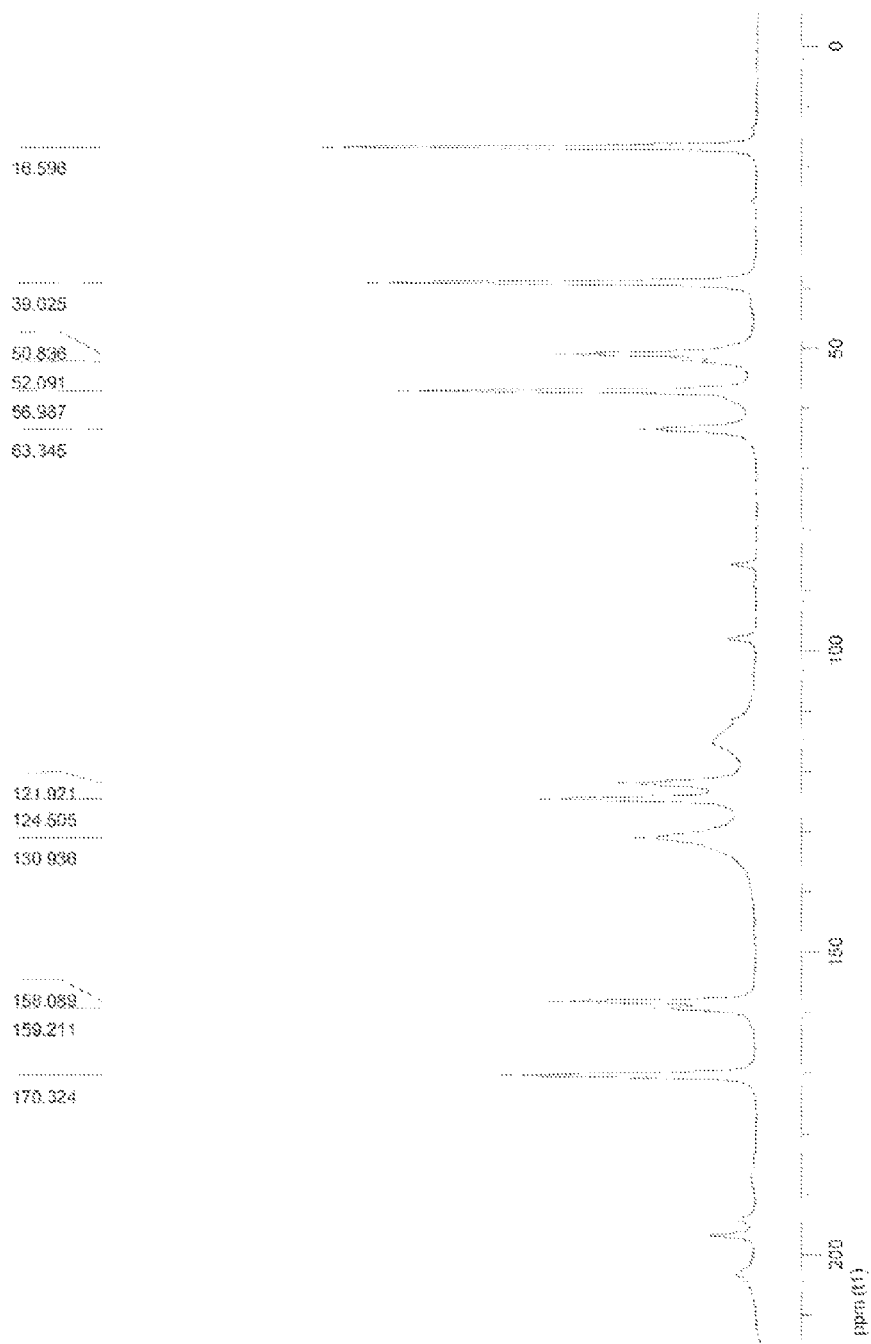
FIG. 9—$^{13}$C CP/MAS NMR of ralfinamide methanesulfonate form A; horizontal acix; chemical shift ppm; vertical axis relative intensity.

The $^{13}$C CP/MAS spectrum of (S)-2-[4-(2-fluorobenzyloxy)benzylamino]propanamide methanesulfonate shows the chemical shifts (ppm) resonances described here below in Table 11. The full spectrum is reported in FIG. 9.

TABLE 11

| $^{13}$C CP/MAS chemical shifts (ppm) | | | | |
|---|---|---|---|---|
| C-1; C-2; C-3; C-5; C-6 | C-4 | C-7 | C-8 | Not attributed C signal |
| 115.0; 121.9; 124.5 | 159.2 158.1 | 63.35 | 170.3 | 85.0 |

| C-9 | C-10 | C-11 | C-12 | C-13 | C-14 | C-15 | Me—C-13 |
|---|---|---|---|---|---|---|---|
| 112.0 | 130.9 | 98.0 | 50.8 52.1 | 57.0 | 185.0 190.8 205.0 | 39.0 | 16.6 |

PXRD Analysis: in the following Table 12 is reported the observed PXRD pattern of the anhydrous polymorph form A (powder) determined by using the instrument and conditions described in Example 22.

The experimental results are in agreement with the crystallographic parameters calculated by using the data of the SCXRD analysis.

TABLE 12

Observed and calculated PXRD patterns for form A

| | | | 2θ | | |
|---|---|---|---|---|---|
| h | k | l | (obs) | (calc) | Rel. Int. |
| 1 | 1 | 0 | 6.93 | 6.903 | 1.7 |
| 2 | 0 | 0 | 7.80 | 7.793 | 23.0 |
| 2 | 1 | 0 | 9.66 | 9.659 | 3.0 |
| 0 | 2 | 0 | 11.38 | 11.409 | 2.9 |
| 1 | 2 | 0 | 12.04 | 12.060 | 10.4 |
| 3 | 1 | 0 | 13.02 | 13.023 | 10.4 |
| 2 | 2 | 0 | 13.82 | 13.831 | 7.0 |
| 4 | 0 | 0 | 15.60 | 15.622 | 21.0 |
| 3 | 2 | 0 | 16.36 | 16.370 | 8.8 |
| 4 | 1 | 0 | 16.62 | 16.641 | 3.8 |
| 1 | 1 | 1 | 17.52 | 17.450 | 6.7 |
| 2 | 0 | 1 | 17.83 | 17.826 | 7.2 |
| 2 | 1 | 1 | 18.75 | 18.728 | 16.6 |
| 4 | 2 | 0 | 19.35 | 19.387 | 28.5 |
| 0 | 2 | 1 | 19.70 | 19.701 | 9.9 |
| 5 | 1 | 0 | 20.34 | 20.390 | 100.0 |
| 3 | 1 | 1 | 20.69 | 20.690 | 20.2 |
| 2 | 2 | 1 | 21.20 | 21.215 | 13.0 |
| 5 | 2 | 0 | 22.69 | 22.703 | 22.5 |
| 0 | 4 | 0 | 22.95 | 22.934 | 26.2 |
| 3 | 2 | 1 | | 22.973 | |
| 4 | 1 | 1 | | 23.169 | |
| 1 | 4 | 0 | 23.23 | 23.271 | 15.8 |
| 4 | 3 | 0 | | 23.278 | |
| 6 | 0 | 0 | 23.50 | 23.525 | 5.1 |
| 0 | 3 | 1 | | 23.542 | |
| 2 | 3 | 1 | 24.80 | 24.834 | 5.1 |
| 4 | 2 | 1 | 25.24 | 25.241 | 2.0 |
| 3 | 4 | 0 | 25.8056 | 25.819 | 10.1 |
| 5 | 1 | 1 | 26.01 | 26.03 | 3.6 |
| 5 | 2 | 1 | 27.84 | 27.902 | 4.7 |
| 7 | 1 | 0 | 28.07 | 28.124 | 3.1 |
| 6 | 0 | 1 | 28.55 | 28.585 | 4.8 |
| 6 | 1 | 1 | 29.16 | 29.171 | 10.3 |
| 6 | 3 | 0 | | 29.259 | |
| 2 | 5 | 0 | 29.82 | 29.858 | 1.9 |
| 7 | 2 | 0 | | 29.876 | |
| 5 | 3 | 1 | 30.77 | 30.79 | 11.0 |
| 8 | 0 | 0 | 31.50 | 31.544 | 4.7 |
| 7 | 0 | 1 | 31.95 | 31.995 | 2.0 |
| 4 | 4 | 1 | | 32.302 | |
| 0 | 0 | 2 | 32.38 | 32.338 | 1.0 |

TABLE 12-continued

Observed and calculated PXRD patterns for form A

| | | | 2θ | | |
|---|---|---|---|---|---|
| h | k | l | (obs) | (calc) | Rel. Int. |
| 7 | 1 | 1 | | 32.525 | |
| 2 | 0 | 2 | 33.37 | 33.314 | 1.5 |
| 1 | 5 | 1 | | 33.341 | |
| 2 | 1 | 2 | 33.96 | 33.826 | 0.8 |
| 2 | 5 | 1 | | 34.057 | |
| 1 | 2 | 2 | 34.61 | 34.63 | 0.9 |
| 5 | 5 | 0 | 34.95 | 35.038 | 1.2 |
| 8 | 1 | 1 | 36.02 | 36.048 | 1.3 |
| 7 | 3 | 1 | 36.46 | 36.521 | 3.1 |
| 8 | 2 | 1 | 37.38 | 37.467 | 2.0 |
| 5 | 0 | 2 | 38.04 | 38.076 | 0.7 |
| 9 | 1 | 1 | 39.66 | 39.711 | 3.3 | h,k,l reflection indexes b) Synthesis in 2-propanol (S)-2-[4-(2-fluorobenzyloxy)benzylamino]propanamide methanesulfonate, prepared as described in Example 3a) of WO 2009/074478 from (S)-2-[4-(2-fluorobenzyloxy)benzylamino]propanamide [HPLC purity 99.4 (Area %). Example 25A of WO 2009/074478; enantiomeric ratio S:R=99.8:0.2, Example 26A of WO 2009/074478; residual solvents: toluene 300 ppm and methanol 50 ppm. Example 18; alkyl methanesulfonates: lower than 0.05 ppm (LOD), and IMS 0.15 ppm, Example 19), prepared as in Example 2a of WO 2009/0744781] and methanesulfonic acid in 2-propanol, shows the same physical characteristics (PXRD, DSC, TGA, $^{13}$C-CP/MAS NMR) as per the above Example 9a) and the following additional characteristics:

HPLC purity: 99.8 (Area %) (Example 25A of WO 2009/074478);

HPLC enantiomeric ratio: S:R=99.5:0.5 (Example 26A of WO2009/074478);

K.F.: water content 0.1% by weight (Example 17);

Residual solvents: toluene and methanol less than 6 ppm (LOD), 2-propanol 1,300 ppm (Example 18);

Alkyl methanesulfonates: MMS, EMS lower than 0.05 ppm (LOD), and IMS 0.15 ppm (Example 19).

c) Slurring in Acetone (S)-2-[4-(2-fluorobenzyloxy)benzylamino]propanamide methanesulfonate form A (168.2 g, 0.422 mol; HPLC purity: 99.8 (Area %). Example 25A of WO 2009/074478; enantiomeric ratio: S:R=99.5:0.5. Example 26A of WO 2009/074478; K.F.: water content 0.1%. Example 17: residual solvents: 2-propanol 1,300 ppm. Example 18: alkyl methanesulfonates: MMS, EMS, lower than 0.05 ppm (LOD) and IMS 0.15 ppm, Example 19), prepared as in Example 9b, is added under stirring at room temperature to acetone (820 g). The heterogeneous mixture is stirred at room temperature for 24 hours and then filtered and the crystals washed with acetone (80 ml). The wet products is dried at 40+/−2° C. under vacuum (about 20 mbar) for 16 hours to provide S)-2-[4-(2-fluorobenzyloxy)benzylamino]propanamide methanesulfonate, Form A, (161.5 g, 96% yield) having the following characteristics:

HPLC purity: 100.0 (Area %) (Example 25A of WO 2009/074478);

HPLC enantiomeric purity: 100% (Example 26A of WO 2009/074478);

K.F.: water content 0.05% by weight (Example 17);

Residual solvents; acetone 1015 ppm, 2-propanol less than 6 ppm (LOD) (Example 18);

Alkyl methanesulfonate: MMS, EMS and IMS lower than 0.05 ppm (LOD) (Example 19).

The product shows the same physical characteristics (PXRD, DSC, TGA, $^{13}$C-CP-MAS NMR) of (S)-2-[4-(2-fluorobenzyloxy)benzylamino]propanamide methansulfonate prepared according to Example 9a.

Example 10

Single crystal preparation of (S)-2-[4-(2-fluorobenzyloxy)benzylamino]propanamide methanesulfonate form A by crystallization of (S)-2-[4-(2-flouorobenzyloxy)benzylamino]propanamide methanesulfonate form A from water (S)-2-[4-(2-fluorobenzyloxy)benzylamino]propanamide methanesulfonate form A obtained according to Example 9a is dissolved in water at 20° C. and crystals are grown by slow evaporation of water in form of colorless needles which are recovered by filtration and dried at 20° C. for 12 hours.

Figure 2:
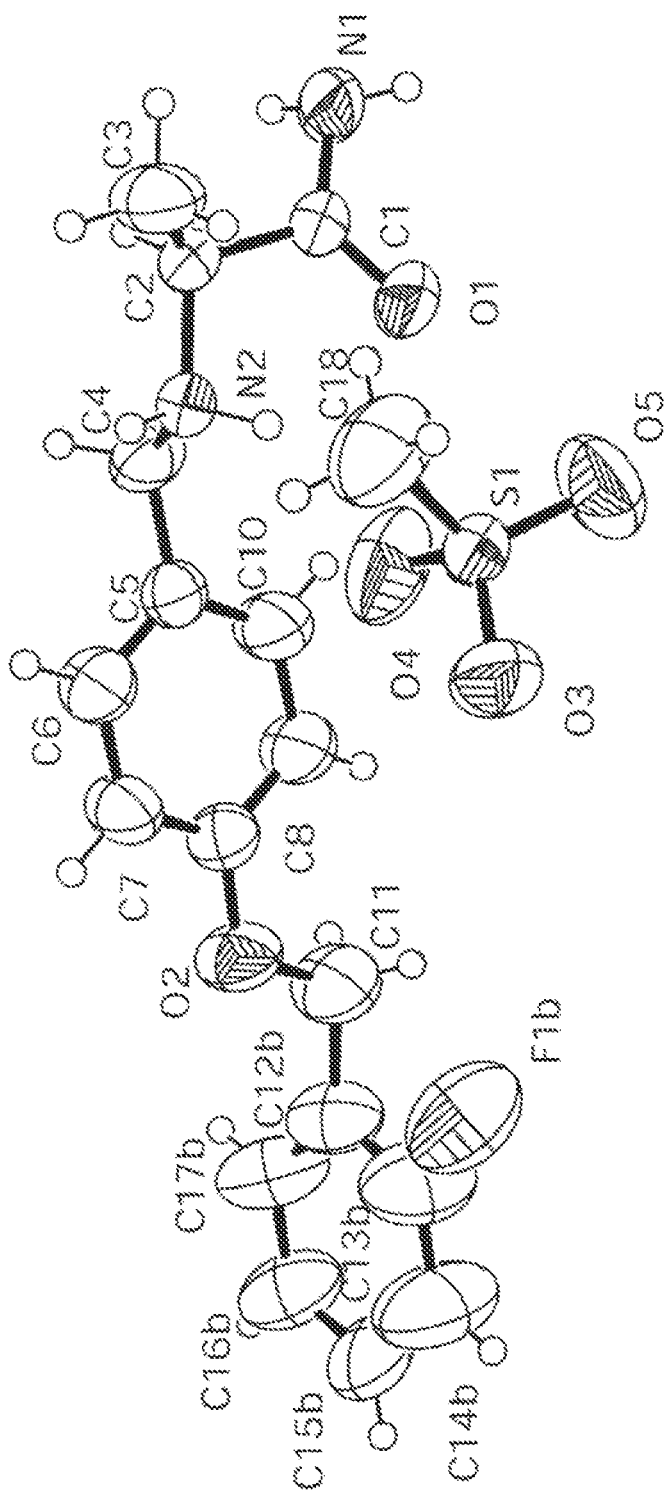
FIG. 2 depicts the symmetry independent molecular structure of form A as derived by single crystal X-ray diffraction (atomic coordinates based on Tables 13-17). Only one possible conformation of the terminal aromatic ring (disordered over two possible orientations) and of the fluorine atom (disordered over two positions for each orientation of the aromatic ring) is shown for clarity.
Figure 3:
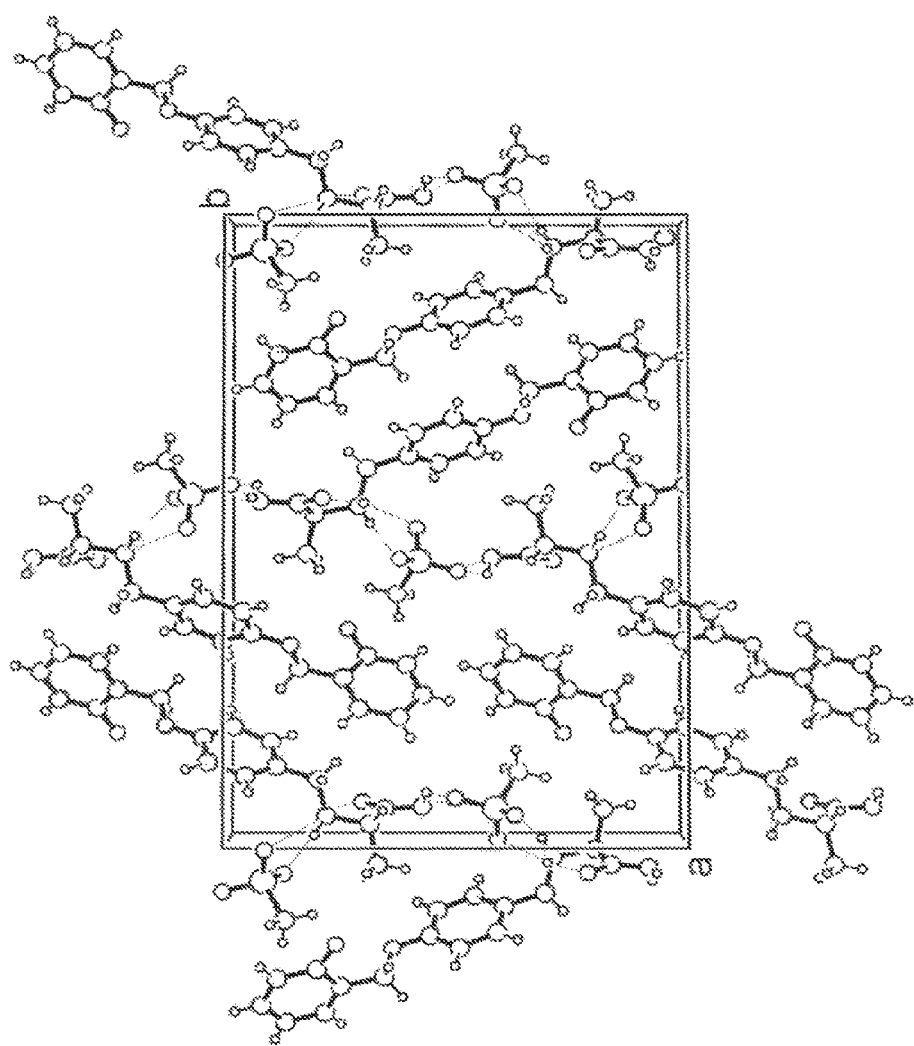
FIG. 3 depicts the molecular packing of form A, projected onto the ab plane of the structure (unit cell size and symmetry based on Table 4 and atomic coordinates based on Tables 13-17). Only one possible conformation of the terminal aromatic ring (disordered over two possible orientations) and of the fluorine atom (disordered over two positions for each orientation of the aromatic ring) is shown for clarity. Light hues point out the hydrogen bond system.
Figure 4:
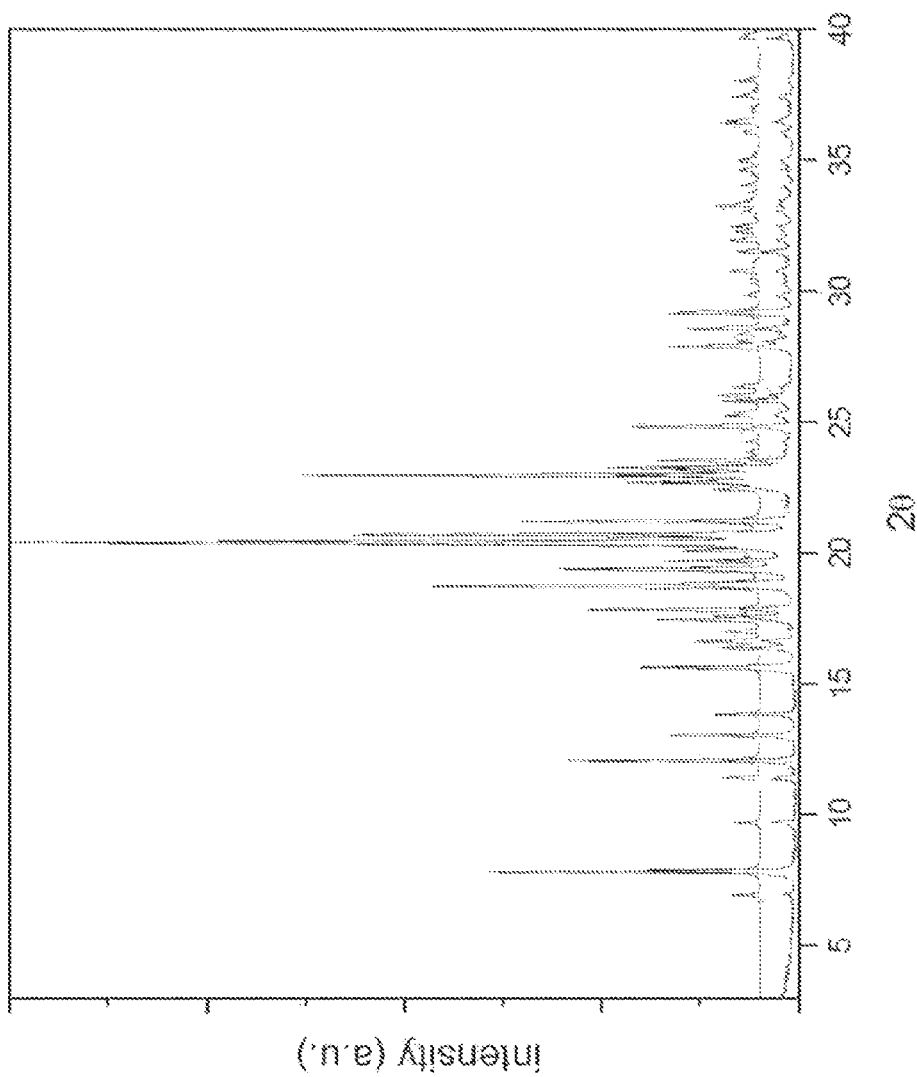
FIG. 4 is a plot of calculated versus experimental X-ray powder diffraction pattern (PXRD) for form A; horizontal, axis (2θ) in degrees; vertical axis; intensity (a.u.); upper plot calculated powder pattern; lower plot experimental powder pattern.

A crystal having approximate dimensions of 0.55×0.09×0.08 mm is mounted on a glass fiber in order to perform single crystal X-ray diffraction analysis. Data are collected with Cu K$_α$ radiation (λ=1.54178 Å) on a modified Siemens AED diffractometer equipped with a graphite monochromator (Belletti, D., Cantoni, A. & Pasquinelli, G. (1993). AED Report 1/93 Centro di Studio per la Strutturistica Diffrattometrica del CNR, Parma, Italy). The structure is solved with SIR97 and refined with SHELX97L. Hydrogen atoms are located by difference Fourier maps and then refined in constrained positions, with the exception of the hydrogen atoms of the aminic and amidic groups, for which only a restrain on the bond length is applied. The refinement was performed with anisotropic displacement parameters for all the non-hydrogen atoms. The C12-C17 (reference is made to FIG. 2) terminal aromatic ring (refined as rigid body) is found to be disordered over two positions with occupancies 0.65 and 0.35 respectively. For each ring the F1 fluorine atom is disordered at the same probability level (50%) over two positions, implying a rotation of 180° around the C11-C12 bond of the C12-C17 ring. This leads, for the resulting four disordered fluorine positions, to occupancies of 0.325, 0.325, 0.175 and 0.175 respectively. Refinement of the absolute configuration confirms the S character of the ralfinamide moiety. The crystallographic parameters determined in the SCXRD experiment are reported in Tables 2 (where the crystallographic parameters are compared with those of crystalline form H) and 9-13 (where the numbering of the atoms is in conformity with FIG. 2). The molecular structure and the crystal packing of ralfinamide methanesulfonate form A are reported in FIGS. 2 and 3, respectively. Both the drawings are obtained with ORTEP. In both plots only a possible configuration of the disordered (C12-C17) aromatic ring is shown for clarity: In FIG. 2 the a.d.p. ellipsoids are shown at the 50% probability level.

TABLE 13 refers to FIG. 2
Fractional Atomic Coordinates, Equivalent Isotropic Atomic Displacement Parameters ($U_{eq}$, Å$^2$) and Structure Occupancy Factor for form A

| atom | x | y | z | $U_{eq}$* | Occupancy** |
|---|---|---|---|---|---|
| S1 | −0.05377(4) | 0.4144(6) | 0.39167(17) | 0.0579(3) | |
| F1A | 0.2296(13) | 0.7631(18) | 0.238(5) | 0.156(4) | 0.175 |
| F2A | 0.2793(13) | 0.746(2) | 1.067(5) | 0.156(4) | 0.175 |
| F1B | 0.1620(6) | 0.7616(9) | 0.400(3) | 0.156(4) | 0.325 |
| F2B | 0.3138(7) | 0.7351(11) | 0.891(4) | 0.156(4) | 0.325 |
| O1 | 0.0507(3) | 0.2117(2) | 0.4828(6) | 0.1070(15) | |
| O2 | 0.18230(14) | 0.6416(2) | 0.8342(7) | 0.0830(10) | |
| O3 | −0.0708(2) | 0.5021(2) | 0.3684(7) | 0.0994(12) | |
| O4 | −0.00133(18) | 0.4097(4) | 0.5407(8) | 0.1133(15) | |
| O5 | −0.0487(2) | 0.3741(3) | 0.1618(8) | 0.1063(13) | |
| N1 | 0.0457(3) | 0.0764(2) | 0.6177(7) | 0.0906(15) | |
| N2 | 0.03697(14) | 0.28588(18) | 0.9077(6) | 0.0523(7) | |
| C1 | 0.0424(2) | 0.1599(2) | 0.6460(7) | 0.0610(9) | |
| C2 | 0.02414(17) | 0.1907(2) | 0.8948(7) | 0.0545(8) | |
| C3 | −0.0400(2) | 0.1729(3) | 0.9485(11) | 0.0852(15) | |
| C4 | 0.0977(2) | 0.3033(3) | 0.9877(9) | 0.0695(11) | |
| C5 | 0.11829(17) | 0.3946(2) | 0.9424(7) | 0.0580(9) | |
| C6 | 0.1057(2) | 0.4603(3) | 1.0943(10) | 0.0780(13) | |
| C7 | 0.1275(2) | 0.5432(3) | 1.0505(10) | 0.0780(13) | |
| C8 | 0.16302(18) | 0.5583(3) | 0.8592(9) | 0.0640(9) | |
| C9 | 0.1775(3) | 0.4931(3) | 0.7050(10) | 0.0881(16) | |
| C10 | 0.1538(3) | 0.4103(3) | 0.7499(11) | 0.0920(16) | |
| C11 | 0.2216(3) | 0.6582(4) | 0.6385(14) | 0.107(2) | |
| C12A | 0.2441(6) | 0.7433(6) | 0.637(3) | 0.0900(19) | 0.35 |
| C13A | 0.2639(7) | 0.7721(10) | 0.861(3) | 0.127(4) | 0.35 |
| C14A | 0.2919(7) | 0.8516(10) | 0.880(3) | 0.159(6) | 0.35 |
| C15A | 0.3002(7) | 0.9021(7) | 0.675(3) | 0.120(4) | 0.35 |
| C16A | 0.2804(6) | 0.8733(7) | 0.452(3) | 0.111(3) | 0.35 |
| C17A | 0.2524(6) | 0.7939(7) | 0.433(2) | 0.115(3) | 0.35 |
| C12B | 0.2371(3) | 0.7537(3) | 0.6472(17) | 0.0900(19) | 0.65 |
| C13B | 0.2045(3) | 0.8041(5) | 0.4882(16) | 0.127(4) | 0.65 |
| C14B | 0.2185(4) | 0.8906(4) | 0.4570(16) | 0.159(6) | 0.65 |
| C15B | 0.2651(4) | 0.9267(3) | 0.5848(17) | 0.120(4) | 0.65 |
| C16B | 0.2977(3) | 0.8763(4) | 0.7438(15) | 0.111(3) | 0.65 |
| C17B | 0.2837(3) | 0.7898(4) | 0.7750(16) | 0.115(3) | 0.65 |
| C18 | −0.1092(3) | 0.3651(5) | 0.5651(15) | 0.114(2) | |

*Equivalent isotropic $U_{eq}$ defined as one third of the trace of the orthogonalized $U_{ij}$ tensor
**Fully occupied (1.00) if not indicated

TABLE 14 refers to FIG. 2
Anisotropic Atomic Displacement Parameters (U*, Å$^2$) for form A

| atom | $U_{11}$ | $U_{22}$ | $U_{33}$ | $U_{23}$ | $U_{13}$ | $U_{12}$ |
|---|---|---|---|---|---|---|
| S1 | 0.0743(5) | 0.0518(5) | 0.0475(5) | 0.0049(4) | 0.0021(4) | 0.0025(4) |
| F1A | 0.143(7) | 0.150(7) | 0.175(10) | 0.054(9) | −0.023(6) | 0.035(6) |
| F2A | 0.143(7) | 0.150(7) | 0.175(10) | 0.054(9) | −0.023(6) | 0.035(6) |
| F1B | 0.143(7) | 0.150(7) | 0.175(10) | 0.054(9) | −0.023(6) | 0.035(6) |
| F2B | 0.143(7) | 0.150(7) | 0.175(10) | 0.054(9) | −0.023(6) | 0.035(6) |
| O1 | 0.208(5) | 0.0650(19) | 0.0476(16) | 0.0043(13) | 0.031(2) | −0.011(2) |
| O2 | 0.0845(19) | 0.0652(16) | 0.099(3) | 0.0057(18) | 0.0272(19) | −0.0162(14) |
| O3 | 0.158(3) | 0.0547(17) | 0.085(2) | 0.0041(17) | 0.026(3) | 0.0130(18) |
| O4 | 0.100(3) | 0.156(4) | 0.084(3) | 0.040(3) | −0.020(2) | −0.011(3) |
| O5 | 0.134(3) | 0.104(3) | 0.080(2) | −0.036(2) | −0.004(2) | 0.025(2) |
| N1 | 0.170(5) | 0.0518(18) | 0.050(2) | −0.0028(18) | 0.022(3) | 0.012(2) |
| N2 | 0.0672(17) | 0.0488(15) | 0.0409(15) | 0.0029(13) | −0.0022(15) | −0.0046(12) |
| C1 | 0.092(3) | 0.0490(17) | 0.0421(18) | 0.0034(14) | 0.0034(18) | −0.0029(16) |
| C2 | 0.075(2) | 0.0439(16) | 0.0449(17) | 0.0056(16) | 0.0038(18) | −0.0014(14) |
| C3 | 0.095(3) | 0.060(2) | 0.100(4) | −0.007(2) | 0.031(3) | −0.021(2) |
| C4 | 0.078(2) | 0.060(2) | 0.070(3) | 0.017(2) | −0.019(2) | −0.0106(18) |
| C5 | 0.0620(18) | 0.058(2) | 0.054(2) | 0.0039(16) | −0.0106(16) | −0.0064(15) |
| C6 | 0.081(3) | 0.077(3) | 0.076(3) | −0.003(3) | 0.030(3) | −0.023(2) |
| C7 | 0.093(3) | 0.064(2) | 0.077(3) | −0.014(2) | 0.029(2) | −0.015(2) |
| C8 | 0.0644(19) | 0.0606(19) | 0.067(2) | 0.0041(19) | 0.003(2) | −0.0107(16) |
| C9 | 0.116(4) | 0.072(3) | 0.076(3) | 0.000(2) | 0.045(3) | −0.019(3) |
| C10 | 0.130(4) | 0.064(3) | 0.082(3) | −0.006(3) | 0.037(3) | −0.017(3) |
| C11 | 0.124(4) | 0.089(3) | 0.107(5) | 0.003(4) | 0.040(4) | −0.029(3) |
| C12A | 0.072(3) | 0.071(3) | 0.127(5) | 0.006(4) | 0.035(3) | −0.011(3) |
| C13A | 0.105(6) | 0.095(5) | 0.181(12) | 0.011(7) | −0.009(7) | −0.033(5) |

TABLE 14-continued refers to FIG. 2
Anisotropic Atomic Displacement Parameters (U*, Å$^2$) for form A

| atom | U$_{11}$ | U$_{22}$ | U$_{33}$ | U$_{23}$ | U$_{13}$ | U$_{12}$ |
|---|---|---|---|---|---|---|
| C14A | 0.163(10) | 0.097(6) | 0.216(17) | 0.041(9) | −0.041(11) | −0.042(6) |
| C15A | 0.160(10) | 0.097(6) | 0.103(7) | 0.030(6) | −0.024(6) | −0.055(6) |
| C16A | 0.093(5) | 0.087(5) | 0.153(9) | 0.035(6) | 0.037(6) | −0.001(4) |
| C17A | 0.092(5) | 0.072(4) | 0.181(10) | 0.026(6) | 0.020(6) | 0.000(4) |
| C12B | 0.072(3) | 0.071(3) | 0.127(5) | 0.006(4) | 0.035(3) | −0.011(3) |
| C13B | 0.105(6) | 0.095(5) | 0.181(12) | 0.011(7) | −0.009(7) | −0.033(5) |
| C14B | 0.163(10) | 0.097(6) | 0.216(17) | 0.041(9) | −0.041(11) | −0.042(6) |
| C15B | 0.160(10) | 0.097(6) | 0.103(7) | 0.030(6) | −0.024(6) | −0.055(6) |
| C16B | 0.093(5) | 0.087(5) | 0.153(9) | 0.035(6) | 0.037(6) | −0.001(4) |
| C17B | 0.092(5) | 0.072(4) | 0.181(10) | 0.026(6) | 0.020(6) | 0.000(4) |
| C18  | 0.101(4) | 0.131(5) | 0.111(5) | 0.033(5) | 0.004(4) | −0.020(4) |

*the anisotropic displacement parameter exponent takes the form: $-2\pi^2$ (h$^2$a*$^2$U$_{11}$ + k$^2$b*$^2$U$_{22}$ + ... + 2hka*b*U$_{12}$)

TABLE 15 refers to FIG. 2
Bond Lengths (Å) for form A

| S1-O3 | 1.419(3) | C6-C7 | 1.398(6) |
|---|---|---|---|
| S1-O5 | 1.423(4) | C7-C8 | 1.352(6) |
| S1-O4 | 1.450(4) | C8-C9 | 1.364(7) |
| S1-C18 | 1.758(6) | C9-C10 | 1.415(6) |
| F1A-C17A | 1.29(3) | C11-C12A | 1.415(10) |
| F2A-C13A | 1.26(3) | C11-C12B | 1.522(7) |
| F1B-C13B | 1.27(2) | C12A-C13A | 1.3900* |
| F2B-C17B | 1.26(2) | C12A-C17A | 1.3900* |
| O1-C1 | 1.223(5) | C15A-C14A | 1.3900* |
| O2-C8 | 1.371(5) | C14A-C15A | 1.3900* |
| O2-C11 | 1.427(7) | C15A-C16A | 1.3900* |
| N1-C1 | 1.306(5) | C16A-C17A | 1.3900* |
| N2-C4 | 1.473(5) | C12B-C13B | 1.3900* |
| N2-C2 | 1.507(4) | C12B-C17B | 1.3900* |
| C1-C2 | 1.516(5) | C13B-C14B | 1.3900* |
| C2-C3 | 1.511(6) | C14B-C15B | 1.3900* |
| C4-C5 | 1.512(5) | C15B-C16B | 1.3900* |
| C5-C6 | 1.352(6) | C16B-C17B | 1.3900* |
| C5-C10 | 1.358(7) | | |

*resulting from rigid body refinement of the C12-C17 disordered aromatic ring

TABLE 16 refers to FIG. 2
Bond angles (°) for form A

| O3-S1-O5 | 111.2(2) | F2A-C13A-C12A | 142(2) |
|---|---|---|---|
| O3-S1-O4 | 109.0(3) | F2A-C13A-C14A | 95(2) |
| O5-S1-O4 | 114.9(3) | C14A-C13A-C12A | 120.0* |
| O3-S1-C18 | 105.7(3) | C13A-C14A-C15A | 120.0* |
| O5-S1-C18 | 110.8(3) | C16A-C15A-C14A | 120.0* |
| O4-S1-C18 | 104.7(3) | C15A-C16A-C17A | 120.0* |
| C8-O2-C11 | 116.5(4) | F1A-C17A-C12A | 115(2) |
| C4-N2-C2 | 112.0(3) | F1A-C17A-C16A | 125(2) |
| O1-C1-N1 | 123.6(4) | C16A-C17A-C12A | 120.0* |
| O1-C1-C2 | 120.4(4) | C13B-C12B-C17B | 120.0* |
| N1-C1-C2 | 115.9(3) | C13B-C12B-C11 | 113.9(6) |
| N2-C2-C3 | 110.9(3) | C17B-C12B-C11 | 125.7(5) |
| N2-C2-C1 | 107.4(3) | F1B-C13B-C12B | 110.9(9) |
| C3-C2-C1 | 112.6(4) | F1B-C13B-C14B | 129.0(9) |
| N2-C4-C5 | 114.2(3) | C14B-C13B-C12B | 120.0* |
| C6-C5-C10 | 118.6(4) | C13B-C14B-C15B | 120.0* |
| C6-C5-C4 | 122.5(4) | C16B-C15B-C14B | 120.0* |
| C10-C5-C4 | 118.8(4) | C17B-C16B-C15B | 120.0* |
| C5-C6-C7 | 120.7(4) | F2B-C17B-C12B | 114(1) |
| C8-C7-C6 | 120.4(4) | F2B-C17B-C16B | 126(1) |
| C7-C8-C9 | 120.4(4) | C16B-C17B-C12B | 120.0 |
| C7-C8-O2 | 115.7(4) | F2A-C13A-C12A | 142(2) |
| C9-C8-O2 | 124.0(4) | F2A-C13A-C14A | 95(2) |
| C8-C9-C10 | 118.2(4) | C14A-C13A-C12A | 120.0* |
| C5-C10-C9 | 121.7(4) | C13A-C14A-C15A | 120.0* |
| C12A-C11-O2 | 113.5(9) | C16A-C15A-C14A | 120.0* |

TABLE 16-continued refers to FIG. 2
Bond angles (°) for form A

| O2-C11-C12B | 107.2(5) | C15A-C16A-C17A | 120.0* |
|---|---|---|---|
| C13A-C12A-C17A | 120.0* | F1A-C17A-C12A | 115(2) |
| C13A-C12A-C11 | 114.3(11) | F1A-C17A-C16A | 125(2) |
| C17A-C12A-C11 | 125.4(11) | C16A-C17A-C12A | 120.0* |

*resulting from rigid body refinement of the C12-C17 disordered aromatic ring

TABLE 17 refers to FIG. 2
H-atom Fractional Atomic Coordinates, Isotropic Atomic Displacement
Parameters (U$_{iso}$, Å$^2$) and Structure occupancy Factor for form A

| atom | x | y | z | U$_{iso}$ | Occupancy* |
|---|---|---|---|---|---|
| H11N | 0.071(3) | 0.067(4) | 0.731(10) | 0.12(3) | |
| H12N | 0.052(3) | 0.061(4) | 0.471(4) | 0.11(2) | |
| H21N | 0.042(2) | 0.299(3) | 0.756(10) | 0.070(13) | |
| H22N | 0.0093(16) | 0.310(3) | 1.012(8) | 0.049(10) | |
| H2 | 0.0483 | 0.1610 | 1.0156 | 0.065 | |
| H3A | −0.0495 | 0.1939 | 1.1069 | 0.128 | |
| H3B | −0.0471 | 0.1119 | 0.9416 | 0.128 | |
| H3C | −0.0642 | 0.2015 | 0.8311 | 0.128 | |
| H4A | 0.1241 | 0.2639 | 0.9050 | 0.083 | |
| H4B | 0.1005 | 0.2914 | 1.1594 | 0.083 | |
| H6 | 0.0824 | 0.4503 | 1.2294 | 0.094 | |
| H7 | 0.1174 | 0.5882 | 1.1535 | 0.094 | |
| H9 | 0.2023 | 0.5028 | 0.5740 | 0.106 | |
| H10 | 0.1628 | 0.3654 | 0.6449 | 0.110 | |
| H11A | 0.2543 | 0.6181 | 0.6472 | 0.128 | |
| H11B | 0.2011 | 0.6479 | 0.4876 | 0.128 | |
| B13A | 0.2584 | 0.7383 | 0.9975 | 0.152 | 0.175 |
| H14A | 0.3051 | 0.8709 | 1.0293 | 0.191 | 0.35 |
| H15A | 0.3189 | 0.9553 | 0.6880 | 0.144 | 0.35 |
| H16A | 0.2859 | 0.9071 | 0.3150 | 0.133 | 0.35 |
| H17A | 0.2392 | 0.7746 | 0.2832 | 0.138 | 0.175 |
| H13B | 0.1733 | 0.7799 | 0.4027 | 0.152 | 0.325 |
| H14B | 0.1968 | 0.9243 | 0.3507 | 0.191 | 0.65 |
| H15B | 0.2745 | 0.9846 | 0.5640 | 0.144 | 0.65 |
| H16B | 0.3289 | 0.9004 | 0.8293 | 0.133 | 0.65 |
| H17B | 0.3055 | 0.7560 | 0.8813 | 0.000(15) | 0.325 |
| H18A | −0.0999 | 0.3053 | 0.5876 | 0.172 | |
| H18B | −0.1463 | 0.3701 | 0.4828 | 0.172 | |
| H18C | −0.1118 | 0.3930 | 0.7195 | 0.172 | |

*Fully occupied (1.00) if not indicated

Example 11

Conversion of (S)-2-[4-(2-fluorobenzyloxy)benzylamino]propanamide Methanesulfonate Form H into the Form A (S)-2-[4(2-fluorobenzyloxy)benzylamino]propanamide methanesulfonate form H (40.7 g, 0.01 mol; HPLC purity: 99.8 (Area %), Example 25A of WO 2009/074478; HPLC enantiomeric purity: 100%, Example 26A of WO 2009/074478; K.F. water content 2.3%, (Example 17); residual solvents: toluene and methanol less than 6 ppm (LOD), (Example 18); alkyl methanesulfonates: MMS, EMS and IMS lower than 0.05 ppm (LOD), (Example 19), prepared as in Example 1a, is kept at 100° C. under vacuum (20 mmHg) for 4 hours to provide in quantitative yield (S)-2-[4-(2-fluorobenzyloxy)benzylamino]propanamide methanesulfonate form A (39.8 g, 0.100 mol), having the following characteristics:

HPLC purity: 99.8 (Area %) (Example 25A of WO 2009/074478);

HPLC enantiomeric purity: 100% (Example 26A of WO 2009/074478);

K.F.: water content 0.12% by weight (Example 17);

Residual solvents: toluene and methanol less than 6 ppm (LOD) (Example 18);

Alkyl methanesulfonate: MMS, EMS and IMS less than 0.05 ppm, (LOD) (Example 19);

DSC and TGA (Example 20). $^1$H-NMR spectra in CD$_3$CN, $^{13}$C CP/MAS NMR (Example 21) and PXRD analysis (Example 22) are fully consistent with those of the (S)-2-[4-(2-fluorobenzyloxy)benzylamino]propanamide methanesulfonate form A as reported in the Example 9a).

Example 12

Conversion of (R)-2-[4-(2-fluorobenzyloxy)benzylamino]propanamide Methanesulfonate Form H into the Form A (R)-2-[4-(2-fluorobenzyloxy)benzylamino]propanamide methanesulfonate form H (40.7 g, 0.10 mol; HPLC purity: 99.8 (Area %). Example 25A of WO 2009/074478; HPLC enantiomeric purity: 100%. Example 26B of WO 2009/074478; K.F. water content 2.3% by weight, (Example 17); residual solvents: toluene and methanol less than 6 ppm (LOD), (Example 18); alkyl methanesulfonates: MMS, EMS and IMS lower than 0.05 ppm (LOD), (Example 19), prepared as in Example 2, is kept at 100° C. under vacuum (20 mmHg) for 4 hours to provide in quantitative yield (R)-2-[4-(2-fluorobenzyloxy)benzylamino]propanamide methanesulfonate form A (39.8 g; 0.100 mol), having the following characteristics:

HPLC purity: 99.8 (Area %) (Example 25A of WO 2009/074478);

HPLC enantiomeric purity: 100% (Example 26B of WO 2009/074478);

K.F.: water content: 0.12% by weight (Example 17);

Residual solvents: toluene and methanol less than 6 ppm (LOD) (Example 18);

Alkyl methanesulfonates: MMS, EMS and IMS less than 0.05 ppm (LOD) (Example 19);

DSC and TGA (Example 20), $^1$H-NMR spectra in CD$_3$CN, $^{13}$C CP/MAS NMR (Example 21) and PXRD analysis (Example 22) are fully consistent with those of the (S)-2-[4-(2-fluorobenzyloxy)benzylamino]propanamide methanesulfonate form A as reported in the Example 9a.

Example 13 (Comparative Example)

Synthesis of (S)-2-[4-(2-fluorobenzyloxy)benzylamino]propanamide Hydrochloride by Salification of (S)-2-[4-(2-fluorobenzyloxy)benzylamino]propanamide with Hydrochloric Acid in Water HCl 1N (50 ml) is added at 20° C. in ten minutes to a stirred heterogeneous mixture of water (140 ml) and of (S)-2-[4-(2-fluorobenzyloxy)benzylamino]propanamide (5.0 g, 165 mmol); [HPLC purity 99.4 (Area %), Example 25A of WO 2009/074478; enantiomeric ratio S:R=99.8:02, Example 26A of WO 2009/074478; residual solvents: toluene 300 ppm and methanol 50 ppm (Example 18); alkyl methanesulfonates less than 0.05 ppm (LOD) (Example 19)], prepared as in Example 2a of WO 2009/074478.

During the addition the heterogeneous mixture becomes a solution from which crystals start to separate. The heterogeneous mixture is then stirred at 20° C. for 24 hrs and then filtered. The wet solid material is dried at ambient conditions to provide (S)-2-[4-(2-fluorobenzyloxy)benzylamino]propanamide hydrochloride in 68.2% yield.

K F: water content: 0.14% by weight (Example 17), chloride anion: 100%

Figure 14:
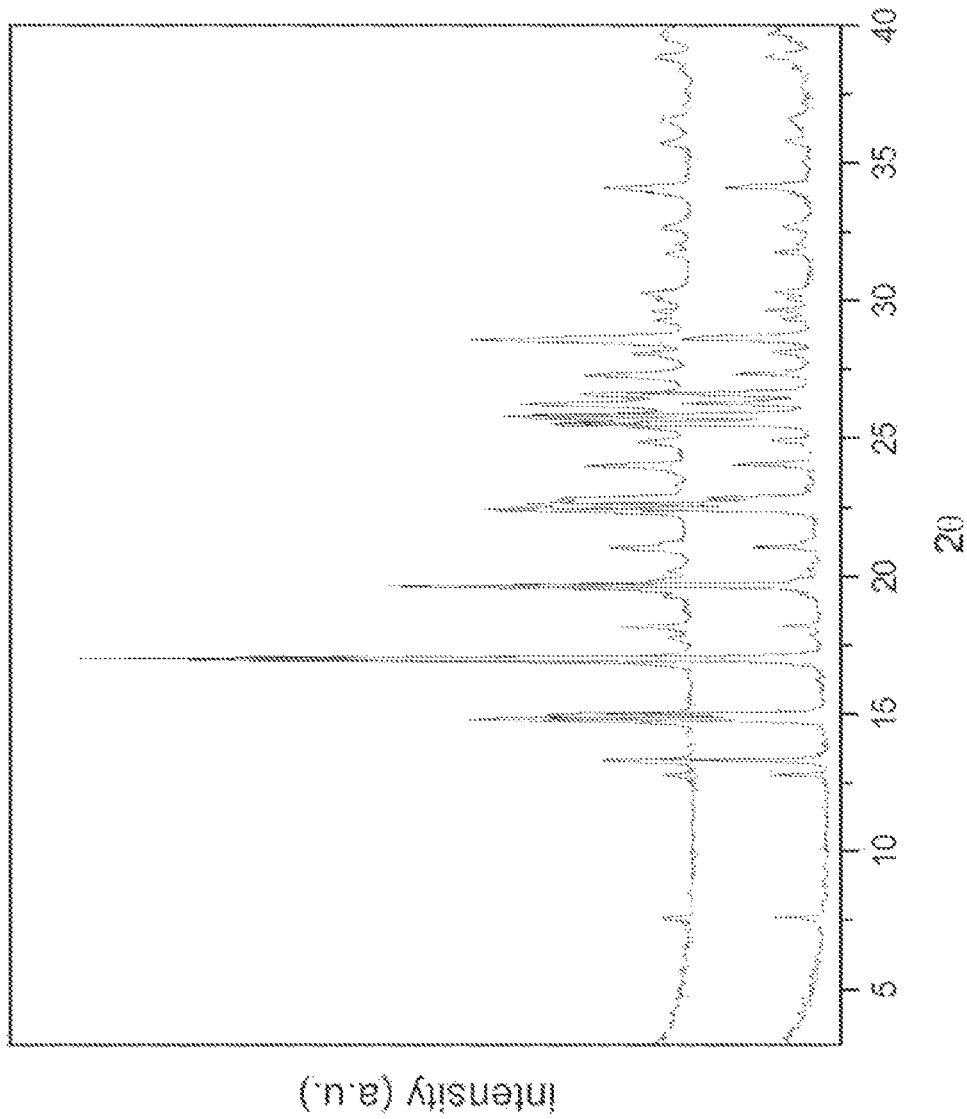

HPLC purity: 100.0% (Example 25A of WO 2009/074478);

HPLC enantiomeric purity: 100% (Example 26A of WO 2009/074478);

Residual solvents: toluene and methanol less than 6 ppm (LOD) (Example 18);

Alkyl methanesulfonates: MMS, EMS and IMS less than 0.05 ppm (LOD) (Example 19);

DSC: endotherm at 241° C. (Example 20); TGA: 0.2% (Example 20);

$^1$H-NMR spectrum is fully consistent with the (S)-2-[4-(2-fluorobenzyloxy)benzylamino]propanamide HCl structure. The PXRD pattern of both wet and dry samples is reported in FIG. 14.

Example 14

Preparation of Tablets Containing 40 and 80 mg (S)-2-[4-(2-fluorobenzyloxy)benzylamino]propanamide Methanesulfonate Form H Using Wet Granulation Ralfinamide methanesulfonate form H, prepared as per Example 1a, is processed with functional excipients by wet granulation and tabletting to obtain a homogeneous drug product comprising (per tablet):

ralfinamide methanesulfonate form H, 53.9 mg (equivalent to 40 mg free base) and 108.8 mg (equivalent to 80 mg free base), microcrystalline cellulose 95.3 mg and 190.6 mg, mannitol 42.0 mg and 84.0 mg, polyvinylpyrrolidone (PVP) 6.3 mg and 12.6 mg, crospovidone 10.5 and 21.0 mg magnesium stearate 2.1 mg and 4.2 mg and silicon dioxide 1.1 mg and 2.2 mg, respectively.

For a 1 kg batch a lab high shear mixer or another suitable apparatus is filled with ralfinamide methanesulfonate form H, microcrystalline cellulose, mannitol, and crospovidone. After mixing for 1-3 min an aqueous granulation solution of PVP (10% w/v) is added quantitatively to the powder mass. The wetted mixture is granulated with the simultaneous action of mixing pale and chopper for 2-5 min. The obtained wetted mass is passed through a 2.0 mm screen and dried for 0.5-1 hour in a tray oven or a fluidized bed dryer at 40°-60° C. After drying and screening through a 710 μm sieve with a suitable apparatus (e.g. an oscillating granulator) the granulate is added with colloidal silicon dioxide and magnesium stearate and mixed for 5 min. The lubricated granulate is compressed to tablets by using a rotary press equipped with suitable round punches. Alternatively, the granulation can be performed substituting the binding agent PVP with hydroxypropylmethylcellulose (HPMC).

Example 15

Preparation of Coated Tablets Containing 40 and 80 mg (S)-2-[4-(2-fluorobenzyloxy)benzylamino] propanamide Methanesulfonate Form H Using Aqueous Film-Coating Solution The tablets prepared according to Example 14 are coated with a conventional aqueous film coating liquid by using suitable pans or fluidized beds. The film coating has the following composition (per 40 mg and 80 mg tablets); hydroxypropyl methylcellulose 6 cps (HPMC) 6.0 mg and 12.0 mg, polyethyleneglycol 6000 (PEG 6000) 0.6 mg and 1.2 mg, titanium dioxide 0.9 mg and 1.8 mg, respectively. For 1 kg of the uncoated tablets the coating solution is prepared according to the following procedure: hydroxypropyl methylcellulose 6 cps, 28 g is stirred in approximately 150 g of hot purified water. Gold purified water, 290 g, is added with agitation. Upon complete dissolution of the hydroxypropyl methylcellulose, the solution is allowed to cool to ambient conditions. PEG 6000, 2.8 g, is added to the solution and dispersed. Titanium oxide, 4.3 g is then added and dispersed in the HPMC/PEG 6000 solution.

Uncoated tablet cores are placed in a perforated coating pan. The coating solution is applied using an air atomizing nozzle: 7.5 and 15.0 milligrams of film coating solids are applied per 40 and 80 mg tablet respectively.

Example 16

Preparation of Prolonged Drug Delivery Systems Containing 80, 160 mg and 320 mg (S)-2-[4-(2-fluorobenzyloxy)benzylamino]propanamide Methanesulfonate Form H a) Preparation of Prolonged Drug Delivery System by Swelling Matrices The monolithic matrix system contains ralfinamide methanesulfonate form H, different amounts of polymer (hydroxypropylmethylcellulose and polyacrylic acid) and additional ingredients such as glidants, lubricants and diluents. The target of drug delivery is to obtain a prolonged drug release up to approximately 80% within 12 or 24 hours.

A prolonged release formulation of tablets is the following: ralfinamide methanesulfonate form H 107.8 mg (equivalent to 80 mg free base), 215.6 mg (equivalent to 160 mg free base) and 431.2 mg (equivalent to 320 mg free base), Methocel K4M or K15M or K100M 64 mg, 128 mg and 256 mg, Carbopol 971 PNF 48 mg, 96 mg and 192 mg, magnesium stearate 14 mg, 28 mg and 56 mg and silicon dioxide 6 mg, 12 mg and 24 mg, respectively. The powder mixture is blended for 10 min. Magnesium stearate is sieved and added to the premixed powder and blended for additional 5 min. Thereafter, the final mixture is compressed into tablets using a suitable tabletting press.

b) The Preparation of Prolonged Drug Delivery System by Coated Pellets:

The coated multiparticulate system consists of pellets coated with a film controlling the drug delivery. They are filled in capsules or sachets.

The preparation of the coated pellets is performed as follows:

Manufacture of pellets by (i) extrusion and spheronization technology: ralfinamide methanesulfonate form H 107.8 mg (equivalent to 80 mg free base), 215.6 mg (equivalent to 160 mg free base) and 431.2 mg (equivalent to 320 mg free base), cellulose microcrystalline from 1:1 to 1:9 ratio with respect the drug dose, or (ii) layering on the sugar spheres a solution (or dispersion) containing ralfinamide methanesulfonate form H, a binder (PVP or HPMC 3-7%) and glidant/antiadherent agents (colloidal silica/talc. 0.1-0.5%/3-7%). The weight gain of material layered on the inert seeds is from 20 to 90% w/w.

Film-coating of pellets by using aqueous polymer dispersion such as ethylcellulose (Aquacoat) or acrylic resins (Eudragit RS and RL) 10, 20 and 80 mg, triethylcitrate 2, 4 and 8 mg and titanium dioxide 0.9, 1.8 and 3.6 mg, respectively.

Filling the coated pellets in hard capsules or sachets.

Alternatively the coated pellets are compacted into tablets using cellulose microcrystalline as a protecting agent to the compression stresses.

Example 17

Water Content Determination by Karl Fischer

The water content is determined via a coulometric Karl Fischer titration according to USP <921> Method Ic, Ph. Eur. 2.5.32.

Example 18

Residual Solvents Determination by Headspace Gas Chromatography (HS-GC)

The 6.0 European Pharmacopeia method, modified for the concentration of the reference and test solutions, is used for determination of the content of toluene, methanol, acetone and 2-propanol in the solid methanesulfonate salts of ralfinamide and of its R-enantiomer.

The determination is carried out according to the following conditions:

Reference Solution:

Accurately weigh about 100 mg of each solvent in a 100 ml volumetric flask, dissolve and dilute to volume with diluent: dilute 1.0 ml of this solution to 100 ml with diluent to obtain a solution containing each solvent at about 0.01 mg/ml (about 250 ppm).

Test Solution:

In a 20 mL vial for headspace accurately weigh about 200 mg of ralfinamide methanesulfonate or its R-enantiomer to be tested and dissolve it with 5 ml of diluent (conc. 40 mg/ml).

Chromatographic Conditions:

The chromatographic procedure is carried out by using:
Column: a fused silica capillary column OVG43 (6% polycyanopropylphenylsiloxane-94% polydimethylsiloxane) 30 m long, 0.53 mm I.D., film thickness 3.00 μm, or equivalent;

Carrier (helium) at 35 cm/sec;
Injection: split mode, split ratio 1:5;
Injector temp. 140° C.;
Temperature program: 0-20 min isothermal at 40° C. 20-40 min linear from 40° C. to 240° C. at a rate of 10° C./min, 40-60 min isothermal at 240° C.;
Detector: FID at 250° C.
Headspace equilibration temperature: 105° C.;
Equilibration time: 45 min;
Transfer line temperature: 110° C.;
Pressurization time: 30 sec;
Injection volume 1 ml;
Diluent: N,N-dimethylformamide.

Procedure:

Inject blank (diluent), three times the reference solution and once the test solutions and record the chromatograms.

In the reference chromatograms verify that:

the relative standard deviation of the solvents peak areas in the three replicates of the reference solution must be not more than 20%.

Calculate the content of each solvent in the tested sample of ralfinamide methanesulfonate or its R-enantiomer by external standard calculation.

The following table reports the detection and quantitation limits:

| Solvent | Detection limit (LOD) | Quantitation limit (LOQ) |
|---|---|---|
| Methanol | 6 ppm | 13 ppm |
| Acetone | 6 ppm | 25 ppm |
| Isopropanol | 6 ppm | 25 ppm |
| Toluene | 6 ppm | 50 ppm |

Example 19

Alkyl Methanesulfonate (MMS/EMS/IMS) Determination by GC/MS in (S) or (R)-2-[4-(2-fluorobenzyloxy)benzylamino]propanamide Methanesulfonate Form H and Form A The method is used for determination of the content of methylmethanesulfonate (MMS), ethyl methanesulfonate (EMS) and isopropyl methanesulfonate (IMS) in a sample of ralfinamide methanesulfonate or its R-enantiomer.

The presence of residual alcoholic solvents may contribute to the quantity of the corresponding alkyl methanesulfonate detected in the ralfinamide methanesulfonate (and its R-enantiomer) sample.

The determination is carried out according to the following conditions:

Stock Reference Solution:

Accurately weigh about 50 mg of MMS, EMS and IMS reference compound in a 50 ml volumetric flask, dissolve and dilute to volume with diluent; dilute 1 ml of this solution to 50 ml with diluent (stock solution 1), to obtain a solution containing MMS, EMS and IMS at about 20 µg/ml (about 500 ppm); dilute 1.0 ml of the stock solution 1 to 10 ml with diluent (stock solution 2), to obtain a solution containing MMS, EMS and IMS at about 2 µg/ml (about 50 ppm).

Reference Solution

Dilute to volume 50 µl of stock solution 2 with diluent in a 5 mL volumetric flask.

Test Solution:

Accurately weigh about 195-205 mg of test product in a 5 ml volumetric flask, dissolve and dilute to volume with diluent.

Chromatographic Conditions:

The chromatographic procedure is carried out by using:

Column: a fused silica capillary column DB-35-MS (35% phenyl-methyl polysiloxane) 60 m long, 0.25 mm I.D., film thickness 0.25 µm, or equivalent;

Carrier (helium) at 1.0 ml/min;

Injection: split mode, split ratio 5:1;

Injector temp. 160° C.;

injection volume 2 µl;

diluent N,N-dimethylformamide.

Temperature program: 0-4 min isothermal at 50° C., 4-28 min linear from 50° C. to 170° C. at a rate of 5° C./min, 28-30 min isothermal at 170° C., 30-32.75 linear from 170° C. to 280° C. at a rate of 40° C./min. 32.75-34.75 min isothermal at 280° C.;

Detector: Quadrupole mass spectrometer

Temperature ion source: 230° C.

Temperature MS transfer line: 280° C.

Selective masses: 79, 80, 109, 123

Procedure:

Inject once blank solution, five times the 0.5 ppm reference solution and finally once the test solutions and record the chromatograms.

In the reference chromatograms verify that:

the relative standard deviation of the peak areas of MMS, EMS and IMS in the five replicates of the 0.5 ppm reference solution must be NMT 10%.

Calculate the content of MMS, EMS and IMS in the tested sample of ralfinamide methanesulfonate or its R-enantiomer by external standard calculation.

The value of the limit of quantitation (LOQ) for MMS, EMS and IMS is 0.1 ppm by weight. The value of the limit of detection (LOD) is 0.05 ppm by weight.

Example 20

Differential Scanning Calorimetry (DSC)

Data are collected by means of a DSC2010 calorimeter (TA Instruments, New Castle, Del., USA), between ambient temperature and 280° C., under nitrogen purging of 70 ml/min, at scanning rate of 10° C./min; runs were performed on 2-3 mg samples in non-hermetically sealed aluminum pan.

Thermogravimetric Analysis (TGA)

Data are collected by means of a TG2050 thermobalance (TA Instruments New Castle, Del. USA) between ambient temperature and 280° C., under nitrogen purging of 100 ml/min, at scanning rate of 10° C./min: runs were performed on samples of 15-20 mg. In Form A no weight change was observed up to 240° C. Significant weight loss above this temperature is due to drug decomposition. Form H crystallized from water shows a dehydration endotherm at about 95+/−2.1° C. (see DSC data above) accompanied by a weight loss of 2.14%. K.F. titration confirms a water content value of 2.2% by weight, corresponding approximately to a water: (S) or (R)-2-[4-(2-fluorobenzyloxy)benzylamino]propanamide methanesulfonate molar ratio of 1:2.

Example 21

High Resolution and Solid State Cross-Polarization (CP) Magic-Angle Spinning (MAS) Nuclear Magnetic Resonance (NMR) Spectra High Resolution NMR Spectra The $^1$H NMR spectra are acquired in $CD_3CN$ as solvent, on a Bruker Avance 500 spectrometer, operating at 500.15 MHz ($^1$H). The experiments are carried out at room temperature (27° C.) and with TMS as reference.

Solid State CP MAS NMR Spectra

Solid state NMR spectra are obtained at 500.15 ($^1$H) and 125.62 ($^{13}$C) MHz on a Bruker Avance 500 spectrometer, equipped with a 4 mm magic angle spinning (MAS) broadband probe (spinning rate $v_R$ up to 15 kHz). The MAS spectra are recorded on solid samples, (typically 0.15 g); each sample is packed into a 4-mm MAS rotor (50 μl sample volume) spinning up to 9 kHz (at higher rotation speed no spectral features differences are revealed) and at a temperature of 300° K. For the $^{13}$C NMR spectra, variable amplitude cross polarization (CP) methods, 10000 scans and a delay of 2.0 s are used for the acquisition. The zero memory go (zg), and cross polarization (cp) avance (av) are characteristic pulses sequences of Bruker software.

Example 22

PXRD Analysis

PXRD pattern are registered by means of a Thermo ARL X'tra diffractometer operating in theta-theta Bragg-Brentano geometry equipped with a Peltier cooled Si(Li) solid state detector by using Cu $K_\alpha$ radiation ($\lambda=1.54178$ Å) generated with 40 KV and 30 mA. Digitized patterns are collected in the 3-40° 2θ range, by using 0.02° steps and 2 sec/step counting time.

The invention claimed is:

1. A crystalline hemihydrate pseudopolymorph form H of a methanesulfonate salt of ralfinamide, or its R-enantiomer, exhibiting an X-ray powder diffraction pattern (PXRD) having characteristics peaks expressed in degree 2θ at:
4.09; 7.09; 10.06; 11.64; 12.34; 16.38; 17.00; 17.47; 19.26; 20.11; 20.63; 21.34; 21.97; 23.35; 23.86; 24.12; 25.29; 27.15; 27.61; 28.02; 28.74; 29.62; 30.02; 30.51; 31.29; 31.81; 32.89; 33.35; 33.93; 35.10; 35.39; 35.62; 36.22; 38.91 and 39.50.

2. The crystalline hemihydrate pseudopolymorph form H of the methanesulfonate salt of ralfinamide, or its R-enantiomer, of claim 1 further characterized in that it exhibits the following characteristics:
   (a) Single Crystal X-ray Crystallographic Analysis crystal parameters:
   Cell parameters: a=5.844(4) Å
   b=15.221(10) Å
   c=21.670(15) Å
   α=90°
   β=96.361(10)°
   γ=90°
   V=1916(2) Å$^3$
   Space group P2$_1$, monoclinic
   Z (multiplicity) 2
   Density calculated, g/cm$^3$ 1.413
   wherein a, b and c define the length of the sides of the unit cells; α, β and γ define the relative angles of the cell sides; and V defines the volume of the cell;
   (b) a Karl Fisher analysis shows a content 2.2 percent by weight of water which is consistent with the presence of one mole of water for two moles of ralfinamide methanesulfonate or its R-enantiomer;
   (c) a TGA pattern shows a loss of weight of 2.14 percent at 95° C. which is consistent with the presence of one mole of water for two moles of ralfinamide methanesulfonate or its R-enantiomer;
   (d) a DSC pattern shows two endothermic peaks: a first one at 95.1±2° C. and a second one at 241.3±0.3° C.; and
   (e) a solid state $^{13}$C-CPMAS/NMR pattern shows the following chemical shifts (ppm): 13.5; 39.05; 40.02; 44.6; 49.3; 51.9; 54.0; 56.7; 57.4; 61.2; 83.0; 84.0; 85.0; 97.0; 111.3; 113.2; 116.6; 121.6; 124.1; 126.9; 129.0; 129.7; 133.1; 156.7; 169.1; 182.0; 185.5; 189.0; 193.9; 196.45; 199.2; 201.0; 202.0 and 205.0.

3. A medicament comprising the crystalline hemihydrate pseudopolymorph form H of the methanesulfonate salt of ralfinamide, or its R-enantiomer, of claim 1.

4. A pharmaceutical formulation containing as an active ingredient a compound of claim 1.

5. The pharmaceutical formulation according to claim 4 which is a modified release formulation.

6. The pharmaceutical formulation according to claim 5 which is a tablet or coated tablet.

7. The pharmaceutical formulation of claim 4 which contains as the active ingredient ralfinamide methanesulfonate, or its R-enantiomer, as crystalline hemihydrate pseudopolymorph form H in an amount equivalent to 40, 80, 160 or 320 mg of free base.

* * * * *